(12) United States Patent
Ricci et al.

(10) Patent No.: US 7,702,502 B2
(45) Date of Patent: *Apr. 20, 2010

(54) APPARATUS FOR SIGNAL DECOMPOSITION, ANALYSIS AND RECONSTRUCTION

(75) Inventors: Carlos A. Ricci, Apple Valley, MN (US); Vladimir V. Kovtun, Inver Grove Heights, MN (US)

(73) Assignee: Digital Intelligence, L.L.C., Apple Valley, MN (US)

( * ) Notice: Subject to any disclaimer, the term of this patent is extended or adjusted under 35 U.S.C. 154(b) by 1093 days.

This patent is subject to a terminal disclaimer.

(21) Appl. No.: 11/360,135

(22) Filed: Feb. 23, 2006

(65) Prior Publication Data

US 2006/0200034 A1    Sep. 7, 2006

Related U.S. Application Data

(60) Provisional application No. 60/656,630, filed on Feb. 23, 2005.

(51) Int. Cl.
*G10L 19/00* (2006.01)
*A61B 5/04* (2006.01)

(52) U.S. Cl. .................. 704/205; 704/213; 600/509; 600/513

(58) Field of Classification Search .............. 704/201, 704/203, 205, 206, 500, 501, 213; 600/509, 600/512, 513
See application file for complete search history.

(56) References Cited

U.S. PATENT DOCUMENTS

| | | | |
|---|---|---|---|
| 3,819,920 A | 6/1974 | Goldfischer | |
| 3,993,862 A * | 11/1976 | Karr | 358/426.01 |
| 4,193,393 A | 3/1980 | Schlager | |
| 4,251,831 A | 2/1981 | Kamath | |
| 4,314,105 A * | 2/1982 | Mozer | 375/246 |
| 4,461,022 A * | 7/1984 | Slagley | 704/205 |
| 4,633,884 A | 1/1987 | Imai et al. | |
| 4,680,797 A | 7/1987 | Benke | |
| 4,736,295 A | 4/1988 | Lachiver et al. | |

(Continued)

OTHER PUBLICATIONS

Cetin, A. E., et al., "Compression of Digital Biomedical Signals", *The Biomedical Engineering Handbook: Second Edition*. Joseph D. Bonzino, Ed. CRC Press LLC, (2000),Chapter 54.

(Continued)

*Primary Examiner*—Martin Lerner
(74) *Attorney, Agent, or Firm*—Charles A. Lemaine; Lemaire Patent Law Firm, P.L.L.C.

(57) ABSTRACT

The present invention provides a system and method for representing quasi-periodic ("qp") waveforms comprising, representing a plurality of limited decompositions of the qp waveform, wherein each decomposition includes a first and second amplitude value and at least one time value. In some embodiments, each of the decompositions is phase adjusted such that the arithmetic sum of the plurality of limited decompositions reconstructs the qp waveform. These decompositions are stored into a data structure having a plurality of attributes. Optionally, these attributes are used to reconstruct the qp waveform, or patterns or features of the qp wave can be determined by using various pattern-recognition techniques. Some embodiments provide a system that uses software, embedded hardware or firmware to carry out the above-described method. Some embodiments use a computer-readable medium to store the data structure and/or instructions to execute the method.

25 Claims, 25 Drawing Sheets

U.S. PATENT DOCUMENTS

| | | | |
|---|---|---|---|
| 5,115,240 | A | 5/1992 | Fujiwara et al. |
| 5,230,038 | A | 7/1993 | Fielder et al. |
| 5,392,044 | A | 2/1995 | Kotzin et al. |
| 5,486,867 | A | 1/1996 | Hsu et al. |
| 5,500,874 | A * | 3/1996 | Terrell .................. 375/232 |
| 5,730,142 | A | 3/1998 | Sun et al. |
| 5,749,367 | A | 5/1998 | Gamlyn et al. |
| 5,778,881 | A | 7/1998 | Sun et al. |
| 5,828,995 | A * | 10/1998 | Satyamurti et al. ......... 358/1.18 |
| 6,008,618 | A * | 12/1999 | Bose et al. ................ 318/811 |
| 6,020,840 | A | 2/2000 | Ong |
| 6,389,308 | B1 | 5/2002 | Shusterman |
| 6,470,210 | B1 * | 10/2002 | Chen et al. ................. 600/515 |
| 6,510,339 | B2 | 1/2003 | Kovtun et al. |
| 6,512,944 | B1 | 1/2003 | Kovtun et al. |
| 6,606,056 | B2 * | 8/2003 | Brogden .................. 342/372 |
| 6,618,617 | B2 * | 9/2003 | Chen et al. ................. 607/5 |
| 6,791,482 | B2 * | 9/2004 | Koyanagi .................. 341/61 |
| 6,914,935 | B2 | 7/2005 | Eklof |
| 6,925,324 | B2 | 8/2005 | Shusterman |
| 7,058,548 | B2 | 6/2006 | Pupalaikis et al. |
| 7,088,276 | B1 * | 8/2006 | Wegener .................. 341/155 |
| 7,200,435 | B2 * | 4/2007 | Ricci et al. ................. 607/9 |
| 7,254,187 | B2 * | 8/2007 | Mohan et al. ............. 375/323 |
| 2001/0023396 | A1 * | 9/2001 | Gersho et al. ............. 704/220 |
| 2004/0073098 | A1 | 4/2004 | Geva et al. |
| 2004/0078160 | A1 * | 4/2004 | Frei et al. ................. 702/79 |
| 2004/0264622 | A1 * | 12/2004 | Walsh et al. .............. 375/376 |
| 2006/0200035 | A1 * | 9/2006 | Ricci et al. ............... 600/513 |
| 2008/0002775 | A1 * | 1/2008 | Ricci et al. ............. 375/240.19 |
| 2008/0015452 | A1 * | 1/2008 | Ricci et al. ............... 600/509 |
| 2008/0181332 | A1 * | 7/2008 | Tian et al. ................ 375/308 |

OTHER PUBLICATIONS

Chen, Ying-Jui, et al., "Multiplierless Approximations of Transforms with Adder Constraing", *IEEE Signal Processing Letters* vol. 9, No. 11, (Nov. 2002).

Kotteri, K., et al., "Design of Multiplierless, High-Performance, Wavelet Filter Banks with Image Compression Application", *IEEE Transactions on Circuits and Systems*, vol. 51 No. 3, Mar. 2004., (483-494).

Bracewell, Ronald N., "The Fourier Transform and its Applications", *McGraw-Hill*, (2000).

Cappe, Olivier, et al., "Inference in Hidden Markov Models", *Springer*(2005).

Duda, Richard O., et al., "Pattern Classification, Second Ed.", (2001).

Elliott, Richard J., et al., "Hidden Markov Models", *Springer-Verlag*, (1995).

Fliege, N. J., "Multirate Digital Signal Processing", *Wiley*, (1994).

Golub, Gene H., et al., "Matrix Computations, Third Ed.", *Hopkins*, (1996).

MacDonald, Iain L., et al., "Hidden Markov and Other Models for Discrete-valued Time Series", *Chapman*, (1997).

Openheim, Alan V., et al., "Discrete-Time Signal Processing, Second Ed.", *Wiley*, (1999).

Ozaktas, Haldun M., et al., "The Fractional Fourier Transform", *Wiley*, (2001).

Stoica, Petre, et al., "Spectral Analysis of Signals", *Prentice-Hill*, (2005).

Strang, Gilbert, et al., "Wavelets and Filter Banks", *Wellesley*, (1997).

Vapnik, Vladimir N., "The Nature of Statistical Learning Theory, Second Ed.", *Springer*, (2000).

Vetterli, Martin, et al., "Wavelets and Subband Coding", *Prentice-Hall*, (1995).

Xue, Qiuzhen, et al., "Late Potential Recognition by Artificial Neural Networks", *IEEE Trans Bio Eng*, vol. 44, (1997), 132-143.

\* cited by examiner

FIG. 6
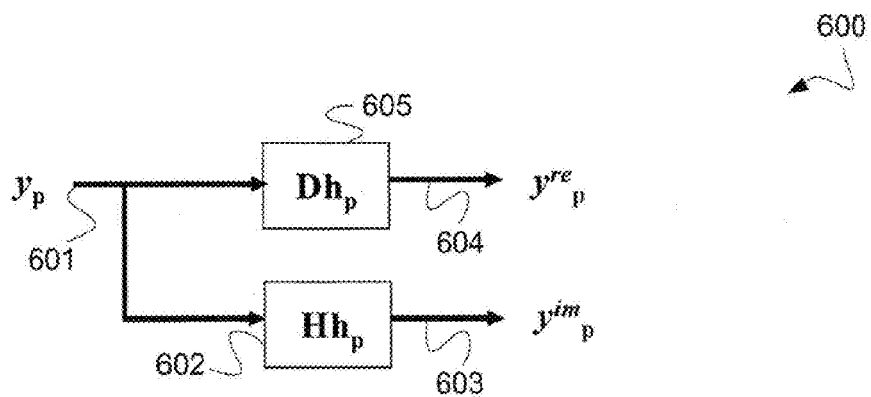
FIG. 7A
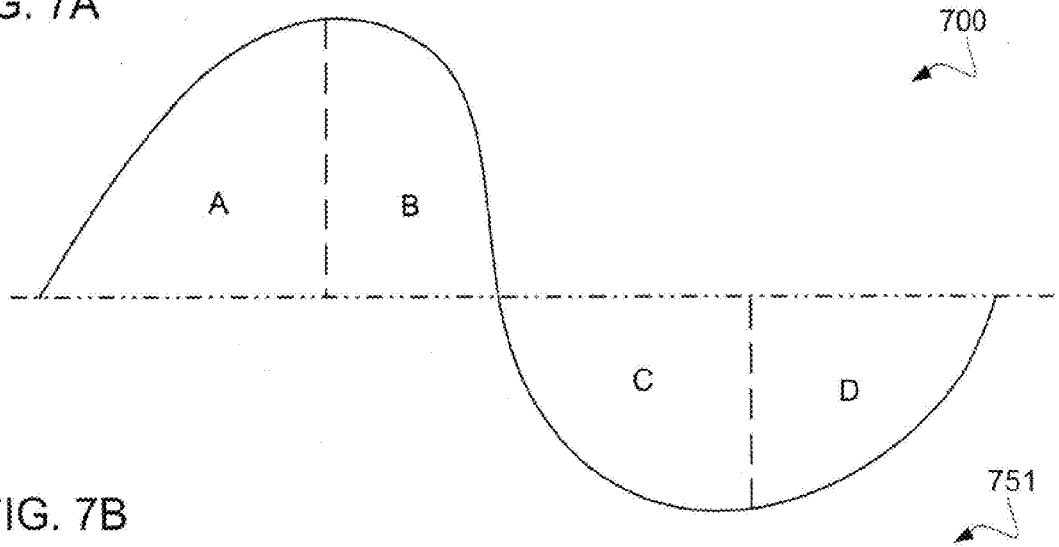
FIG. 7B
| QP LABEL | STARTS AT | ENDS AT |
| --- | --- | --- |
| A | POSITIVE-GOING ZERO CROSSING | POSITIVE PEAK |
| B | POSITIVE PEAK | NEGATIVE-GOING ZERO CROSSING |
| C | NEGATIVE-GOING ZERO CROSSING | NEGATIVE PEAK |
| D | NEGATIVE PEAK | POSITIVE-GOING ZERO CROSSING |

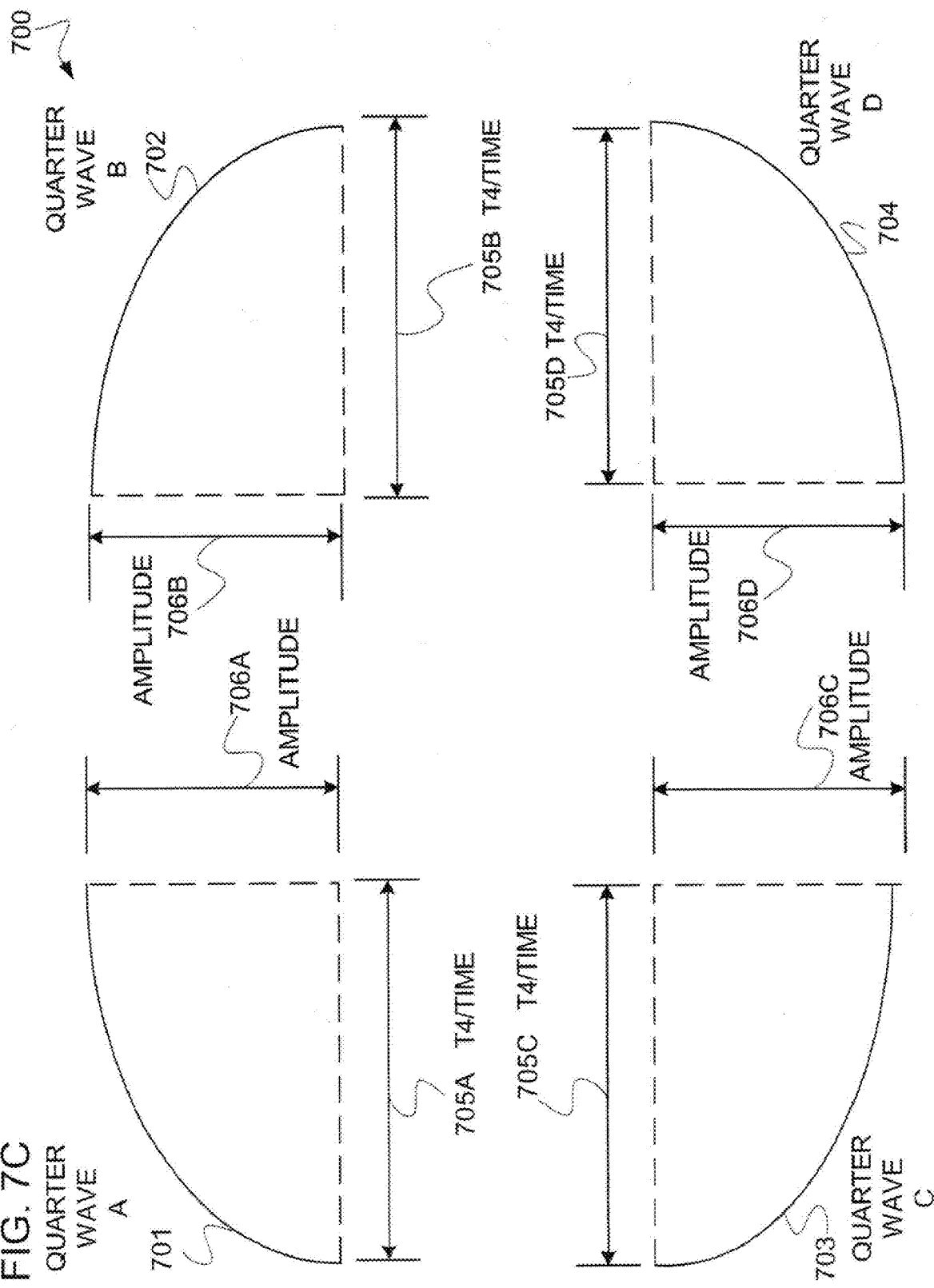

| Aa | Ab | Ac | Ad |
| Ba | Bb | Bc | Bd |
| Ca | Cb | Cc | Cd |
| Da | Db | Dc | Dd |

FIG. 8A

| 801 | 802 | 803 | 804 |
|---|---|---|---|
| OBJECT ID | T4 VALUE | PHASE LABEL | ATOMIC PERIOD VALUE |
| AMPLITUDE MEASUREMENT | TOTAL TIME ELAPSED | RELATIVE AMPLITUDE VALUE | RELATIVE T4 VALUE |
| 805 | 806 | 807 | 808 |

| 801 | 802 | 803 | 804 | 809 | 810 | 811 | 812 |
|---|---|---|---|---|---|---|---|
| OBJECT ID | T4 VALUE | PHASE LABEL | ATOMIC PERIOD VALUE | LEFT OBJECT | RIGHT OBJECT | LEFT HARMONIC | RIGHT HARMONIC |
| AMPLITUDE MEASUREMENT | TOTAL TIME ELAPSED | RELATIVE AMPLITUDE VALUE | RELATIVE T4 VALUE | LEFT NEIGHBOR | RIGHT NEIGHBOR | LOWER NEIGHBOR | |
| 805 | 806 | 807 | 808 | 813 | 814 | 815 | |
| UPPER NEIGHBOR | | | | | | | |
| 816 | | | | | | | |

| OBJECT ID | T4 VALUE | PHASE LABEL | ATOMIC PERIOD VALUE | LEFT OBJECT | RIGHT OBJECT | LEFT HARMONIC | RIGHT HARMONIC |
|---|---|---|---|---|---|---|---|
| 801 | 802 | 803 | 804 | 809 | 810 | 811 | 812 |

| AMPLITUDE MEASUREMENT | TOTAL TIME ELAPSED | RELATIVE AMPLITUDE VALUE | RELATIVE T4 VALUE | LEFT NEIGHBOR | RIGHT NEIGHBOR | LOWER NEIGHBOR |
|---|---|---|---|---|---|---|
| 805 | 806 | 807 | 808 | 813 | 814 | 815 |

| UPPER NEIGHBOR | RIGHT LOCAL PERIOD BY LABEL | LEFT LOCAL PERIOD TIME | RIGHT LOCAL PERIOD TIME | CYCLIC REGULARITY | AMPLITUDE MODULATION |
|---|---|---|---|---|---|
| 816 | 818 | 819 | 820 | 821 | 822 |

| LEFT LOCAL PERIOD BY LABEL |
|---|
| 817 |

852

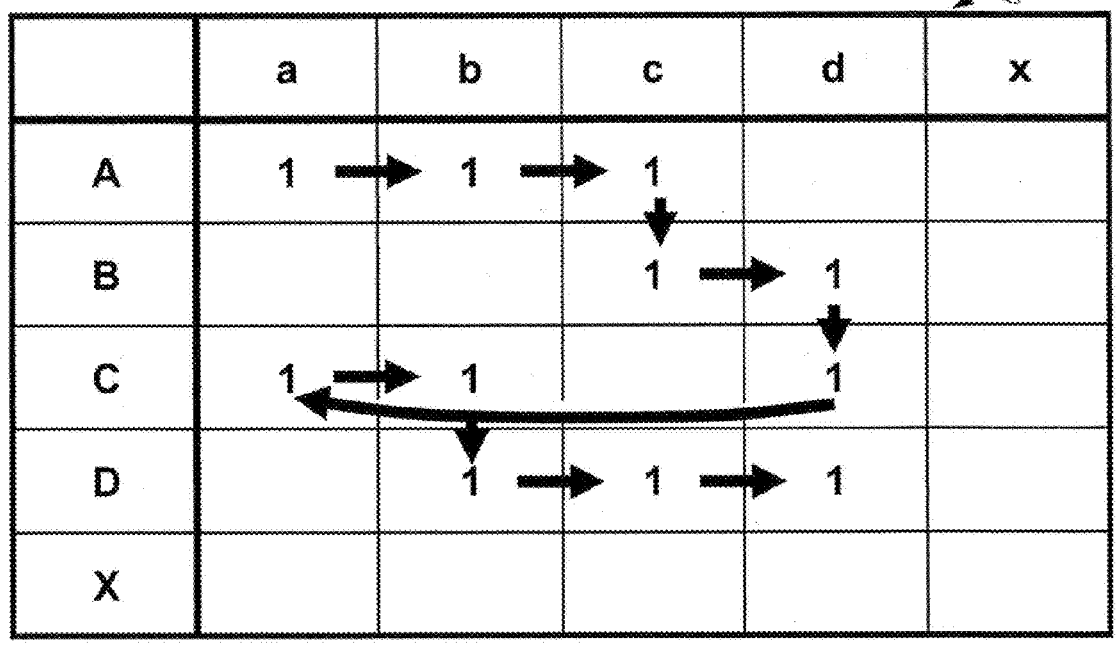

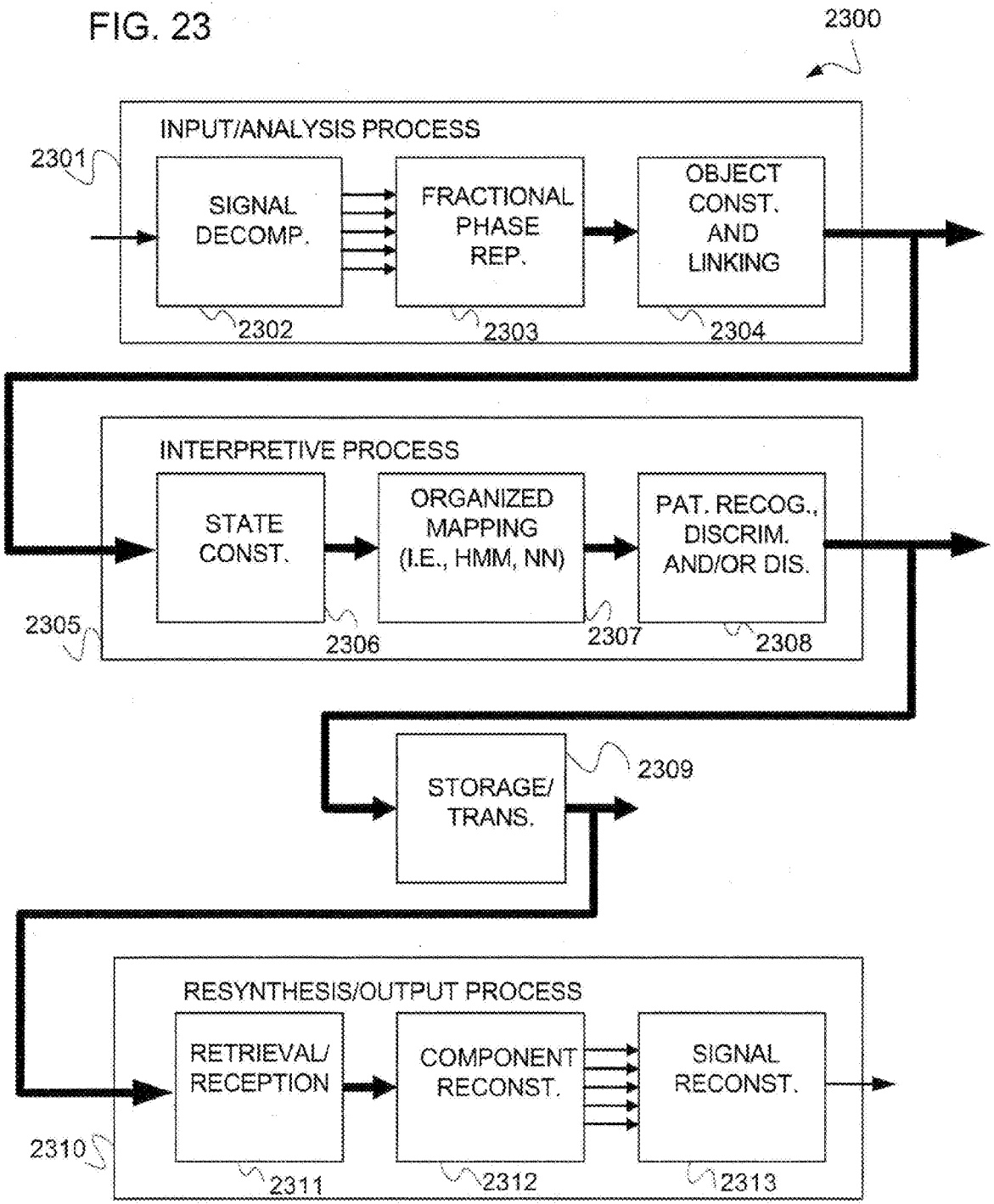

APPARATUS FOR SIGNAL DECOMPOSITION, ANALYSIS AND RECONSTRUCTION

CROSS-REFERENCE TO RELATED APPLICATIONS

This invention claims benefit of U.S. Provisional Patent Application 60/656,630 filed Feb. 23, 2005, which is hereby incorporated by reference in its entirety. This application is related to Applicants' copending U.S. patent application Ser. No. 11/360,223, filed Feb. 23, 2006, and titled "SYSTEM AND METHOD FOR SIGNAL DECOMPOSITION, ANALYSIS AND RECONSTRUCTION," which is hereby incorporated by reference.

FIELD OF THE INVENTION

This invention relates to the field of computer-implemented systems and methods, and more specifically a software-, embedded-circuits- or firmware-implemented system and method to decompose signals having quasi-periodic wave properties, store such signals in a data structure, analyze such signals, and reconstruct such signals from the data structure, and to optionally transmit such data structure over a communications channel.

BACKGROUND OF THE INVENTION

The digital representation of waveforms is a technology that is central to various sectors of industry where the detection of periodic and non-periodic waveforms can be critical to determining whether an erratic heartbeat, electrical short circuit, or some other problem exists. A digital representation must clearly and accurately represent the analog source of a waveform, but at the same time be able to accomplish such things as, compressing the incoming data into some manageable size, and maintain the integrity of the incoming data (i.e., making sure that the digital representation has enough fidelity to the original signal to be useful). Of additional import is the ability to have a digital representation that can consistently allow one to identify the presence and location of certain wave features, and/or that lends itself to certain types of automated analyses.

High fidelity digital representations are problematic for a number of reasons. First, they require relatively large amounts of space within which to store the digitized data. Put another way, the higher the fidelity of the digitized data, the larger the amount of storage needed. Another problem with high fidelity digital representations is that they can result in large amounts of digital data that has little or no import in terms of conveying meaning. For example, a periodic wave signal that merely repeats the same waveform does not convey much meaning to the person analyzing the waveform, and may in fact just take up storage space with unremarkable data. An additional problem is the repeated sampling, over sampling of such high fidelity data even though it is otherwise unremarkable. Such over sampling results in wasted processing bandwidth (i.e., processor cycles, and/or power) as well as data bandwidth (data storage space and/or transmission bandwidth).

One solution to the above-cited problems associated with a high fidelity digital representation is to devise a method for filtering and concentrating this high fidelity waveform data in such a manner that the integrity and significant features of the data is maintained, but while utilizing lower data bandwidth and lower processing bandwidth. Thus, one needs a method and structure that can efficiently and accurately capture the underlying waveform, with little or no degradation of the value and meaning of that waveform data.

SUMMARY OF THE INVENTION

Some embodiments of the present invention provide a system and method for representing a quasi-periodic (qp) waveform including: representing a plurality of limited decompositions of the qp waveform, wherein each decomposition includes a first and second amplitude value and at least one time value associated with the first amplitude value. In some embodiments, at least one time value is associated with a second amplitude value, and each of the decompositions is phase adjusted such that the arithmetic sum of the plurality of limited decompositions reconstructs the qp waveform.

In some embodiments, the present invention provides a method for analyzing qp waveforms including an input/analysis process that takes an original qp waveform signal and produces from it a stream of descriptive objects. Within the input/analysis process, a signal decomposition process decomposes the original quasi-periodic signal into a set of corresponding component signals (herein these are also called "component waves," "decomposition components," or simply "components"). The component signals are then processed into a fractional-phase representation to identify the object boundaries and measure basic attributes. The corresponding object-related information is then passed to an object-construction-and-linking process that constructs a stream of objects, filling out whatever additional object-related and/or data-structure-related information is needed for a particular application. An interpretive process is then applied that takes the stream of objects and produces an interpretation of the original qp waveform signal. Within the interpretive process, a state constructor that takes the stream of objects and constructs states from them is applied. Further, an organized mapping process is utilized, where the information is mapped in state space that includes both ad-hoc and structured mapping utilizing Hidden Markov Models and Neural Networks. Additionally, an organized mapping process is applied, where the information is mapped in a vector space along one or more object attributes and mapping utilizing vector-space methods, including Hidden Markov Models or Neural Networks. Furthermore, a pattern-recognition discrimination process to transform the mapped information into a human-interpretable form is applied. Then a storage process takes the object stream and samples of this object stream and stores some or all of the samples in a memory. Optionally, a storage process takes the object stream and transmits some or all of the objects over a communications link. In some embodiments, a re-synthesis/output process takes the object stream from a communications link and/or storage and reconstructs an estimate of the original signal(s).

In some embodiments, the method further includes placing the first and second amplitude values, the first time value, and the second time value in a data structure.

Some embodiments further include a computer-readable medium having stored thereon a data structure optionally three or more fields including: a first field containing an object ID, a second field containing a T4 value, a third field containing a phase label, a fourth field containing an amplitude measure, a fifth field containing the total time elapsed, a sixth field containing a relative amplitude value, a seventh field containing a relative T4 value, and an eighth field containing an atomic period value, a ninth field containing a memory address of a left neighbor, a tenth field containing a memory address of a right neighbor, an eleventh field containing a memory address of a left object, a twelfth field containing a memory address of a right object, a thirteenth field containing a left harmonic, a fourteenth field containing a right harmonic, a fifteenth field containing a memory address for an upper neighbor, a sixteenth field containing a memory address for a lower neighbor, a seventeenth field containing data relating to cyclic regularity, an eighteenth field containing data related to a left local period time, a nineteenth field containing data related to a right local period time, a twentieth field containing data related to a left harmonic, a twenty-first field containing data related to a right harmonic, and a twenty-second field related to amplitude modulation.

Other embodiments include a computer-readable medium having executable instructions stored thereon for causing a suitable programmed central processor to perform a method including: taking input in the form of a binary representation of a base waveform, passing this binary representation through a series of bandpass filters, taking the component-signal output of the bandpass filters and extracting data from these components waves, and storing the data into a plurality of data structures. The method further including organizing the data structure. The method further including outputting the data in the plurality of data structures in the form of a graphical representation. The method further including processing the data in the data structure using a Hidden Markov model. The method further including processing the data in the data structure using a Neural Network.

In other embodiments, the invention provides a system for analyzing qp waves including: a database containing data related to qp waves, a CPU operatively coupled to the database. A computer readable medium operatively coupled to the CPU containing instructions in some CPU readable format or language, which allows the CPU to: take input in the form of a binary representation of a base waveform, passing this binary representation through a series of bandpass filters, taking a component wave output of the bandpass filters, extracting data from these components waves, and storing the data into a plurality of data structures. Additionally, an input device is operatively coupled to the CPU, and output device operatively coupled to the CPU, the CPU operatively coupled to an internet, and a terminal for receiving data from the data structures via the internet.

In some embodiments, the invention provides a system for analyzing qp waves. This system includes a set of electrodes each with one end operatively connected to the skin surface or disposed below the skin surface of the body, an optional set of electrodes at least one end of which is operatively connected to the heart itself, a second end of a set of electrodes operatively coupled to an analog to digital converter, the analog to digital converter operatively coupled to a microprocessor unit, a computer readable medium containing program instructions operatively coupled to the microprocessors unit, a memory storage operatively coupled to the microprocessor unit, a communications module operatively coupled to the microprocessor unit, and a power supply operatively coupled to the analog to digital converter, microprocessor unit and communications module. The system further including: a communications module, a microprocessor unit, a computer readable medium containing a set of application instructions, an associated storage module containing data values representing the original signal, a Human-Computer Interface by which an operator may interact with the microprocessor unit, an input device, and an output device.

In some embodiments, the invention is implemented using a multiplierless architecture in conjunction with embedded circuits. In still other embodiments, the invention is implemented using firmware, and in still other embodiments the invention is implemented using software.

BRIEF DESCRIPTION OF THE DRAWINGS

FIG. 6 is a block diagram 600 showing a section of an analytic filter bank.

FIG. 7A is a waveform 700 illustrating a cycle from one component signal that is broken up into four quarter-phases.

FIG. 7B is a table 751 illustrating the various unique features such as the positive-going and negative-going zero crossings, and the positive and negative peaks of the component signal that are analyzed by the invention.

FIG. 7C shows how four quarter-phases (i.e., reference numbers 701, 702, 703, 704) of waveform 700 may each be characterized simply using two parameters.

FIG. 8A is a diagram of a data structure 800.

FIG. 8B is a diagram of a data structure 851.

FIG. 8C is a diagram of a data structure 852.

FIG. 9A is a state matrix 900 depicting state transitions arising from transitions between pairs of quarter-phases.

FIG. 9B is a state-transition matrix 951 depicting state transitions arising from transitions between pairs of quarter-phases.

FIG. 23 is a block diagram of a system 2300 of an Input/Analysis process 2301, an Interpretive Process 2305, a Storage/Transmission block 2309, and a Resynthesis/Output process 2310.

DETAILED DESCRIPTION OF THE INVENTION

Figure 1:
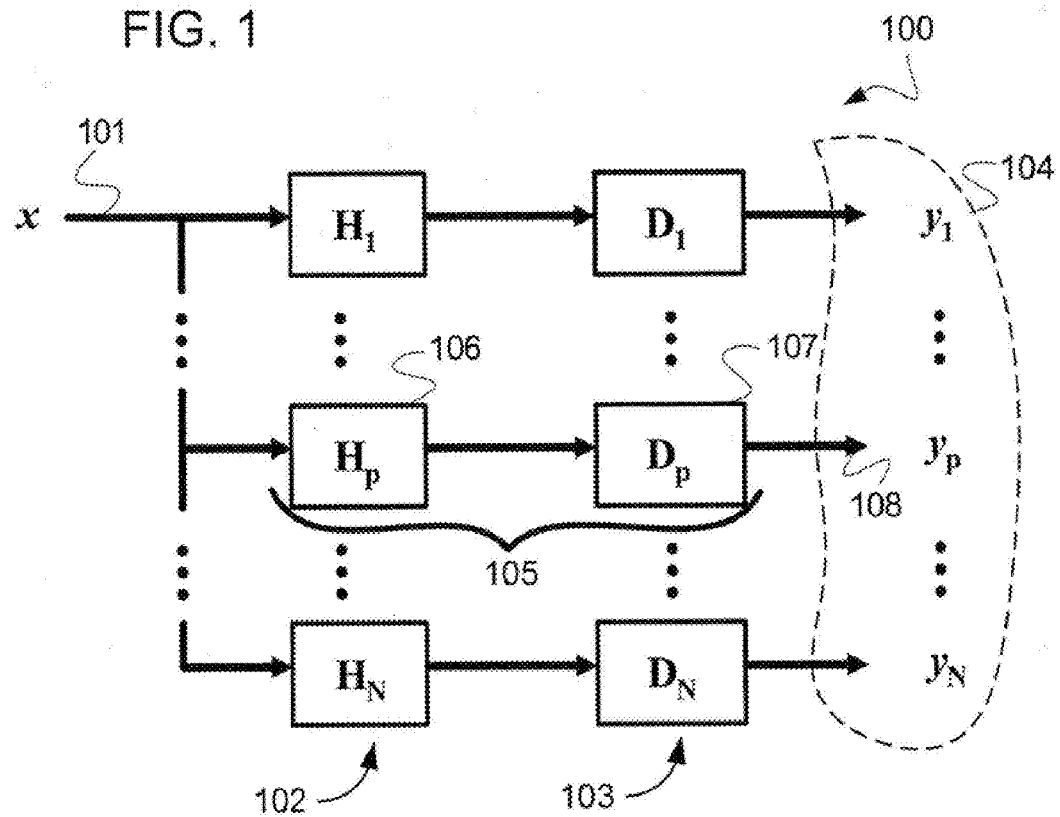
FIG. 1 is a block diagram of a parallel filter bank 100.

Although the following detailed description contains many specifics for the purpose of illustration, a person of ordinary skill in the art will appreciate that many variations and alterations to the following details are within the scope of the invention. Accordingly, the following preferred embodiments of the invention are set forth without any loss of generality to, and without imposing limitations upon the claimed invention.

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component that appears in multiple Figures. Signals and connections may be referred to by the same reference number or label, and the actual meaning will be clear from its use in the context of the description.

In some embodiments, the present invention provides a high-fidelity digital representation by using a method for filtering-and concentrating high-fidelity waveform data in such a manner that the integrity and significant features of the data are maintained, while utilizing less storage space and fewer processor cycles than conventional techniques. In some embodiments, the present method takes a high fidelity wave signal (i.e., a qp or the base wave signal), passes this signal through a filter bank that decomposes or separates out this signal into series of locally periodic component signals, and then stores these component signals and their associated characteristics into a data structure. This data structure can then be used to reconstruct the base wave signal, to search for certain features or patterns within the wave signal, or a variety of other purposes. One advantage of the present method is that insignificant or undesirable data can be filtered out and prevented from taking up storage space. In some embodiments, the filters can be adjusted to allow certain wave features to be stored, while other features are disregarded. This ability to adjust filters has the added advantage that when a sample of wave data is taken, it is more likely that the sampling will be of significant wave data, rather than insignificant wave data thus resulting in fewer processor cycles needed for wave sampling.

Another advantage of this method is that by storing the component wave signals into a data structure, these signals can be easily utilized, manipulated for a variety of purposes. For example, a component wave signal can be analyzed for certain characteristics or patterns. These characteristics or patterns of the component wave signal can then be compared to the other components or the base waveform itself to give a better idea of the significance of the characteristic or pattern.

Decomposition and Filter Banks—Generally

To begin to understand the use of filter banks in the decomposition of a base wave or original signal it is necessary to understand a base wave signal (i.e., an original signal) as being quasi-periodic (qp). Quasi-periodic means that an original signal may be considered as the linear combination of a series of locally periodic component signals having different periods and/or shapes. Locality here is taken to be on the order of a few cycles of the component in question, though in certain cases can be as small as one cycle, such as, for example, if a certain transient condition to be detected or analyzed sporadically elicits such a component.

Starting with the assumption of a qp waveform, decomposition of the original signal involves the local estimation of the qp components of the original signal. Many methods have been proposed, developed, and are well established in the art. Examples of these are the Short-Time Fourier Transform (STFT), Wavelet Transform, and generally any method that may be cast as a bank of filters (Filter Bank). (See *Wavelets and Filter Banks*, by Gilbert Strang and Truong Nguyen, Wellesley College, 1996.) The individual filters in the filter bank, herein called component filters or component bands, are designed to emphasize (i.e., correlate to) a locally periodic component of interest in the original signal, and so will tend to have impulse responses that oscillate over a local region of time. The frequency responses of the component filters will tend to have relatively confined regions (passbands) where the magnitude is substantially higher than in other regions. The width of the passband (the bandwidth) is typically measured at the half-power points (i.e., the difference of the two frequencies where the magnitude response is a factor of sqrt (2)/2 below the maximum value in between). A single component filter may have more than one passband, for example if the component is represented by a harmonic series. One may denote the outputs of these component filters as the component outputs, or the component signals.

The design of such filter banks is well understood and established in the art. (See *Multirate Digital Signal Processing: Multirate Systems-Filter Banks-Wavelets*, by N. J. Fliege, John Wiley & Sons, 2000.) Of specific interest here is that the component filters match, in some useful sense, the underlying local behavior of the original signal. Many approaches are readily available. For example, a high-resolution time-frequency analysis of the original signal could be performed to simultaneously identify frequency bands and time-widths of interest, (i.e., by studying local peaks of signal energy on the time-frequency plane). Alternatively, or in conjunction, an autoregressive moving average ("ARMA") model could be generated of the original signal. The ARMA model, itself a filter, may be decomposed into component filters using pole and zero separation techniques, such as partial fraction expansion, or any established transformation from cascade to parallel form. Multiple ARMA models could be formed by ARMA modeling each output of a relatively coarse filter bank. Alternatively, or in conjunction, a Karhunen-Loeve Transform (KLT) or a Singular-Value Decomposition (SVD) could be performed on the convolution matrix or correlation matrix estimate formed from a finite time window of the original signal to either directly produce a bank of filters, or to identify filters that correlate to the principal components of the original signal (i.e., a Principal Components Analysis, or PCA). (See *Matrix Computations, 3rd Edition*, by G. H. Golub, and C. F. Van Loan, Johns Hopkins University Press, 1996.) The identified components of interest could then be used directly or approximated with simpler wavelets. Generally, the decomposition of the original signal may employ any linear or nonlinear method that produces a moving local estimate of the underlying locally periodic components of the original signal.

In some embodiments, prior knowledge of the original wave signal may also be used to define component bands. For example, in some embodiments, an electrocardiogram ("ECG") signal is expected to have a strong component at the fundamental heart rate. Therefore, for example, in some embodiments, a component is designed having a passband from roughly 0.5 Hz to 5 Hz, to represent a range of expected heart rates.

Generally, the time widths of the impulse responses of the filters in the bank are inversely proportional to the bandwidths of their frequency responses, thus representing a tradeoff in time resolution and frequency resolution. Of primary interest is that the time width be narrow enough to be substantially representative of the duration over which a corresponding underlying locally periodic component will be locally stable, while still maintaining sufficient resolution in frequency. Such tradeoffs are well understood and established in the art, and fall under the class of Spectral Estimation. (See *Spectral Analysis of Signals*, by Petre Stoica and R. L. Moses, Prentice-Hall, 2005.)

One may define a reconstructed signal, or reconstruction, to be the signal resulting from taking the sum of the component signals at each point in time (i.e., the linear combination of the component signals at each point in time is understood here as a "generalized sum"). In some embodiments, the component filters are designed such that the reconstructed signal is a satisfactory approximation of the original signal. The type and quality of the approximation, and therefore the quality of the signal that can be reconstructed, will depend strongly upon the application, but may be measured, for example, using well-established error-distance measures, such as, for example, mean-square error (MSE). (See *Some comments on the minimum mean square error as a criterion of estimation*, by C. Radhakrishna Rao, Technical report/ University of Pittsburgh-Department of Mathematics and Statistics-Institute for Statistics and Applications, 1980.) The approximation would need qualification, for example, in the case where the original signal was comprised of qp components plus wideband noise, and the reconstruction estimated the components while exhibiting substantially no noise.

Note that in the above sense, the frequency responses of the component bands, when taken as a whole, need not cover the entire spectrum to the highest frequency of interest. Frequency bands may be excluded in which relatively little signal energy exists and/or where a poor signal-to-noise ratio (SNR) exists. Additionally, in some embodiments, the time and/or phase alignment of the component filter impulse responses and/or the component signals is assumed to be understood as part of this invention, for the purpose of producing or representing an adequate reconstruction, including the various well-understood conditions for perfect and approximate reconstruction filter banks (see *Wavelets and Subband Coding*, M. Vetterli and J. Kovacevic, Prentice-Hall, 1995). The alignment may, for example, take into account the various delays inherent among the impulse responses in the filter bank. Such alignment may also be accounted for in the timing representations embedded in the processing of the component signals, such as in the data structures, by recording any necessary time and/or phase offsets in conjunction with, or added to, any timing and/or phase information for the components. If signal reconstruction is necessary, such timing information may thus be applied within the reconstruction process.

Moreover, in some embodiments, the impulse responses may be linear phase (symmetric/antisymmetric), minimum phase, or dispersive (having asymmetric response but not linear phase), provided that they meet the above signal reconstruction criteria.

In all of the above filter bank embodiments, an analytic form may be included, wherein both the above component signals and their Hilbert transforms are produced. This may be accomplished by any of the means well understood and established in the art. (See *The Fourier Transform and Its Applications 3rd Edition*, by R. Bracewell, McGraw-Hill, 1999.) For example, in some embodiments, the output of each component filter in the bank is provided to the input of a Hilbert transformer, where the component filter output is taken as the real part and the Hilbert transformer output is taken as the imaginary part of a resulting analytic signal. In another embodiment, a second bank of component filters may be provided, each component filter having an impulse response that is the Hilbert transform of its corresponding component filter from the first bank. In either case, an analytic form of each component signal (e.g., an analytic component signal) is formed by taking the component signal of each component filter as the real part and the Hilbert transformed version of that component signal as the imaginary part. One may note that the STFT inherently produces an analytic form for the components.

The Hilbert transform need not be ideal, only that the frequency-domain phase response of the effective component filter for the imaginary part be offset by substantially 90 degrees from the phase response of the corresponding component filter for the real part, and only over frequency ranges where the frequency response magnitudes are sufficiently high to be of interest (e.g., above some arbitrary threshold, say 20 dB below the peak magnitude). Of course, the frequency response magnitudes of the real-imaginary filter pair should be substantially equal over these frequency ranges, or at least equivalent up to some predetermined level of equivalence, based, for example, upon an error-distance measure or maximum allowable deviation in decibels.

These analytic component signals make available the instantaneous analytic magnitude (i.e., the "magnitude" or "amplitude") and the instantaneous analytic phase of the component signal. These may be computed, for each point in time of interest, from the magnitude and principal argument of the angle in the complex plane.

Decomposition and Filter Banks—The Present Invention

The following are example embodiments of the method of decomposition and the filter banks utilized in this invention. In terms of notation, capital letters used for the transfer functions signify frequency-domain transfer functions, but imply their time-domain counterparts as well. The converse also holds true (i.e., lower-case letters signifying the impulse responses of the blocks also imply their corresponding frequency-domain transfer-function counterparts). Additionally, cascading of blocks implies multiplication of their corresponding transfer functions in the frequency domain and/or convolution of their corresponding impulse responses in the time domain, as is well established and understood in the art. (See *Discrete-Time Signal Processing*, by A. V. Oppenheim, R. W. Schafer, and J. R. Buck, Prentice-Hall, 1999.)

Blocks are considered to be linear, time-invariant systems, and so in a given implementation the blocks include a certain cascade of blocks may be rearranged in any order within the cascade. These filter banks may be applied as a bank of filter sections arranged in a parallel form known here as a Parallel-Form Kovtun-Ricci Wavelet Transform, and/or these filter banks may be applied as a bank of filter sections arranged in a cascade form known here in as a Cascade-Form Kovtun-Ricci Wavelet Transform. For the purpose of this invention the below-described method of decomposition, filter banks and algorithms utilized in these filter banks, may be implemented in software, embedded circuits (hardware) or firmware.

An Example of a Parallel Filter Bank

FIG. 1 is a block diagram of a parallel filter bank 100. FIGS. 1-4 describe a method of signal decomposition using filter bank 100 having a parallel arrangement of N filter sections that use the Parallel-Form Kovtun-Ricci Wavelet Transform. In some embodiments, parallel filter bank 100 is implemented in software, firmware, hardware, or combinations thereof. An original signal x 101 is applied to the input of the bank, and a set of N component signals $y_1 \ldots y_N$ 104 are provided at the outputs of the N filter sections (also called "component bands", or simply, "bands") of filter bank 100. In some embodiments, the filter sections are each comprised of a cascade of a component filter and a delay element, with the component filters having transfer functions denoted by $H_1 \ldots H_N$ 102, and the delay elements having transfer functions denoted by $D_1 \ldots D_N$ 103. The $p^{th}$ filter section 105 of filter bank 100, where $p=1 \ldots N$, is thus comprised of component filter $H_p$ 106 (one example of which is discussed further in the below-described FIG. 2) and delay element $D_p$ 107. Original input signal x 101 is provided at the inputs of all filter sections of filter bank 100, each of which produces corresponding component signal $y_p$ 108, $p=1 \ldots N$.

Component Filter

Figure 2:
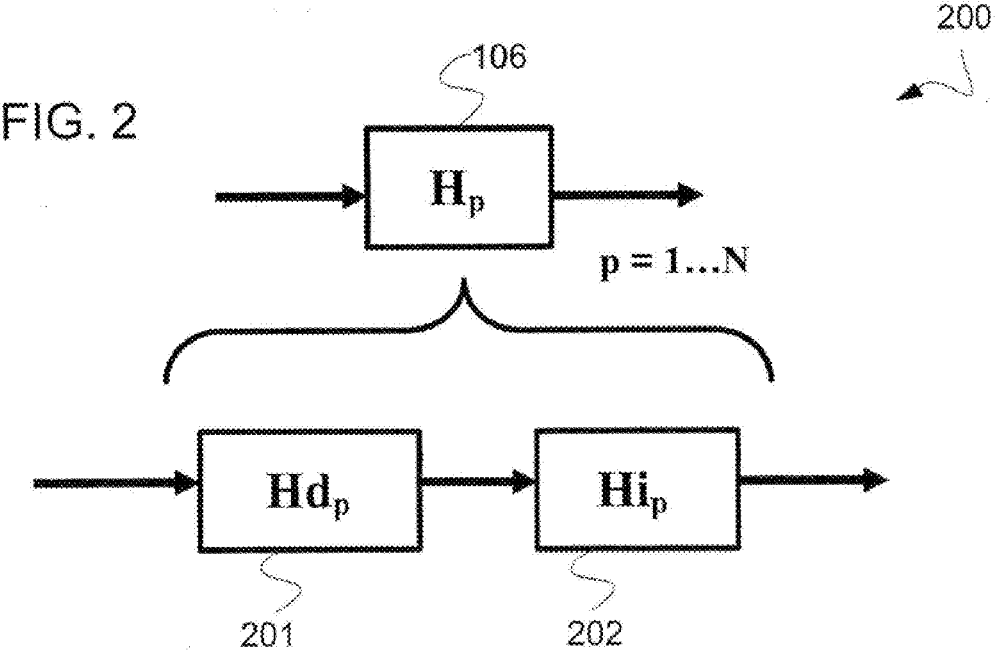
FIG. 2 is a block diagram 200 in exploded form illustrating the cascade construction of transfer function $H_p$ 106.

FIG. 2 is a block diagram 200 in exploded form illustrating one embodiment of a cascade construction of $H_p$ 106. In some embodiments, the invention provides a component filter transfer function for the $p^{th}$ component filter $H_p$ 106, $p=1 \ldots N$. Transfer function $H_p$ 106 is constructed from a cascade of two major blocks: a derivative kernel block $Hd_p$ 201 and an integrator kernel block $Hi_p$ 202.

Scaled Derivative Kernel Block

Figure 3:
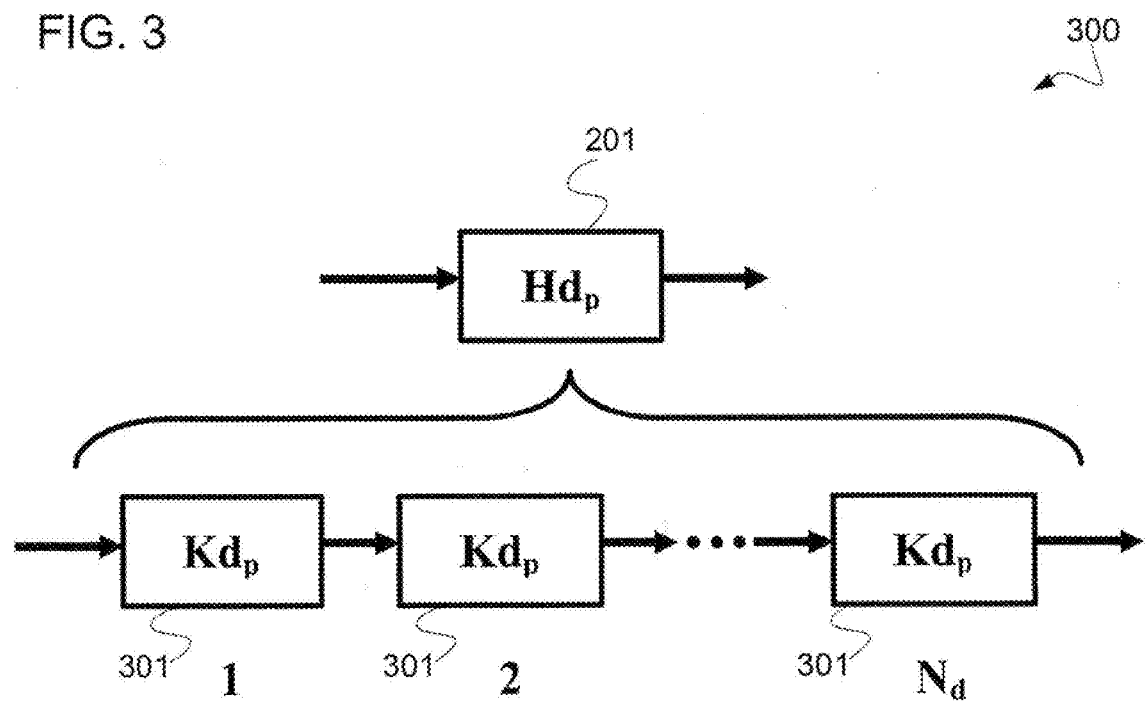
FIG. 3 is a block diagram 300, in exploded form, which shows derivative kernel block $Hd_p$ 201 as constructed from a cascade of $N_d$ basic derivative kernel blocks $Kd_p$ 301.

FIG. 3 is a block diagram 300 in exploded form of one embodiment that shows derivative kernel block $Hd_p$ 201 as constructed from a cascade of $N_d$ basic derivative kernel blocks $Kd_p$ 301. In the embodiment shown, a derivative kernel block $Hd_p$ 201 is constructed from a cascade of $N_d$ basic derivative kernel blocks $Kd_p$ 301 as shown. The transfer function $Kd_p$ 301 generally implements an approximation of the time derivative. The parameter p, while generally serving as an index to the $p^{th}$ component band (and thus the $p^{th}$ filter section), serves here also as an index to a predetermined scaling factor $k_p$ on the frequency scale of frequency response $Kd_p$ 301, and/or on the time scale of the impulse response $kd_p$ 301 of the basic derivative kernel. Frequency and/or time scaling, and its application and use, are generally understood and established in the art as per the theory of Wavelets, Wavelet Transforms, and Filter Banks for the purpose of tuning certain characteristics of each component filter in the bank, such as, for example, the center frequency and/or bandwidth of the resulting component filter. (See *The Fractional Fourier Transform, with Applications in Optics and Signal Processing*, by H. M. Ozaktas, Z. Zalevsky, and M. A. Kutay, Wiley, 2000; *Wavelets and Subband Coding*, M. Vetterli and J. Kovacevic, Prentice-Hall, 1995.)

An example embodiment of basic derivative kernel block $Kd_p$ 301 is given by the following discrete-time impulse response description:

$$kd_p(n) = (\delta(n) - \delta(n-k_p))/2$$

Here the normalization by the factor 2 is a choice for this example to provide a unity-gain passband, but may, in fact, be any arbitrary factor, and where there is defined the discrete-time delta function sometimes called the unit delta or unit impulse:

$$\delta(n) = \begin{cases} 1, & n = 0 \\ 0, & n \neq 0 \end{cases}$$

In some embodiments, $kd_p$ is comprised of, besides delay operations, the operations of signed addition and scaling by a factor of two, allowing for, in some embodiments, implementation using a multiplierless architecture. Specifically, it is well understood in the art of digital-signal-processing architectures, that scaling a signal sample by any integer power P of 2 may be readily implemented in digital form with appropriate shifting by P bits the digital bit representation of the signal sample. Thus, by extension through the cascade, scaled-derivative kernel block $Hd_p$ may itself, in some embodiments, be implemented using a multiplierless architecture. Further, it is worth noting that the time-domain impulse response $hd_p$ of scaled-derivative kernel block $Hd_p$ 201 has generally a bell-shaped envelope, particularly evident for $N_d$ greater than or equal to about 4, with alternating-sign coefficients. All nonzero coefficients of $hd_p$ have $(k_p-1)$ zeros interpolated between them. Even values of $N_d$ result in $hd_p$ symmetric about their time centers, while odd values of $N_d$ result in $hd_p$ antisymmetric about their time centers. The intrinsic delay of the impulse response $hd_p$, equivalent to the time delay to the time center of $hd_p$, is $Dd_p=N_d k_p/2$ samples and this delay is integer-valued for $N_d$ and/or $k_p$ even. The z-domain transfer function of the scaled-derivative kernel block is:

$$Hd_p(z) = \left[\frac{1-z^{-k_p}}{2}\right]^{N_d}$$

where, when evaluated on the unit circle ($z=e^{j\omega}$), the frequency response is:

$$Hd_p(\omega) = \left[\frac{1-e^{-j\omega k_p}}{2}\right]^{N_d}$$

The frequency response $Hd_p(\omega)$ exhibits a series of substantially bell-shaped passbands, particularly for $N_d$ greater than or equal to about 4, centered at $\omega_{pq}=\pi(1+2q)/k_p$ radians, or $f_{pq}=Fs(1+2q)/(2k_p)$ Hz, where Fs is the sample rate in Hz, and where $q=0,1,2,\ldots$, such that the $q=0$ case corresponds to the fundamental passband centered at $\omega_{p0}\equiv\omega_p$ ($f_{p0}\equiv f_p$). The passbands have bandwidths that are inversely proportional to $k_p$ and monotonically inversely related to $N_d$. In the fundamental passband, the frequency response has constant ("flat") phase equal to $N_d \pi/2$, after accounting for the linear phase term due to the intrinsic delay $Dd_p$.

Scaled Integral Kernel Block

Figure 4:
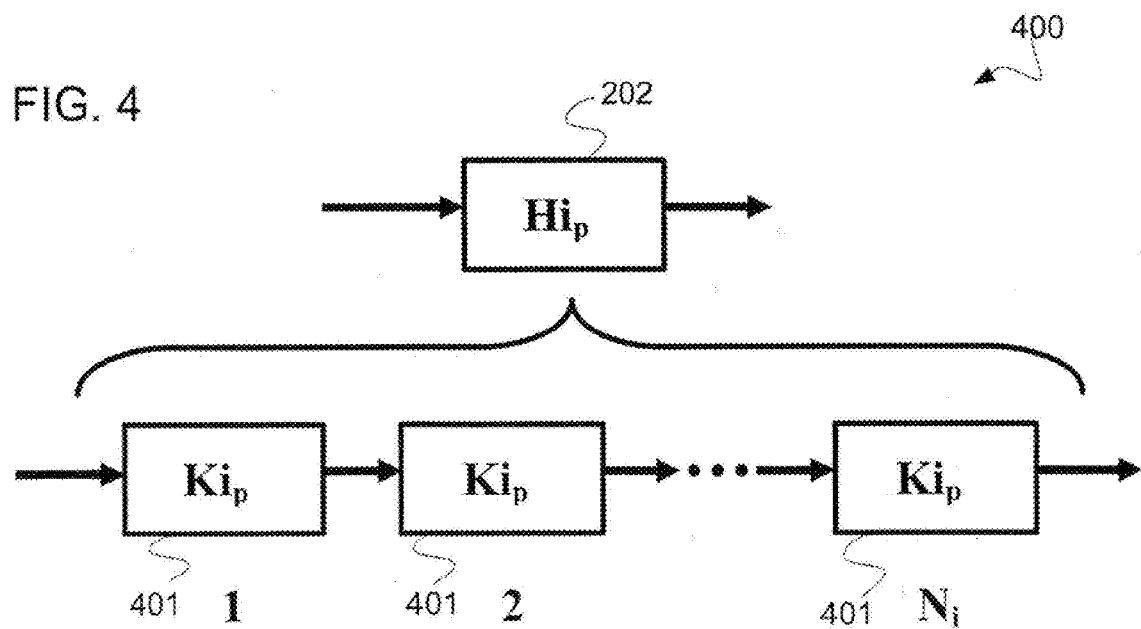
FIG. 4 is a block diagram 400, in exploded form, which shows integrator kernel block $Hi_p$ 202 as constructed from a cascade of $N_i$ basic integrator kernel blocks $Ki_p$ 401.

FIG. 4 is a block diagram 400 in exploded form that shows integrator kernel block $Hi_p$ 202 as constructed from a cascade of $N_i$ basic integrator kernel blocks $Ki_p$ 401. In this embodiment, integrator kernel block $Hi_p$ 202 is constructed from a cascade of $N_i$ basic integrator kernel blocks $Ki_p$ 401. The transfer function $Ki_p$ 401 generally implements an approximation of the local time integral (i.e., the time integral over a local interval of time). The parameter p, while generally serving as an index to the pth component band, serves here also as an index to a predetermined scaling factor $w_p$ on the frequency scale of frequency response $Ki_p$ 401 and/or on the time scale of the impulse response $ki_p$ of the basic integrator kernel, where frequency and/or time scaling is generally understood as before with regard to the above derivative kernel. An example embodiment of block $Ki_p$ 401 is given by the following discrete-time impulse response description:

$ki_p(n)=(u(n)-u(n-w_p))/w_p$ where the normalization by the factor $w_p$ is a choice for this example to provide a unity-gain passband, but may in fact be any arbitrary factor, and where there is defined the discrete-time unit step function:

$$u(n) = \begin{cases} 1, & n \geq 0 \\ 0, & n < 0 \end{cases}$$

In some embodiments, $ki_p$ is comprised of, besides delay operations, the operations of signed addition and scaling by a factor of $w_p$. In still other embodiments, choosing $w_p$ as an integer power of 2 allows for implementation of $ki_p$ using a multiplierless architecture, and by extension through the cascade, allows scaled-integral kernel block $hi_p$ to be implemented using a multiplierless architecture.

In some embodiments, the time-domain impulse response of basic integrator-kernel block $ki_p$ is rectangular in shape, with a width of $w_p$ samples and with height $w_p^{-1}$, so that the gain at dc of this block, the sum of the coefficients, is unity. One may further note that, in some embodiments, the time-domain impulse response $hi_p$ of scaled-integrator kernel block $Hi_p$ 202 is generally bell-shaped, particularly evident for $N_i$ greater than or equal to about 3. In practice, in some embodiments, $w_p$ is set to a value of at least 2 samples, since both $w_p=0$ and $w_p=1$ are degenerate cases resulting in all-zero coefficients and a unit impulse for $hi_p$, respectively, regardless of $N_i$. In some embodiments, impulse responses $hi_p$ are symmetric about their time center regardless of $N_i$ or $w_p$. The intrinsic delay of the impulse response $hi_p$, equivalent to the time delay to the time center of $hi_p$, is $Di_p=N_i(w_p-1)/2$ samples and this delay is integer-valued for $N_i$ even and/or $w_p$ odd. The z-domain transfer function of the scaled-integral kernel block is:

$$Hi_p(z) = \left[\frac{1-z^{-w_p}}{w_p(1-z^{-1})}\right]^{N_i}$$

where, when evaluated on the unit circle ($z=e^{j\omega}$), the frequency response is:

$$Hi_p(\omega) = \left[\frac{1-e^{-j\omega w_p}}{w_p(1-e^{-j\omega})}\right]^{N_i} = \left[\frac{\sin(\omega w_p/2)}{w_p \sin(\omega/2)}\right]^{N_i} e^{-j\omega N_i(w_p-1)/2}$$

In some embodiments, the amplitude of $Hi_p(\omega)$ exhibits a classic periodic-sinc shaped lowpass response having a mainlobe centered at dc($\omega=0$) with a peak amplitude of unity, sidelobes of generally decreasing amplitude towards Nyquist ($\omega=\pi$), and amplitude zeros (nulls) at $\omega_p=2\pi \cdot r/w_p$ radians, or $f_p=Fs \cdot r/w_p$ Hz, where Fs is the sample rate in Hz, and where $r=1,2,\ldots N$. The lowpass mainlobe passband has bandwidth inversely proportional to $w_p$ and monotonically inversely related to $N_i$. With increasing $N_i$ the sidelobes become progressively more attenuated and the overall amplitude response becomes progressively more bell-shaped. The phase response of $Hi_p(\omega)$, after accounting for the linear phase term due to the intrinsic delay $Di_p$, is flat and equal to zero radians in the lowpass mainlobe, and continues to be flat in the sidelobes, alternating between 0 and $\pi$ radians every other sidelobe for odd values of $N_i$ (i.e., the phase is flat and zero radians everywhere for even values of $N_i$).

Application of $Hd_p$ and $Hi_p$ to $H_p$

In some embodiments, component filter $H_p$ 106 is composed of the cascade of scaled-derivative kernel block $Hd_p$ 201 and scaled-integral kernel block $Hi_p$ 202, and the frequency response of component filter $H_p$ 106 is the product of the frequency responses of $Hd_p$ 201 and $Hi_p$ 202. In practice, the band-tuning parameters $k_p$ and $N_d$ of $Hd_p$ 201 are tuned to set the center frequency and bandwidth of the fundamental passband, and by consequence, the harmonic passbands, of component filter $H_p$ 106. In some embodiments, the band-tuning parameters $w_p$ and $N_i$ of $Hi_p$ 202 are tuned to set the degree of suppression needed, if any, in the harmonic passbands. This is typically accomplished by disposing the width of the mainlobe of $Hi_p$ 202 so that it covers the fundamental passband of $Hd_p$ 201, along with the desired number of successive harmonic passbands, if any, and so that the undesired harmonic passbands reside in the region of the nulls and sidelobes of $Hi_p$ 202. If no harmonic suppression is needed, the block $Hi_p$ 202 may be eliminated, or equivalently, replaced with a unit impulse (e.g., by setting $w_p=1$).

In some embodiments, only the fundamental passband is kept, and all harmonic passbands are suppressed without loss of generality (WLOG). In some embodiments, a degree of optimality in overall harmonic suppression may be obtained by placing the first null of $Hi_p$ 202 as close as possible to the peak of the first harmonic passband. In some embodiments, the relation:

$$w_p = Q[\tfrac{2}{3} k_p]$$

where the operator $Q[x]$ quantizes x to an integer, satisfies this constraint. The operator $Q[\cdot]$ may take the form of the ceiling, floor, or rounding operation, and, in some embodiments, in order to satisfy the requirements of a multiplierless architecture, may be made to round to the nearest integer power of 2.

Complete Parallel Filter Bank

In some embodiments, the family of component filters $H_p$ 106, $p=1 \ldots N$ forms a class of wavelets. The degree of orthogonality among the various wavelet scales may be controlled in the frequency domain by determination of the degree of overlap between band responses. Overlap may be reduced by increasing the frequency spacing between the associated passbands, and/or by increasing $N_d$, and/or by generally suppressing harmonic passbands. Note that in the above examples, the band-tuning parameters $k_p$, $N_d$, $w_p$, and $N_i$ were implicitly held constant with respect to band index p. These band-tuning parameters may, in fact, be made individually tunable band-by-band, for example in order to optimize orthogonality in a particular filter bank implementation. One may now define the values of delay $m_p$ for the delay blocks $D_p$ 107, $p=1 \ldots N$ in the parallel filter bank 100 of FIG. 1. Typically, a delay block $D_p$ 107 is used to compensate for intrinsic delays in component filter $H_p$ 106 with respect to the remaining of such set of blocks. One may note that the intrinsic delay of component filter $H_p$ 106 is $Dd_p + Di_p$ and is generally different for every component band. Some systems may accommodate this relative delay by accounting for each known delay $Dd_p + Di_p$, for example in the values of the object timestamps in the context of the current invention. Other systems may require the real-time output of each component band to be aligned in time. For such systems, the delay of each delay block $D_p$ 107 should be set such that the intrinsic delays from x to each $y_p$ 108 in the bank are substantially the same for all $p=1 \ldots N$. In some embodiments, this time alignment may be accomplished with minimum overall delay by having:

$$m_N = 0$$

$$m_p = (Dd_n + Di_n) - (Dd_p + Di_p), p=1 \ldots N-1$$

where delay block $D_p$ 107 is implemented with impulse response:

$$d_p(n) = \delta(n - m_p)$$

Example Cascade Filter Bank

Figure 5:
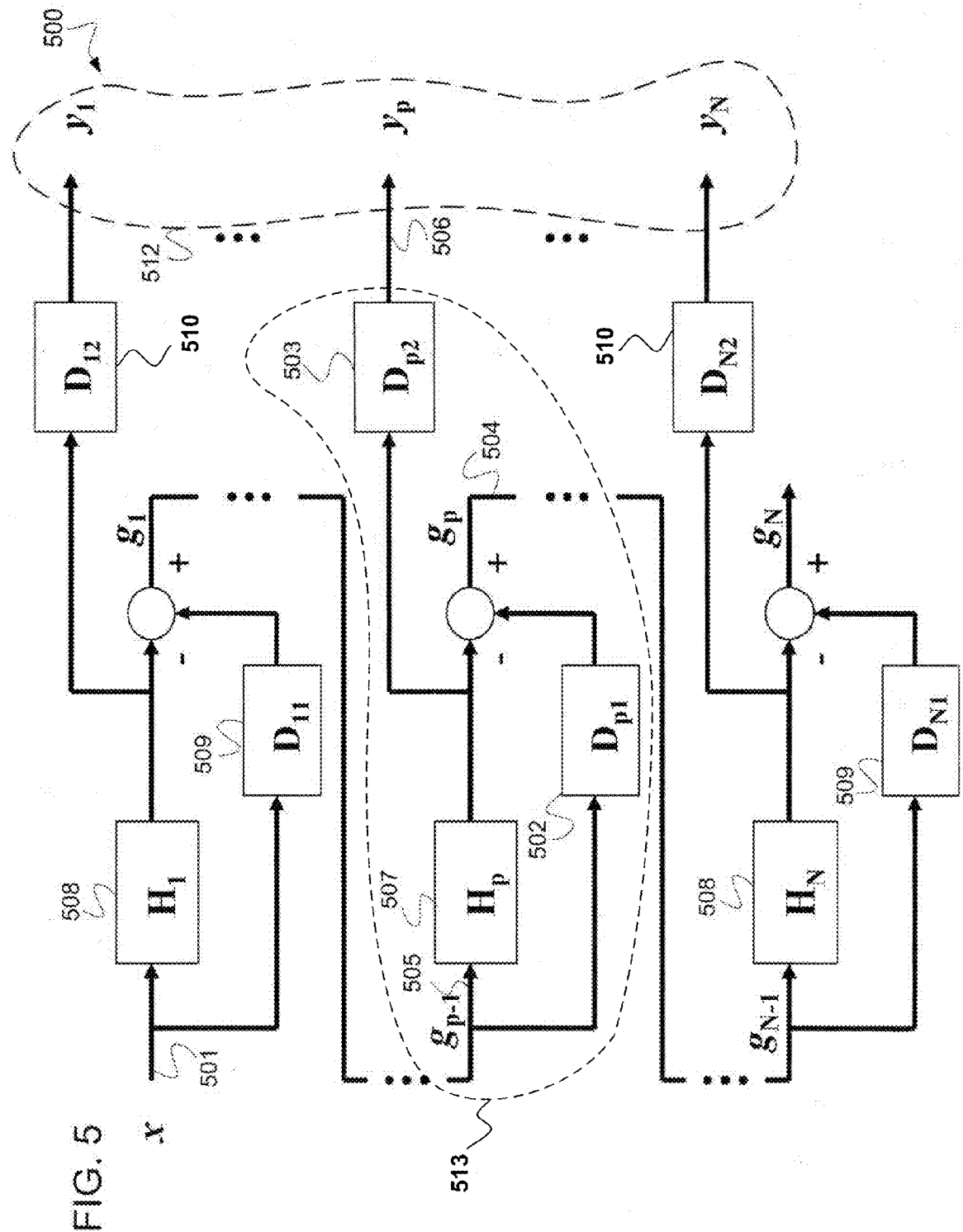
FIG. 5 is a block diagram of a cascade filter bank 500.

FIG. 5 is a block diagram of an exemplary cascade filter bank 500 of some embodiments. This illustrates an example method of decompositions of some embodiments of the present invention in the form of filter banks, using a bank of filter sections disposed in cascade form. An original signal x 501 is applied to the input of the filter bank 500, and a set of N component signals $y_1 \ldots y_N$ 512 are provided at the outputs of the N filter sections in filter bank 500. In some embodiments, the filter sections are each comprised of a network of component filters and two delay elements, with the component filters having transfer functions denoted by $H_1 \ldots H_N$ 508, the first delay elements having transfer functions denoted by $D_{11} \ldots D_{N1}$ 509, and the second delay elements having transfer functions denoted by $D_{12} \ldots D_{N2}$ 510. The $p^{th}$ filter section 513 of filter bank 500, where $p=1 \ldots N$, is thus comprised of component filter $H_p$ 507, first delay element $D_{p1}$ 502, and second delay element $D_{p2}$ 503.

In some embodiments, the input to the $p^{th}$ filter section in the bank is applied to the inputs of both block $H_p$ 507 and first delay block $D_{p1}$ 502. In some embodiments, the output of $H_p$ 507 is applied to the input of second delay block $D_{p2}$ 503, forming $p^{th}$ component output $y_p$ 506. In some embodiments, the output of $H_p$ 507 is also subtracted from the output of $D_{p1}$ 502, forming $p^{th}$ signal $g_p$ 504, called a "residual" or "feed-forward" output signal associated with the $p^{th}$ band. The filter sections are then connected such that the input to the $p^{th}$ filter section is $g_{p-1}$ 505, (i.e., the residual output signal of the previous band, for $p=2 \ldots N$). For $p=1$, the input of the filter section is the input signal x 501. Hence, in some embodiments, the filter bank features a cascade topology.

In some embodiments, the component filters $H_p$ 507 may be implemented according to the description of the $H_p$ 106 corresponding to the above example parallel filter bank of this invention, with the condition that the coefficients of $H_p$ 507 be normalized so that the corresponding frequency response magnitude peaks are unity, and with the condition that $H_p$ 507 exhibit zero phase in the fundamental passband (after accounting for the linear phase term due to the intrinsic delay of $H_p$ 507). The zero-phase condition may be met by having $N_d$ be a multiple of four, or an appropriate multiple of two with corresponding polarity adjustment of the coefficients for zero phase in the passband of interest. In some embodiments, delay block $D_{p1}$ 502 would be preferably assigned delay value $m_{p1} = Dd_p + Di_p$ as per $H_p$ 106, and specifically the intrinsic delay of block $H_p$ 507, where delay block $D_{p1}$ 502 is implemented with impulse response:

$$d_{p1}(n) = \delta(n - m_{p1})$$

With regard to the $p^{th}$ transfer function $Tg_p$ defined from $g_{p-1}$ to $g_p$, the time alignment between delay element $D_{p1}$ 502 and component filter $H_p$ 507 produces cancellation in the frequency response of $Tg_p$ at the frequency-response-magnitude peaks of $H_p$ 507 having zero phase (e.g., the fundamental passband peak). As such, the residual output signal $g_p$ contains the information of residual output signal $g_{p-1}$, except with the significant frequency content (if any) associated with component filter $H_p$ 507 having been substantially removed. (In this sense, original signal x 501 may be considered as residual $g_0$, as it has had no information removed.) With regard to the $p^{th}$ transfer function $Ty_p$ defined from input x 501 to output $y_p$ 506, this arrangement of cascaded residual output signals results in a set of transfer functions $Ty_p$, where p=1 ... N, that are mutually approximately orthogonal.

In some embodiments, by choosing the wavelet scale factors $k_p$ so that they are monotonically decreasing with increasing p, the residuals $g_p$ and the transfer functions $Ty_p$ become progressively more lowpass (i.e., have progressively less high-frequency content) due to the information-removal property of cascade filter bank 500 as discussed above. This has the effect of suppressing harmonic passbands present in the derivative kernel block $Hd_p$, reducing or eliminating the need for the harmonic suppression from the scaled integrator kernel $Hi_p$ in component filter $H_p$ 507. In some embodiments, the final residual output signal $g_N$ would thus contain substantially lowpass-only, near-dc information, such as baseline artifacts, and particularly no periodic or qp information, and so would not be used for creation of objects in the context of this invention. The lowpass residual output may, however, be useful for general signal processing tasks and so is left as part of this invention. One may now define the values of delay $m_{p2}$ for the second delay elements $D_{p2}$ 503, p=1 ... N, in cascade filter bank 500 of FIG. 5. With regard to $p^{th}$ transfer function $Ta_p$, defined from input x 501 to the input of second delay element $D_{p2}$ 503 for p=1 ... N, delay block $D_{p2}$ 503 may be used to compensate for intrinsic delays in $Ta_p$ with respect to the remaining of such set of transfer functions. One may note that the intrinsic delay $Da_p$ of transfer function $Ta_p$ is:

$$Da_p = \sum_{s=1}^{p} D_{s1}, \quad p = 1 \ldots N$$

and is generally different for every component filter. As with the parallel filter bank 100 of FIG. 1, some systems may accommodate this relative delay by accounting for each known delay $Da_p$, for example in the values of the object timestamps in the context of the current invention. Other systems may require the real-time output of each component band to be aligned in time. For such systems, the delay of each second delay element $D_{p2}$ 503 should be set such that the intrinsic delays from original signal x 501 to each component signal $y_p$ 506 in filter bank 500 are substantially the same for all p=1 ... N. In some embodiments, this time alignment may be accomplished with minimum overall delay by having:

$$m_{N2} = 0$$

$$m_{p2} = \sum_{s=p+1}^{N} D_{s1}, \quad p = 1 \ldots N-1$$

where delay block $D_{p2}$ 503 is implemented with impulse response:

$$d_{p2}(n) = \delta(n - m_{p2})$$

An important property of the cascade filter bank is that the original signal x 501 is perfectly recovered from the sum of the outputs and the final lowpass residual, that is:

$$\sum_{p=1}^{N} y_p(n) + g_N(n) = x(n)$$

Partial sums of outputs over a subset of p=1 ... N may also be used to define wider bands from a combination of narrower ones ("composite bands"), and linear combinations of the outputs of narrower bands may more generally be used to define composite bands of arbitrary shape, for example using the band centers of each transfer function $Ty_p$ to approximately define a value of frequency-domain magnitude.

Analytic Filter Banks

FIG. 6 is a block diagram of a section 600 of an analytic filter bank that can employ any of the block arrangements described above. In the example shown in FIG. 6, the output of $p^{th}$ filter section, i.e., component signal $y_p$ 601, is processed to produce a substantial approximation of a corresponding analytic component signal having a real part $y^{re}_p$ 604 and an imaginary part $y^{im}_p$ 603. In some embodiments, the component signal $y_p$ 601 output from the corresponding $p^{th}$ filter section, is processed through a Hilbert transformer block $Hh_p$ 602 to produce a substantial approximation of the imaginary part of the analytic component signal $y^{im}_p$ 603. In other embodiments, a basic derivative kernel block $Kd_p$ 301 (as per FIG. 3) may be used as a particular implementation for Hilbert transformer block $Hh_p$ 602 to produce a substantial approximation of the imaginary part $y^{im}_p$ 603 of the analytic component signal.

In some embodiments, the component signal $y_p$ 601 of the corresponding of $p^{th}$ filter section, is processed through a delay element $Dh_p$ 605 to form the real part of the analytic component signal $y^{re}_p$ 604. In some embodiments, delay element $Dh_p$ 605 is set for a delay substantially equal to the intrinsic delay $mh_p$ of Hilbert transformer block $Hh_p$ 602 over at least the bandwidth of interest for the $p^{th}$ component. This is useful for systems requiring the intrinsic delay from $y_p$ 601 to real part $y^{re}_p$ 604 to be the same as that from $y_p$ 601 to imaginary part $y^{im}_p$ 603. In some embodiments delay element $Dh_p$ 605 is implemented with the following impulse response:

$$dh_p(n) = \delta(n - mh_p)$$

In some embodiments, basic derivative kernel block $Kd_p$ 301 is used for Hilbert transformer block $Hh_p$ 602. In this case, the delay of block $Dh_p$ 605 may be set with $mh_p = k_p/2$, equivalent to the intrinsic delay of the basic derivative kernel block $Kd_p$ 301. This delay is integer-valued for $k_p$ even.

The outputs of $p^{th}$ analytic filter bank 600 may then be used to form the $p^{th}$ complex analytic signal:

$$y^c_p = y^{re}_p + j y^{im}_p$$

such that $y^c_p$ may be generally applied for spectral analysis, instantaneous frequency and amplitude measurement, and related applications well understood and established in the art of analytic signals and communications systems. In particular, regarding the current invention context, in some embodiments, the analytic component signals may be used for defining quarter-phase or fractional-phase objects and attributes. With regard to the $p^{th}$ transfer function $Ty_p$ defined from input x to output $y_p$ 601 of any of the above filter banks, $Ty_p$ may thus be extended using this example arrangement to analytic transfer functions $Ty^{re}_p$, $Ty^{im}_p$ and $Ty^c_p$, and applied as analytic filters in either the time or frequency domain, again as well understood and established in the art.

In some embodiments the intrinsic delay $mh_p$ from component signal $Y_p$ 601 to imaginary part $y^{im}_p$ 603 may depend upon the scale (indexed by p), particularly for Hilbert-transformer block $Hh_p$ 602 implemented in real-time form using basic derivative kernel block $Kd_p$ 301. In such cases, the intrinsic delay of transfer function $Ty^{im}_p$ (and by extension, where applicable, that of $Ty^{re}_p$) would be additively increased over the intrinsic delay of transfer function $Ty_p$ by the delay $mh_p$. As with the above filter bank examples, some systems may accommodate the relative delay of the various real and imaginary signal paths of the various bands of the analytic filter bank by accounting for each known delay, for example in the values of the object timestamps in the context of the current invention. Some systems may require the real-time output of each analytic component band to be aligned in time. As is well known, for such systems, the delay of each delay block for each component band may be adjusted so that the intrinsic delay from original signal x to each real party $y^{re}_p$ and imaginary part $y^{im}_p$ in the analytic bank are substantially the same for all p=1 . . . N. (See *Discrete-Time Signal Processing*, by A. V. Oppenheim, R. W. Schafer, and J. R. Buck, Prentice-Hall, 1999.) This may be accomplished in the above examples with minimum overall delay by adding the delay adjustment terms:

$$m_{N3}=0$$

$$m_{p3}=mh_N-mh_p, p=1\ldots N-1$$

to the respective delay terms $m_p$, p=1 . . . N for the parallel bank, or respectively to $m_{p2}$, p=1 . . . N for the cascade bank.

The above described development of the filter bank examples does not strictly mention the notions of completeness, including overcompleteness and/or undercompleteness, and sampling, including over sampling and/or sub-sampling, as understood and established in the sense of wavelet transform considerations. With regard to completeness, in some embodiments, decomposition need only substantially represent and/or support the components in the signal that are meaningful to its representation in the sense that the objects produced correspond to desirable feature points on the original signal morphology. In the case of reconstruction of an estimate of the original signal from objects, meaningful components may be those in which the reconstruction substantially represents the original signal morphology to some predetermined degree of accuracy, such as, for example, clinical equivalence for diagnosis by a physician in the ECG example, or as a more general example, some predetermined maximum allowable amount of mean-square error. Thus, undercomplete transforms as well as overcomplete transforms may be readily accommodated in some embodiments.

With regard to sampling, some embodiments of the wavelet transform sub-sample (i.e., they decimate) the individual inputs and/or outputs of the component bands, taking advantage of the fact that the component signals and band filters may carry significantly less information content than the original signal. The resulting sub-sampled filter bank is also called a multirate filter bank. Systems that do not sub-sample are also called oversampled systems. The current invention may be considered a multirate filter bank, in the sense that the fractional-phase objects are sub-samples of their corresponding component signals. However, in this case the sample timings of objects depend on characteristics of the component signals and not simply upon some proportion of the sample period of the original signal. In some embodiments, sub-sampling of one or more of the component bands may take place. In addition, the sub-sampled component signals may be carried forward in the processing system in place of and/or in addition to the non-sub-sampled component signals. In some embodiments, objects based upon such sub-sampled component signals may be formed. One may present an example filter bank employing a single sample rate throughout (i.e., an oversampled filter bank) WLOG.

As to reconstruction, sub-sampled systems rely on interpolation to reconstruct the component signal at the original sample rate, typically using zero-interpolation by the corresponding decimation factor, and then filtering the zero-interpolated result using a resynthesis filter is, in some embodiments, defined according to well-established wavelet transform methods. In some embodiments, interpolation and resynthesis may be employed, utilizing the object stream from each component to define impulses, or narrow interpolation kernels, on the original sampling grid. In some embodiments, each impulse would be weighted by its corresponding object amplitude, and centered at the time of the corresponding component peak. Overlap between interpolation kernels, if any, would be summed, sample by sample. The remaining samples would be set to zero. The resulting sequence would then be passed through a reconstruction filter for the corresponding component band, thereby reconstructing the component signal.

In the sense that completeness and sampling fit into the context of a frame in the wavelet transform, frames of any width and height in the time-frequency plane may thus be considered as part of this invention, provided that they meet the criteria given in this invention for signal representation and/or reconstruction.

Example Objects, Data Structures, Quarter-Phase Representation, and Systems and Methods for Implementing The output of decomposition is generally a set of component signals having a simple morphology, substantially resembling sine waves, though not necessarily purely sinusoidal. In some embodiments, the various component filters outlined above will be excited to a varying degree by underlying components in the signal that correlate to the impulse response shape of the corresponding component filter, producing a component output (e.g., $y_p$ 108, $y_p$ 506) that is active. The relative amplitude of an active component will be affected by the degree of correlation and the overall strength of the signal. The states of active or inactive may be discriminated according to amplitude of the component, for example, comparing it to a fixed threshold or adaptive threshold based upon the total time-local energy of the signal.

Some embodiments provide a method to discretely quantify meaningful events in active components, in that these events tend to exhibit strong correspondence to desired feature points along the original signal. Active component signals should generally exhibit regular undulations with readily distinguishable cycles and corresponding cycle features.

FIG. 7A is a waveform 700 illustrating a cycle from one component signal that is broken up into four quarter-phases. This shows an example of a method whereby a cycle from one component signal is broken up into four quarter-phases, labeled as A, B, C, and D. This component signal is broken up into and, in some embodiments, defined according to certain unique features such as the positive-going and negative-going zero crossings, and the positive and negative peaks of the component signal. These unique features are shown in a table format in FIG. 7B.

FIG. 7B is a table 751 illustrating the various unique features such as the positive-going and negative-going zero crossings, and the positive and negative peaks of the component signal that are analyzed by the invention In practice, these unique features such as the zero crossings may be readily detected by a change in sign of the signal, while the peaks may be detected by any of various means well known and established in the art, including a corresponding change in sign of the derivative of the signal. Alternatively, in some embodiments, given the availability of analytic signal components, the positive-going and negative-going zero crossings of the imaginary part of the component signal are used to represent the positive and negative peaks of the real part and vice versa. The feature points bound the four quarter-phases and therefore define the transitions of the component signal between and among the four quarter-phases A, B, C, and D. In some embodiments, the component signal is defined as being "in" a particular quarter-phase at any point in time that the component signal satisfies the starting and ending criteria for that quarter-phase. Under those conditions the quarter-phase is defined as "active" for the corresponding component.

These unique features, quarter-phase transitions of the component signals tend to correspond strongly to points of interest (i.e., feature points) along the original signal, such as, for example, local peaks, valleys, inflections, curves, and changes of shape. In some embodiments, this property is utilized for various types of robust analysis. One example application of this property is that of robust delineation (or segmentation) of an ECG waveform into the various waves (e.g., P, Q, R, S, T, U, etc.) and segments between these waves, along with the various applications of such delineation. This property can be utilized in the analysis of most any qp waveform.

FIG. 7C describes how four quarter-phases (i.e., Nos. 701, 702, 703, 704) of waveform 700 may be characterized simply using two parameters. First, the time duration T4 (i.e., Nos. 705A, 705B, 705C, 705D) of a quarter-phase is the length of time from the beginning to the end of the quarter-phase (i.e., the time between consecutive quarter-phase transitions of the component signal). Second, the amplitude a (i.e., Nos. 706A, 706B, 706C, 706D) of a quarter-phase is a measure of the vertical deviation of the quarter-phase over its course. The amplitude of the quarter-phase is the absolute value of the peak (i.e., the maximum absolute value) of the component signal over the course of the quarter-phase. For quarter-phases A and C, this value is obtained at the end of the quarter-phase, while for quarter-phases B and D, this value is obtained at the beginning of the quarter-phase. Alternately, in some embodiments, this amplitude may be any amplitude measure well known and established in the art, including the mean absolute value or the root-mean-square value of the component signal taken over the time duration T4 of the quarter-phase, or a local measure of the magnitude of the analytic signal for that component.

In some embodiments, by following the quarter-phase structure, the imaginary part of the analytic signal for a component may be approximated at any given point by evaluating that component signal at a time T4 to either side from that point. The value used for T4 in this evaluation may be the most recent value for that component, or it may be a constant derived from a quarter of the period at the center frequency of the component band.

In some embodiments, T4 may itself be estimated by taking the time between that last two zero-crossings or, if appropriate, the current and prior zero crossings and dividing that value by two.

In some embodiments, these parameters (L, a, T4) are collected, where L is the label of the quarter-phase (i.e., one of A, B, C, or D), and this collection is referred to as a "quarter-phase object" (or "object") $O_{ij}$ occurring at the $i^{th}$ time index for the $j^{th}$ component. A corresponding notation for the continuous-time case would be $O_j(t)$, where t is continuous time. This object representation therefore creates a compact packet of concentrated information about the component signal and hence, the original signal, precisely tied to a point of interest along the original signal.

In some embodiments, these quarter-phase objects will then be represented as structures or objects in a computer program. In some embodiments, these objects will have data attributes that correspond to the parameters (L, a, T4). The representation of data through the use of objects is well known in the arts of software engineering and computer science. (See *Data Structures and Other Objects Using C++ 2$^{nd}$ Edition*, by M. Main and W. Savitch, Addison-Wesley, 2001.) The use of the term object implies a meaning as understood by these arts.

In some embodiments, the absolute timing of an object (i.e., the time of occurrence of the object) may be referenced to the beginning time or ending time of its associated quarter-phase. However, in a given system implementation one reference should be chosen and used consistently throughout.

In still other embodiments, over the course of a typical component signal, a stream of such objects will be generated, which may be stored, transmitted, and/or analyzed. The index i may be indexed according to some underlying constant sample rate, in which case i may be considered as a form of time-stamp for the generated object. In some embodiments, index i would be incremented upon generation of each corresponding object. In this case, the absolute time of occurrence for a particular $O_{ij}$ may be stored along with the object, or it may be reconstructed by summing the values T4 for that component from some arbitrary reference time.

In some embodiments, the values T4 may be measured, if necessary, with arbitrary resolution using interpolation methods to determine the zero crossings and/or peaks of the component signals. Interpolation methods to accomplish this are well known and established in the art, including methods such as polynomial fitting and cubic splines in a neighborhood of the zero crossing of the curve or a zero crossing of the derivative of the curve.

Also depicted in FIG. 7C is the inherent symmetry of the quarter-phase representation along the amplitude and time axes. This symmetry is utilized in the signal-compression signal concentration aspect of the invention. In some embodiments, it can be noted that for a given cycle, the simple amplitude measure is the same for quarter-phases A and B, and for quarter-phases C and D. This offers some further compactness of information in the object representation, in that the value of a need only to be evaluated once for the A-B transition, and once for the C-D transition.

While the component signal in FIG. 7A appears to be sinusoidal, the component signal only need be roughly sinusoidal, to the extent that the quarter-phases may be identified unambiguously. In some embodiments, a component signal whose unwrapped analytic phase is roughly monotonic over time would be a reasonable candidate for this method.

Figures 7D, 7E:
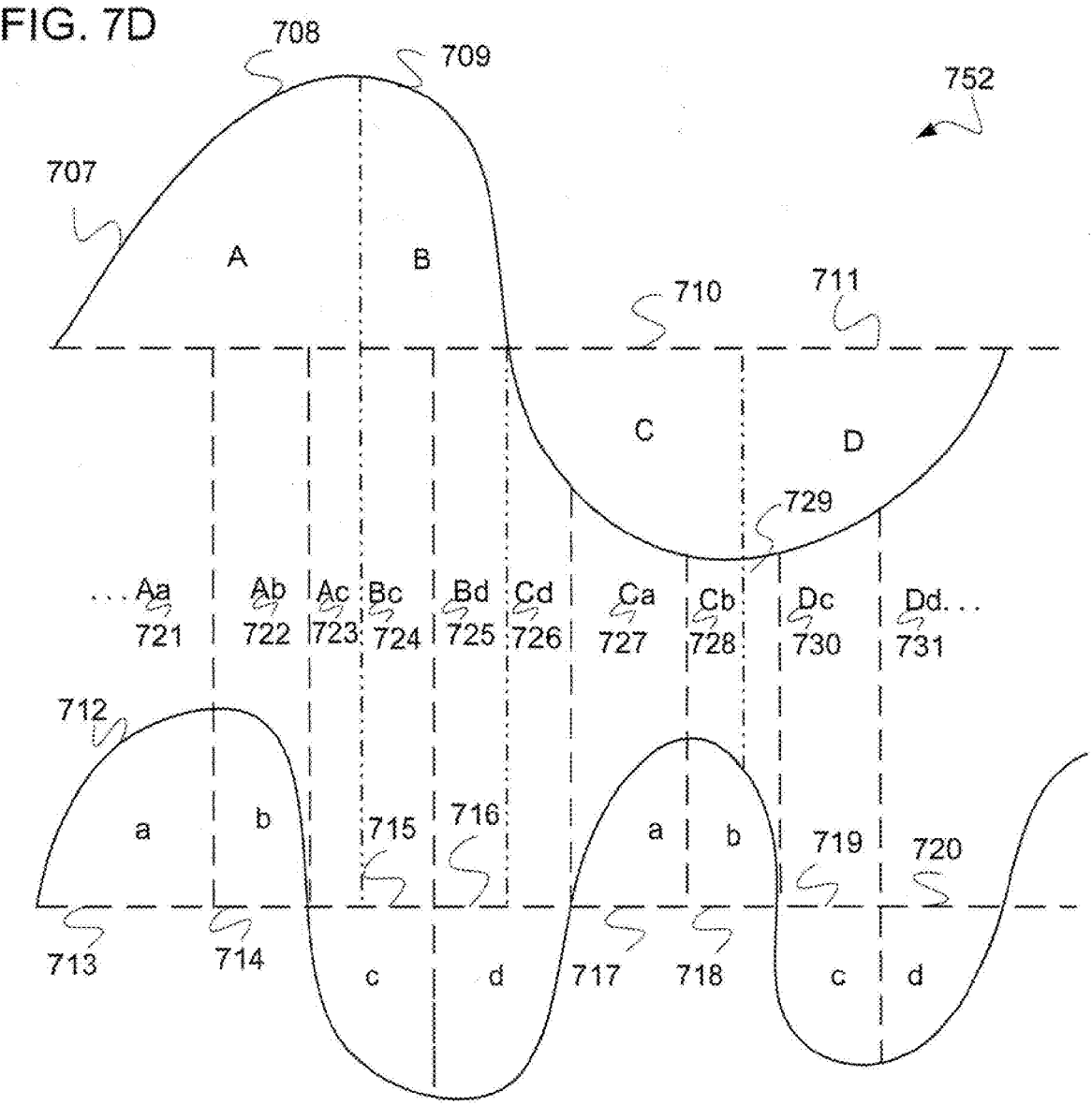
FIG. 7D shows a method 752 for breaking up into quarter-phases the cycles of two component signals, the time ranges over which the phase labels are coincidently stable (quarter-phases are active), and the states defined by vectors of those labels, indicated here with labels Aa, Ab, Ac, Bc, Bd, Cd, Ca, Cb, Db, Dc, Dd, etc.
FIG. 7E is a matrix 753 containing the sixteen possible quarter-phase regions (states) of a method 700, for two component waves.

FIG. 7D shows a method 752 for breaking up into quarter-phases the cycles of two component signals, the time ranges over which the phase labels are coincidently stable (quarter-phases are active), and the states defined by vectors of those labels, indicated here with labels Aa, Ab, Ac, Bc, Bd, Cd, Ca, Cb, Db, Dc, Dd, etc. In some embodiments, method 752 processes two component waves including a lower-frequency component wave 707, and a higher-frequency component wave 712. The lower-frequency component wave 707 includes, in some embodiments, of quarter-phases A 708, B 709, C 710, and D 711. Similarly, in some embodiments, the higher-frequency component wave 712 includes quarter-phases a 713 and b 714, c 715, d 716, with the cycle repeating to a 717, b 718, c 719 and d 720. Also depicted in FIG. 7D are active states referenced by various state labels. For example, state label Aa 721 refers to the active state corresponding to a portion of the lower-frequency component wave 707, and higher-frequency component wave 712. Similarly, Ab 722, Ac 723, Bc 724, Bd 725, Cd 726, Ca 727, Cb 728, Db 729 (depicted but not labeled), Dc 730, and Dd 731 all depict various active states corresponding to portions of waves 707 and 712. In some embodiments, these active states continue so long as there is a signal to be processed.

In some embodiments, the four points of transition between quarter-phases also correspond to the quarter-wave points along the forward transition of the analytic phase of the component (i.e., where the analytic phase substantially equals 0, 90, 180 and 270 degrees, or 0, $\pi/2$, $\pi$, and $3\pi/2$ radians, respectively). From this perspective, further wave subdivisions are possible, say, defining fractional-phase regions bounded by N fractional phase increments $n\pi/N$, $n=0,1 \ldots N-1$ along with their associated objects, labels and parameters. In some embodiments, using N=16, quarter-phase A could be subdivided into four fractional-phase regions A1, A2, A3, and A4, and likewise for quarter-phases B, C, and D, resulting in sixteen fractional-phase regions (i.e., one-sixteenth-phase regions). The particular region the component signal is residing in at any given time would be determined by comparing the analytic phase to the bounding phase values. As before with parameter T4, a parameter TN would be the time length between fractional-phase transitions into and out of the corresponding fractional phase. The amplitude parameter a of the corresponding object may be determined as before, for example by the maximum value, mean value, rms value, or related amplitude measure over the fractional phase, with the added ability to evaluate these based upon a complex-amplitude measure (i.e., the analytic amplitude).

FIG. 7E is a matrix 753 containing the sixteen possible quarter-phase regions (states) of a method 700, for two component waves.

In some embodiments, for a set of Nc components, for quarter-phase object resolution the total number of potential states is $4^{Nc}$. For the fractional-phase case with total possible fractional phases F (such that for quarter-phase, F=4), the total number of potential states is thus $F^{Nc}$. For example, with quarter-phases, the system of two components may take on any of the 16 possible states ($4^2$), depending upon the relative timing and phase offset of the two components. Again, a system of three components may take on any of the 64 possible states ($4^3$). This may extended to the case of any number of components and fractional phases.

In some embodiments, these finer fractional-phase transition points, fractional-phase regions and resulting objects may be suitable for certain applications requiring a finer underlying phase resolution per component, such as situations where the component signal substantially deviates from a sinusoid. However, it can be noted that resolving the analytic phase, in some embodiments, requires evaluation or approximation of the inverse tangent function, which may be prohibitive in certain applications. Further, it can be noted that, in some embodiments, such finer resolution may also be obtained by simply adding and utilizing an appropriate higher-frequency component and its associated quarter-phase objects. Thus, the fractional-phase representation is provided as an embodiment of this current invention, and a direct extension of the quarter-phase representation.

One may further note that, in some embodiments, the complete analytic signal may be utilized. In some embodiments, the fractional phases and transitions of the imaginary part of the analytic signal may be detected and measured, thereby generating objects for the imaginary part in substantially the same manner as already described for the real part. Additionally, timing and amplitude information from the real part objects may be used for the imaginary part objects, and vice versa. For example, the real and imaginary parts of the amplitudes may be recorded at all fractional-phase transitions for either or both real and imaginary parts, to establish a moving measure of local energy in the component. Adding the imaginary-part information serves to increase the amount of objects and/or the amount of information per object. This in turn increases the object storage and/or transmission requirements, but can be useful for processing steps involving the objects.

In some embodiments, a special case exists having quarter-phases based upon an analytic component. In this case, zero crossings from both the real part and the imaginary part of the component are used to define the quarter-phase regions, and the complex amplitude information at these zero crossings are used to establish an amplitude measure. This case has particular applicability to multiplierless architectures for creation of quarter-phase objects.

In some embodiments, if the amplitude measure of an object falls below a certain threshold, the object could be flagged, or a special object could be generated, to indicate the absence of the component, whereupon the component and/or object are considered "quiescent". This is useful for analysis of signals having relatively long quiescent periods in some or all components, such as, for example, ECG signals in the higher-frequency components centered roughly 20 Hz and above.

As the original signal varies or undulates over time, various objects are generated from the corresponding components, and the signal takes on various states, acquiring a new state with each object generated. The sequence of states may then be analyzed as a collection for characterizing the original signal. For example, a purely periodic original signal would produce a perfectly repeating pattern of states. Provided that the fundamental period falls within the passband of one of the components, the substantially lowest-frequency component that is active would produce the same object, for example, an object with the "$A_1$" label, once per fundamental period. If needed, more precision in time would be afforded in this example by detecting particular labels for higher-frequency components synchronous with the "$A_1$" label. Quasi-periodic patterns may also be followed by identifying local cycles of repetition among the states and objects. For example, a certain sequence of states and/or object labels may be identified with an original signal associated with a certain condition. The entire sequence may be given a label according to that condition, and stored and processed simply according to this predetermined label. Next is described how to extend this general idea of linking objects and states, and how to utilize these links.

Object Links, State Links

FIG. 8A provides a description of a data structure 800 that, in some embodiments, is contained on a computer readable medium. This object contains some and or all of the following attributes:

Object ID 801—Some unique identifying code or value that facilitates retrieval of each object.

T4 value 802—the value of T4 in some useful unit, such as discrete and/or fractional samples (i.e., related to a constant sample rate for the original signal), or seconds.

Phase label 803—a quarter-phase object denoted by the letter A, B, C, or D.

Atomic period Value 804—(AP) An object-local estimate of the period of the component. In some embodiments, T4 multiplied by 4.

Amplitude measure 805—the height of the wave from some zero crossing, amplitude is denoted by a.

Total time elapsed 806—from some "origin" or "reference" time.

Relative amplitude value 807—relative amplitude ($K_A$) of object with respect to some meaningful reference, such as the local amplitude measure of the original signal (amplitude measure as defined previously).

Relative T4 value 808—relative T4 ($K_T$) of object with respect to some meaningful reference, such as the latest T4 of the active component with the longest period (i.e., the longest currently active T4).

This list of attributes is by no means complete and, in some embodiments, additional attributes such as a component ID containing data relating to the identity of the component from which the object originates may be desirable. Further desirable attributes might include a signal ID to identify the signal upon which the object is based.

In still other embodiments, an object will contain a single field value and a single link (i.e., memory address) linking this single-field object to another object. For example, a first such single-field object might contain an Object ID field and a link that links the first single-field object to a second single-field object, which contains only a single T4 value and a link that links the second single-field object to a third single-field object, which contains a phase label and a link that links the third single-field object to yet another single field object and so on, each single-field object linking to another until some end-of-link. In some embodiments, these objects may contain two data fields (e.g., one for the Object ID and T4 value) and a single link. In some embodiments, these objects may contain three data fields (e.g., one for the Object ID, T4 value, and phase label) and a link to other objects. In some embodiments, these objects might contain four data fields (e.g., one for the Object ID, T4 value, phase label, and atomic period) and a link to another object. In some embodiments, these objects might contain five data fields (e.g., one each for the Object ID, T4 value, phase label, atomic period, and amplitude measure) and a link to another object. In some embodiments, these objects might contain six data fields (e.g., one each for the Object ID, T4 value, phase label, atomic period, amplitude measure, and total time elapsed) and a link to another object. In some embodiments, these objects might contain seven data fields (e.g., one each for the Object ID, T4 value, phase label, atomic period, amplitude measure, total time elapsed and relative amplitude value) and a link to another object.

FIG. 8B describes a data structure 851 having various links to other objects that a particular object might have in some embodiments. Links are memory addresses as is commonly understood in the art of computer science and software engineering. (See *Java How to Program* 3<sup>rd</sup> *Edition*, by H. M. Deitel & P. J. Deitel, Prentice Hall, 1999.) In some embodiments, these are the memory addresses of objects. In some embodiments, the following links are associated with the objects described herein:

Left object 809—The previous object, of the same phase label, generated from this same component.

Right object 810—The next object, of the same phase label, generated from this same component.

Left harmonic 811—A measure of cyclic regularity leading up to the current object. A comparison of left local period by label (LLPL) to either of left local period by time (LLPT) or AP. Comparison may for example be a ratio (such as LLPL/LLPT or LLPL/AP) or a difference (such as LLPL-LLPT or LLPL-AP). Ratios would be compared to unity, and differences compared to zero. Over-unity ratios or positive differences would be indicative of non-cyclic transients resulting in fewer fractional-phase transitions than would be expected in the case of cyclic regularity. Under-unity ratios or negative differences would be indicative of non-cyclic transients resulting in more fractional-phase transitions than would be expected in the case of cyclic regularity.

Right harmonic 812—A measure of cyclic regularity following the current object.

Same as left harmonic, except using right local period by label (RLPL) and right local period by time (RLPT) in place of left local period label and left local period time, respectively.

Left neighbor 813—The previous object generated from this same component, (i.e., O(i−1)j).

Right neighbor 814—The next object generated from this same component, (i.e., O(i+1)j).

Lower neighbors 815—The object or objects that are active at this link's generation and corresponding to (i.e., generated from) lower frequency components.

Upper neighbors 816—The object or objects that are active at this link's generation and corresponding to (i.e., generated from) higher frequency components.

In some embodiments, these objects are organized as a list, stack, queue, tree, heap, hash table or some other structure known in the art. (See *Algorithms in C++* 3<sup>rd</sup> *Edition*, by Robert Sedgewick, Addison-Wesley, 1998.) The determination of exact manner in which these objects would be organized would be implementation specific, and hence left up to the particular software developer's efficiency, and speed requirements.

In still other embodiments, an object will contain a single field value and a single link (i.e., memory address) linking this single field object to another object. For example, such an object might contain a left object field and a link linking this object to a second single-field object, which in turn contains only a single right object value and a link that links the second single-field object to another single-field object, which in turn contains a left harmonic and a link that links to yet another single-field object and so on (i.e., a linked list of single-field objects). In some embodiments, these objects may contain two data fields (e.g., left object and right object) and a single link. In some embodiments, these objects may contain three data fields (e.g., left object, right object and left harmonic) and a link to other objects. In some embodiments, these objects might contain four data fields (e.g., left object, right object, left harmonic, and right harmonic) and a link to another object. In some embodiments, these objects might contain five data fields (e.g., left object, right object, left harmonic, right harmonic, and left neighbor) and a link to another object. In some embodiments, these objects might contain six data fields (e.g., left object, right object, left harmonic, right harmonic, left neighbor, right neighbor, and lower neighbors) and a link to another object. Thus, the linked lists may contain like-length objects all having the same number of data fields, or different-length objects having different numbers of data fields.

In some embodiments, the various data containing attributes, fields would be filled as objects are generated and information becomes available. Information pertaining to objects not yet generated would be filled in as those objects are generated, or at some suitable time after those objects are generated. Because objects from another component may be generated while an object from one component is still active, it is possible that the links to upper neighbors and lower neighbors may require a list of appropriate links to handle the multiplicity of object pairings. In some embodiments, the length of such lists of links is expected to be on the order of the ratio of the periods of the associated paired components, and so should be readily manageable.

Horizontal Linking

In some embodiments, an object has two different types of links. Horizontal links deal with timing relationships and order of occurrence of objects and/or attributes of objects all arising from a certain component. Link types 809, 810, 813, and 814 fall into this category. Vertical links deal with relationships between objects arising from different components, and so link types 815, 816 fall into this category.

Horizontal links are useful for arriving at measures of the local periodic structure of component signals and, by extension, that of the original signal. In some embodiments, such measures arise from the analysis of object attributes in the context of horizontal links. One may call such measures "linked attributes".

FIG. 8C depicts a data structure 852, which, in some embodiments, contains linked attributes such as:

Left local period by label (LLPL) 817—The time difference between this object and the previous object from the same component having the same label as this object.

Right local period by label (RLPL) 818—The time difference between this object and the next object from the same component having the same label as this object.

Left local period by time (LLPT) 819—The sum of T4 for this object and the past three non-quiescent objects from the same component. More generally, the sum of T4 for this object and the past $N_T$ non-quiescent objects from the same component, normalized by the factor $4/N_T$.

Right local period by time (RLPT) 820—Same as left local period time except using T4 for this object and the next $N_T$ non-quiescent objects from the same component.

Cyclic regularity 821—One may expect that under steady-state conditions, successive objects generated from a given component would have labels following a progressive sequence ( . . . , A,B,C,D,A, . . . ). In some embodiments, the repeating pattern could start with any of the labels. Changes in this pattern would indicate a deviation from steady state, (i.e., a transient condition, in the associated component band, and may be appropriately flagged as such with this attribute). If X is defined as the quiescent label, then transitions to and from the X label in the object sequence would signify the special case of that component becoming inactive or active, respectively, and may also be appropriately flagged as such with this attribute.

Amplitude modulation 822—Difference or ratio of amplitude measure α of this object and that of neighboring object (may be right or left).

Further examples involve statistics on attributes, such as the mean, variance, trend analysis, estimation of probability density and distribution, or time-series models operating on such indexed sets of attributes. Typically, linked attributes deal with measures that collect sets of attributes from two or more related (i.e., linked) objects, which are applicable at the time of the current object. In some embodiments, these measurements are associated as attributes with an object, while in other embodiments these measurements may be derived from two or more objects, but the actual measurements and resulting values (e.g., linked attribute values reference numbers 817, 818, 819, 820, 821, 822) themselves are stored elsewhere (e.g., in a separate data structure, or variable).

In still other embodiments, an object will contain a single field value and a single link (i.e., memory address) linking this single-field object to another object. For example, a first such single-field object might contain a LLPL field and a link that links the first object to a second single-field object, which in turn contains only a single RLPL value and a link that links to yet another single-field object, which in turn contains a LLPT field and a link that links to still another single-field object and so on. In some embodiments, these objects may contain two data fields (e.g., LLPL, and RLPL) and a single link. In some embodiments, these objects may contain three data fields (e.g., LLPL, RLPL, and LLPT) and a link to other objects. In some embodiments, these objects might contain four data fields (e.g., LLPL, RLPL, LLPT and RLPT) and a link to another object.

Vertical Linking

Vertically linked objects (VLO) are defined as those objects that are collectively, simultaneously active and linked vertically. In some embodiments, by using the attributes contained in objects and/or by performing calculations using these attributes it is possible to generate, recreate various representations of the component wave signals that served as the basis for the VLO. One such representation is the state matrix and/or the state transition matrix. Such state-related matrices are well understood in the art, for example, in the area of Hidden Markov Models.

In some embodiments, when representing VLO in a transition matrix it is important to define "a state" as consisting of a vector of objects derived from one or more original signals, and a "state space" as the discrete vector space indexed along each unique dimension by object labels corresponding to a particular component. It is then possible to refer to a trajectory of states as traversing such a state space.

FIG. 9A is a state-transition matrix 900 of the available states for a system of two components. In this example, the available states represent two components with quarter-phase objects, for a total of 16 possible states. In the table are shown a few examples of state trajectories drawn as arrows to the next state along the trajectory. The illustrated example depicts a series of transitions from Aa→Ab→Ac→Bc→Bd→Cd→Ca→Cb→Db→Dc→Dd.

Figure 9C:
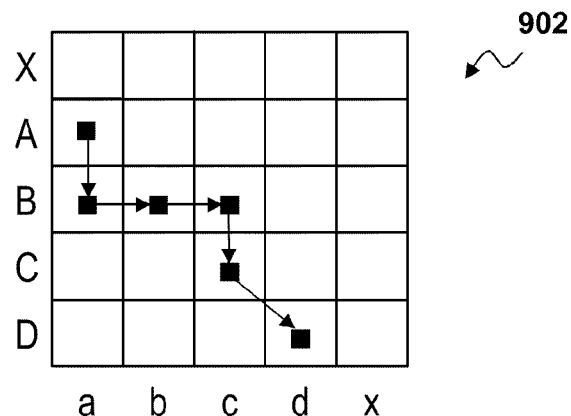
FIG. 9C is a simplified state-transition matrix 902 of the available states for a system of two components.

FIG. 9C is a simplified state-transition matrix 902 of the available states for a system of two components. The illustrated example depicts a series of transitions from Aa→Ba→Bb→Bc→Cc→Dd.

In FIG. 9A, the object labels X and x are given to signify a "don't care" condition, which could arise from any arbitrary criteria, for example, due to objects having amplitude measures below a certain threshold (quiescent objects). As shown in the table, the don't-care condition is associated with multiple states, which may be taken collectively as a "super state" that is useful for simplifying the state and/or state transition analysis.

Figure 9D:
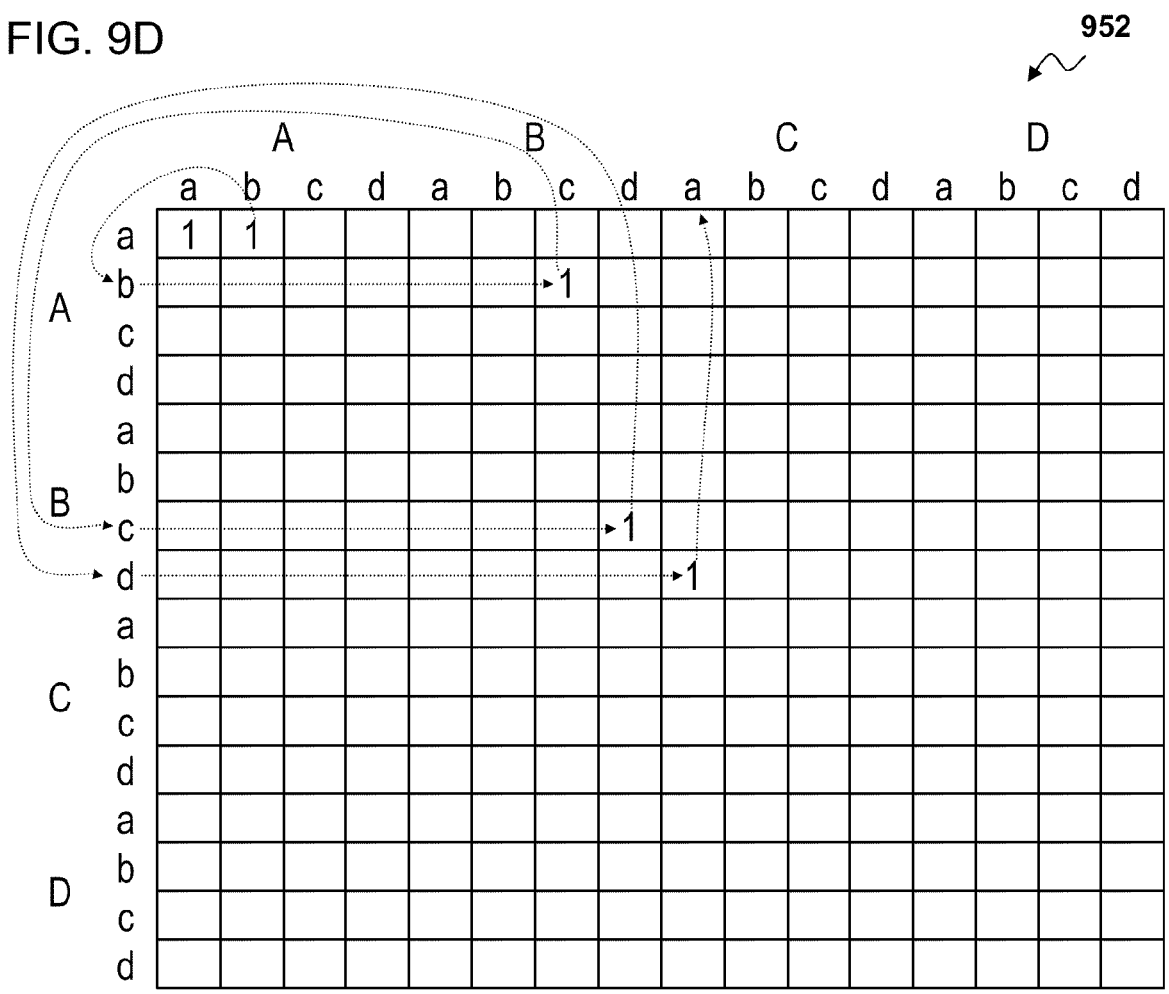
FIG. 9D represents a simplified state-transition matrix 952, in table form.

FIG. 9B represents a state-transition matrix 951, again in table form. This matrix lists all possible states along each dimension, with the starting state for a given transition along one dimension and the ending state for the transition along the other dimension. In this example, two components with quarter-phase objects results in a 16×16 matrix. On a given state transition, an appropriate entry in the table/matrix is flagged or accumulated. The "ones" in the matrix given in the figure represent the state transitions for the associated state trajectory given in the figure below the table. While not shown, the table and/or matrix may be readily extended to include entries corresponding to transitions to and/or from a "don't care" state (or super state). FIG. 9D represents a simplified state-transition matrix 952, again in table form. The illustrated example in FIG. 9D depicts a transition from Aa→Ab→Bc→Bd→Ca.

In these given example tables or state-transition matrices (i.e., FIGS. 9A and 9B), only two components with quarter-phase objects are shown for the sake of clarity. Of course, the invention is not limited to only two components with quarter-phase objects. In actuality, and throughout this invention, an arbitrary number of components and/or fractional phases may be used.

As stated above, in some embodiments, a periodic or qp original signal will produce a repeating (or near-repeating) pattern of states. Tracing out the sequence of states with dots and arrows on the table would tend to produce a signature pattern discernable to the human eye. Once such a pattern is understood, deviations from such a pattern, even relatively subtle ones, would also be discernable. Simple sequence detectors may be constructed to match a particular expected sequence of states, or expected set of such sequences, particularly cyclic ones originating (and/or ending) at a particular state or fundamental component object (i.e., fundamental in the sense of the lowest-frequency active component). The object/state representation affords the application of a variety of ad-hoc methods for identifying morphologic features or sequences of such features. Any of the object data could be utilized in conjunction with state pattern data to enhance the robustness of the pattern recognition. For example, the vector of object amplitudes associated with a particular state could be used with a threshold condition to qualify a certain state or pattern identification.

Methods of Interpreting and Analyzing Data: Hidden Markov Models and Neural Networks Methods for automatically training on and identifying such patterns and pattern deviations in state space are well understood and established in the art, such as Neural Networks (NN) and Hidden Markov Models (HMM). (See *Neural Networks: A Comprehensive Foundation*, S. Haykin, Prentice Hall, 1999; *Learning Hidden Markov Model Structure for Information Extraction*, by Kristie Seymore, Andrew McCallum, and Roni Rosenfeld, American Association for Artificial Intelligence 99, Workshop on Machine Learning for Information Extraction, 1999.) In any case, a training dataset would be presented to the system, for example, in the form of original signals representative of the condition(s) to be modeled, thereby producing a corresponding repository of objects and states. In the case of training with supervised learning algorithms, the object repository would be labeled according to the condition(s). In the case of training with unsupervised learning, no condition labels would be provided and models would be formed by identifying emergent clusters, such as for example with Self-Organizing Maps and Generative Topographic Maps.

In some embodiments, training is established, in the NN example, by converging on a set of weights that correspond to a particular state trajectory pattern (or cluster of trajectory patterns that are "close" in state-space). In the HMM example, training is established by building statistics on states and transitions between states, such as estimating the probability of occurrence of a particular state, and the conditional probability of the transition from one particular state to the next. The state and state-transition matrices may provide the framework for these statistics. While exercising the training dataset, each time a certain state is encountered, the corresponding element of the state matrix would be incremented. The length of time spent in a particular state may also be accumulated, and/or the time from the previous similar transition may be recorded. Accordingly, each time a certain state transition is encountered, the corresponding element of the state matrix would also be incremented. If necessary, these accumulated values may be split into separate accumulation bins, one for each condition label. The statistics can be derived by normalizing by the appropriate count, for example the total number of trials, the total number of trials for a certain condition, the total number of state transitions, and/or the total number of state transitions for a certain trial.

Regardless of the particular method, a test trajectory may be compared for degree-of-match to a trained trajectory pattern or set of patterns. As is known in the art, the degree-of-match measure may be based upon a distance measure in state space, or comparison of the probability of tracing that particular path based upon accumulated statistics.

In some embodiments, the structure of objects, states, and state space in this invention provides a solid framework for building up state models such as those found in HMM. Traditionally, given an original signal, translating points along this signal into useful states for building an HMM has been difficult. Such translation has been typically based on ad-hoc methods of delineation of the original signal waveform. The method of this invention provides a natural mapping between discrete states and significant points in the original signal.

For the ECG example, such networks and/or models may be trained using nominal (or normal) data, and then tested with data that may be normal or correspond to a pathologic condition such as ischemia or arrhythmia. The match or absence of match would act as a discriminator of normal and abnormal conditions. Further, training on a set of one or more different abnormal conditions would allow distinguishing among them as well.

State Space with Attributes

Each state naturally carries all of the underlying information associated with the VLO from which the state is comprised. Thus, at each state, all of the attributes, links, and linked attributes including the VLO are available for use. For example, a particular state trajectory or path may map out an ordered set of states $\{S_k, k=1 \ldots N_S\}$, where $N_S$ is the total number of states in the path. One may thus construct an $N_O \times N_S$ matrix A of a particular attribute, with the $k^{th}$ column being the $N_O$ values of the attribute for the objects including the state $S_k$. This matrix may then be applied to an augmented HMM or NN for training and testing purposes. One example embodiment would train an HMM directly on states and state transitions only, while training an NN on corresponding attribute matrices for each training trajectory of the HMM. Another example embodiment would use only the information in the attribute matrices, for example to directly train an NN. Such augmented or alternate training could be advantageous in identification or discrimination applications that are more sensitive to information contained in the ordered attributes.

Note that all embodiments may also use more than one attribute in the training and testing, whereupon multiple attribute matrices would be constructed and utilized. One may add to the list of possible attributes the time spent in a particular state, which may be expressed as an absolute time or a percentage of the time for the whole state trajectory, and/or the period or relative frequency of a particular state transition.

State Space with Time Context

A state trajectory may be characterized in some cases by certain states that are inhabited a relatively long time, connected by intermediary states that are inhabited for a relatively short amount of time. Similarly, a state trajectory will generally move more slowly (change less often) along some object dimensions, and at a faster rate along others, according to the fundamental frequencies of the associated component bands. One may thus consider states in their time-context, and so reject states, and/or transitions to and from such states, that represent relatively small time contributions to the state trajectory. This can serve to reduce excess complexity in state trajectories due to relatively rapid chatter between states.

Reconstruction of Base Wave Form

In some embodiments, the base waveform is substantially reconstructed from a linear combination of its associated components. A particular set of quarter-phase objects and their associated attributes are used to reconstruct each component wave, and so in turn each reconstructed component wave is used to reconstruct the base waveform. As described above, in some embodiments, a quarter-phase object contains the attributes of amplitude ($\alpha$), time (T4), and an associated label (e.g., A, B, C, or D). In some embodiments, there is an object ID associated with each object. If, for example, one considers four objects (A, a1, T1), (B, a2, T2), (C, a3, T3), and (D, a4, T4), one can reconstruct a component waveform along time variable t, over an interval from 0 to T, such that:

A a1, sin($\Pi/2 \cdot t/T1$)

B a2 cos($\Pi/2 \cdot t/T2$)

C—a3, sin($\Pi/2 \cdot t/T3$)

D—a4 cos($\Pi/2 \cdot t/T4$)

Using the above values, one cycle of the original signal of the component form is estimated. The time adjustment among reconstructed components is maintained by sampling time and applying all component reconstructions with appropriate time alignments, deriving an absolute time reference for each component from an accumulation of the T4 values, or using the "total time elapsed" attribute if available to establish absolute timing. The reconstructed components provide the ability to reconstruct the base quasi-periodic waveform by a linear combination of these reconstructed components.

Reconstruction and Data Compression, Storage and Transmission

In some embodiments, higher-frequency components will generate more objects within a local time period. For example, the ECG wave will only be generated substantially in the area of the QRS complex over a relatively narrow range of time, as a percentage of time per beat. However, other high-frequency components may be discarded to the degree that the loss of high frequency information can be tolerated in the reconstruction. Components maybe discarded based upon redundancy of the object and the data stored therein, or other features that render the data unremarkable relative to other data sets contained in other objects and components. In some embodiments, a determination of whether or not to discard a component may be based upon a data sampling of these objects and components. The ability to discard some high frequency components has a number of advantages. First, it allows for less storage space to be used to store the objects. Next, the existence of fewer objects means quicker retrieval times of the requisite data used in reconstruction. Moreover, the existence of fewer objects means that less processor cycles need to be devoted to a particular data set, thus again increasing execution time. Once a redundant data is discarded the remaining data may then, in some embodiments, be transferred in some type of compressed format know in the art. (See *Data Compression* $3^{rd}$ *Edition*, by David Salomon, Springer, 2004.)

A Software Implementation of the Above Method, Data Structure, and State

One example implementation if the present invention is reflected in the below described calling tree and the associated functions written in pseudo code appearing at each level of the calling tree. For the purpose of brevity and conciseness, below we will provide pseudo-code examples pertaining to the generating of a filter bank (i.e., the GenerateFilter Bank node and associated child nodes), and pseudo-code relating to the generation of quarter-phase representations in object form (i.e., the GetState node and associated child nodes). The calling tree is described by the cells and by the successive top-down connections between cells in the following table:

| System_Driver | | | | |
|---|---|---|---|---|
| Get State | Time Freq. Analysis | Generate Filter Bank | | Load Data |
| Get Objects Find qp Find Zero crossing | Linear Phase Filter | Returns Hilbert Transform | Filter Band Multiple convolve | Get Data |

One knowledgeable in the art would be able to use this calling tree as an architectural blueprint to implement some embodiments of the present invention.

Examples of a System Driver and Methods for Implementing

An example pseudo-code representation of a System_Driver function for a software implementation of the present invention is described below. Central to this System_Driver function is a GenerateFilter Bank function ("genFilterBank"), in conjunction with a Time-Frequency Analysis function ("tfAn"), and a GetState ("getState") function. The genFilterBank implements the analytic wavelets for the above-described Parallel-Form Kovtun-Ricci Wavelet Transform, while the Time-Frequency Analysis performs the transform in block form using the precomputed wavelets from genFilterBank. The getState implements the quarter-phase object and state representation described above. The pseudo-code representation for the System_Driver function is as follows:

```
System_Driver ( );
// load data signal ECG into some type of data structure
```

-continued

```
[data,Fs] = loadECG;
// call and generate a parallel filter bank
[cH,D,kb] = genFilterBank;
// determine the number of filter bands
Nb = length(cH);
// decompose signal using filter bank, providing resulting components as
a matrix X = tfAn(data,cH);
// display plot data and sum of components that approximate the data
plot(real(sum(X')),'Linewidth',2); hold on; plot(imag(sum(X')),':',
'Linewidth',2);
plot(data);
xlim([0 2500]) // setting range of x-axis
// captioning for graph
legend('real','imag','data') xlabel('time (msec)')
// call find quarter-phase objects and states in component signals
[S,cS,sObjStrm,sObj] = getState(X);
// determine number of quarter-phase objects found
Nobj = length(sObjStrm);
// plot components with associated active quarter-phases marked
for i = 1:Nb
{
    subplot(Nb,1,i); plot(real(X(:,i)));
    plot(imag(X(:,i)),'--');
    iact = find(sObj(i).act);
    inact = find(~sObj(i).act);
    plot(sObj(i).iqp(iact),real(X(sObj(i).iqp(iact),i)),'.');
    plot(sObj(i).iqp(inact),real(X(sObj(i).iqp(inact),i)),'x');
    xlim([0 2500]); // setting range of x-axis
    // captioning for graph
    ylabel([num2str(round(Fs/(2*kb(i)))),' Hz']);
}
xlabel('time (msec)')
// plot data with quarter-phases marked
xr = real(sum(X')); // the sum of the real component values to be plotted
plot(xr); hold on
for i = 1:Nobj
{
    if sObjStrm(i).act
    {
        plot(sObjStrm(i).iqp,xr(sObjStrm(i).iqp),'.')
}}
xlim([0 2500]) // setting range of x-axis
// captioning for graph
title('ECG data and active qp object points marked')
xlabel('time (msec)')
// number of states
Nstate = length(S);
// plot zoomed data with qp's marked and state labels texted
// setting ranges of plotting
istrt = 250;
iend = 420;
plot(istrt:iend,xr(istrt:iend)); hold on
for i = 1:Nstate
{
    if prod(S(i,:)) // activity test (all components active to make mark)
    {
        iObj = cS{i}; // indices back to object stream
        iqp = sObjStrm(iObj(1)).iqp; // resolve time index
        if iqp > istrt & iqp < iend    // restrict markers to plotted range
        {
            plot(iqp,xr(iqp),'.') // mark state location on data
            for j = 1:Nb // place state label vertically on
            {
                plot_text(iqp,xr(iqp)-0.1*j,num2str(S(i,j)))
}}}}
axis([istrt iend -1 2]) // setting range of axes
// captioning for graph
title('ECG data, active qp obj points, and state labels')
xlabel('time (msec)')
```

One knowledgeable in the art would be able to implement this pseudo-code representation of the System_Driver function and those functions described below on a general-purpose computer using an object oriented programming language such as C++, C#™, Java™ or Delphi™. Similarly, one knowledgeable in the art would be able to implement this pseudo code on a general-purpose computer using a structured programming language such as Matlab™ or C. Alternatively, one knowledgeable in the art could design an embedded circuit/hardware implementation of this pseudocode representation.

Example Filter Bank and Methods for Implementing

As outlined above in the calling tree, the System_Driver function, in some embodiments, calls a Generate Filter Bank function ("genFilterBank"). Essential to this genFilterBank function is a Filter Band function ("difilter") to create individual Kovtun-Ricci wavelets and a Returns Hilbert Transform function ("hilbananorm") to convert real wavelets into normalized analytic form using a Hilbert transform coupled with normalization in the frequency domain. The pseudocode representation of the genFilterBank is as follows:

```
genFilterBank( cH, D, kb)
// Functions parameters/arguments
// cH = array of analytic wavelet coefficients
// D = array of intrinsic delays
// kb = array of wavelet scaling factors (relative to Nyquist)
Fs = 1000; // sample rate (Hz)
f0 = 1; // base center freq. (Hz)
fc = f0*2.^[0:4]; // freq. centers
kb = round(Fs./(2*fc)); // set of scales
Nb = length(kb); // number of bands
// wavelet parameters
Nd = 4; // derivative order
Ni = 4; // integrator order
// create bank
cH = cell(1,Nb); // initializes cells/arrays
D = zeros(1,Nb);
for i = 1:Nb // generate set of filter responses
{
    k = kb(i); // derivative scale
    w = ceil(2*k/3); // integral scale: "optimal" upper harmonic
    [h,D(i)] = difilter(1,k,Nd,w,Ni);
    cH{i} = hilbananorm(h)';
}
```

Called within this genFilterBank function are the difilter and hilbananorm functions. The difilter, among other things, returns an "h" value from the Parallel-Form Kovtun-Ricci Wavelet Transform representing a real wavelet, or component filter impulse response. This wavelet is then passed to the hilbananorm function implementing a Hilbert transformer. The following pseudo-code implements the difilter:

```
difilter(x,k,Nd,w,Ni)
// Parameters/arguments
// x = filter input
// k = derivative time-scaling factor
// Nd = order of derivative kernel
// Optional integrator parameters (must be passed together):
// w = integrator time-scaling factor
// Ni = order of integrator kernel
// compute intrinsic delay from parameters, in samples
D = Nd*k/2 + Ni*(w-1)/2; // composite derivative and widener
kd = [1,zeros(1,k-1),-1]/2; // Scaled derivative kernel
y = mconv(x,kd,Nd); // Nd-order derivative operator
// Scaled integrator kernel
ki = ones(1,w)/w; // Scaled integrator kernel
y = mconv(y,ki,Ni); // Ni-order integrator operator
```

Once difilter is implemented, a filter output value or "y" value and intrinsic delay value or "D" stored in a data structure, such as an array, are returned. Function difilter implements an input-output model, such that an input signal "x" is passed in to produce filtered output "y" according to wavelet parameters k, Nd, w, and Ni. On calling difilter, passing in a "1" for "x", as does genFilterBank, thus returns in output "y"

the impulse response of the filter, or the wavelet itself. This output is returned into "h" in genFilterBank, then passed to the hilbananorm function, the pseudo-code for which is described as follows:

```
hilbananorm(hr,domain)
// Parameters/arguments
// hr = real impulse response
// domain = domain of normalization, 'freq' = default, or 'time'
Na = 2^ceil(log2(length(hr))); // zero-pad to efficient number of points
Na = max([Na, 8192]); // ensure a minimum frequency resolution
H = fft(hr,Na); // fft
H(Na/2+1:end) = 0; // zero upper half-spectrum
hc = 2*ifft(H/max(abs(H))); // normalize and ifft
hc = conj(hc(1:length(hr))); // take conj, set back to original length
```

In some embodiments, a complex analytic form signal or impulse response "hc" of input signal or impulse response "hr" is returned. In this example, value "hc" is the analytic form of the wavelet. This wavelet is then passed back up to the genFilterBank function and becomes one member of the cell array "cH" (array of wavelets), and then ultimately up to the System_Driver function.

In some embodiments, a Multiple Convolve function ("mconv") is implemented. This mconv function convolves the input signal (i.e., "x") with an impulse response "h" multiple times, where the number of times is set by the value "n". This function implements a multiple cascade of kernels, where kernel "h" would in this example be the impulse response of a basic derivative kernel $Kd_p$ 301 or the impulse response of a basic integrator kernel $Ki_p$ 401 with the order of the kernel set by "Nd" or "Ni", respectively, depending upon the respective call from difilter, and is reflected in the following code:

```
mconv(x,h,n)
// Parameters/Arguments
// x = filter output or input value
// h = order of derivative kernel
// n = scaled derivative value
y = x;
for i = 1:n
{
    y = conv(y,h);
}
```

The output signal "y" resulting from the multiple convolution is returned, in this example, to difilter.

The System_Driver function, in some embodiments, calls a Time-Frequency Analysis function ("tfAn"). This function performs a wavelet transform of input signal "data" using array of wavelets "cH", by convolving each wavelet with input signal "data". Convolution is performed in this example by calling the Linear-Phase convolution function for each wavelet, returning for each wavelet the resulting analytic component signal. In this example the convolution result is truncated to the central samples of same length as the input "data", such that a zero-phase FIR filter is effectively realized with the wavelet. The function tfAn takes the convolution results and constructs output matrix "X". This matrix can be described as an N×M matrix, where N is along the time dimension and M is along the components dimension, such that each column of a matrix "X" is an analytic component signal (i.e., a band output). Matrix "X" is then returned to the System_Driver function.

In addition to the above-described functions and supporting pseudo-code used to generate a filter bank, functionality is implemented to allow for constructing quarter-phase objects or structures from components. As a threshold matter, in some embodiments, a Get State function ("getState") is called by a System_Driver function. This getState function takes an analytic component signal matrix "X" as a parameter or argument, in this example, as would be returned by the function tfAn. A pseudo-code implementation of getState is as follows:

```
getState(X)
// Parameters/arguments
// X = an N × M matrix
Nb = size(X,2); // number of components (bands)
[sObj,sObjStrm] = getObj(X); // get object stream
Nobj = length(sObjStrm); // number of objects in stream
// initialize state stream matrix and object index array
S = zeros(Nobj,Nb);
cS = cell(Nobj,1);
// first recorded state @ first object (initial state is implicitly zero)
iObj = 1;
iState = 1;
// update corresponding component dimension of state stream matrix
with new qp
S(iState,sObjStrm(iObj).Lcm) = sObjStrm(iObj).Lqp;
// set qp label to zero on inactive component
if ~sObjStrm(iObj).act
{
    S(iState,sObjStrm(iObj).Lcm) = 0;
}
cS{iState} = iObj; // record object index (indices) @ this state
iState = 2;
iObj = 2;
while iObj <= Nobj
{
    // object-triggered state change
    // check for "simultaneous" objects (objects appearing @ same sample)
    if sObjStrm(iObj).iqp ~= sObjStrm(iObj-1).iqp
    {
        // object not simultaneous: copy previous state forward
        S(iState,:) = S(iState-1,:);
    }
    else
    {
        // object simultaneous with previous: stay at previous state
        iState = iState-1;
    }
    // update corresponding component dimension of state stream matrix
    // with new qp label
    S(iState,sObjStrm(iObj).Lcm) = sObjStrm(iObj).Lqp;
    // set qp label to zero on inactive component
    if ~sObjStrm(iObj).act
    {
        S(iState,sObjStrm(iObj).Lcm) = 0
    }
    // record object index (or indices) @ this state
    cS{iState} = [cS{iState},iObj];
    // next object, next state, iterate
    iObj = iObj + 1;
    iState = iState + 1;
}
// truncate excess zero/empty states (if any) due to "simultaneous" objects
S = S(1:iState-1,:); // truncate excess zero/empty states (if any)
cS = cS(1:iState-1);
```

GetState returns the following outputs: "S", "cS", "sObjStrm", and "sObj". Output "S" is a matrix representing a stream of state arrays constructed from an object stream obtained from a matrix "X". Each column of "S" corresponds to a component (i.e., the corresponding column of "X"). Each row of "S" is a state array, here comprised of quarter-phase labels (see discussion of "getObj" below) which are set to zero if the associated component is inactive. A new state array is formed upon the change of active quarter-phase of a component (i.e., when a new object is formed). If more that one object is formed simultaneously, then the state array reflects the change of quarter-phase labels across all affected components. Output "cS" is an array equal to the length of "S" (i.e., the total number of states). Each element of "cS" is an array containing the indices of the individual data structures in the "sObjStrm" array of data structures that result in a corresponding state. As will be discussed below, output "sObj" is an array of structs, with each struct containing a plurality of arrays. Arrays of structures are commonly understood in the art. (See *C++ Primer Plus* $3^{rd}$ *Edition*, by Stephen Prata, Sams Publishing, 1998.) The output "sObjStrm" is an array of structs.

The states obtained via the getState function are defined by objects. In some embodiments, the objects are an array of structs, indexed simply by object index. In some embodiments, the objects are embedded into an array of structs, the array indexed according to the originating component dimension, with each struct of the array of structs containing a plurality of arrays indexed by object index. In some embodiments, a GetObjects function ("getObj") is described that accepts a matrix "X" as described above, and returns the array of structs, indexed simply by object index, in the above described "sObjStrm", and also returns the array of structs, indexed according to originating component dimension, with each struct of the array of structs containing a plurality of arrays indexed by object index, in the above described "sObj". Pseudo-code representing this getObj function is outlined below:

```
getObj(X)
// Parameters/arguments
// X = an N x M matrix
// number of components (bands)
Nb = size(X,2);
// define and build object structure
sObj(Nb) = struct('iqp',[ ],'Lqp',[ ],'amp',[ ],'act',[ ]);
for i=1:Nb
{
    // get qp representation (stream) for component
    [siqp,iqps,Lqps] = findQP(X(:,i));
    // build objects from component into struct for associated component
    sObj(i).iqp = iqps; // (time) index array of object occurrences (down a column of X)
    sObj(i).Lqp = Lqps; // quarter-phase label array per function findQP
    sObj(i).amp = abs(X(iqps,i)); // object amplitude array
    activeThr = 0.0625*max(sObj(i).amp); // establish "activity threshold"
    // active status of component flag array for each object
    sObj(i).act = (sObj(i).amp > activeThr);
}
// initialize an array of structs
sObjStrm = struct('iqp',[ ],'Lqp',[ ],'amp',[ ],'act',[ ],'Lcm',[ ]);
// build index-ordered object stream
iObj = [ ]; // index (time) of object
// append object info. from each component into single (sortable) array
c = 1; // object counter
for i=1:Nb
    {
    iObj = [iObj ; sObj(i).iqp]; // keep track of object indices
    for j=1:length(sObj(i).iqp)
        {
        sObjStrm(c).iqp = sObj(i).iqp(j); // assign (time) index
        sObjStrm(c).Lqp = sObj(i).Lqp(j); // assign qp label
        sObjStrm(c).amp = sObj(i).amp(j); // assign amplitude
        sObjStrm(c).act = sObj(i).act(j); // assign comp activity
        sObjStrm(c).Lcm = i; // assign comp associated w/object
        c = c + 1; // next object, iterate
    } }
// sort objects into ordered stream by order of appearance (index in time)
[iObjs,iiObjs] = sort(iObj);
sObjStrm = sObjStrm(iiObjs);
```

As described above, the getObj function returns both "sObjStrm" and "sObj". These return values are then returned to System_Driver by the getState function where they are used in the display of data, in some embodiments, graphically, or used for the purpose of analysis of component signals, original input signals or the like.

Object indices and quarter-phase labels for specific structs or objects are derived from a Find QP function ("findQP"). This function takes an analytic component signal "x" and from this component signal extracts arrays of quarter-phase values labeled as: 1, 2, 3, and 4 (corresponding to the above-described labels A, B, C, and D). The getObj function retrieves this information for each analytic component by calling findQP passing in for "x" each corresponding column of "X". The code for this findqp function is as follows:

```
findQP(x)
// x = analytic component signal
// initialize an array of quarter-phase index structs
siqp = struct('rp',[ ],'ip',[ ],'rn',[ ],'in',[ ]);
// indices for transitions into quarter-phases, with findzc
//    finding the indices of positive zero crossings
siqp.rp = findzc(real(x)); // Label A (rp) positive-going zero crossings
of real(x)
siqp.ip = findzc(imag(x)); // Label B (ip) positive-going zero crossings
of imag(x)
siqp.rn = findzc(-real(x)); // Label C (rn) negative-going zero crossings
of real(x)
siqp.in = findzc(-imag(x)); // Label D (in) negative-going zero crossings
of imag(x)
// build index-ordered quarter-phase stream
// quarter-phase labels
Lrp = ones(length(siqp.rp),1)*1; // labels A or 1
Lip = ones(length(siqp.ip),1)*2; // labels B or 2
Lrn = ones(length(siqp.rn),1)*3; // labels C or 3
Lin = ones(length(siqp.in),1)*4; // labels D or 4
// append qp indices and labels into single (sortable) arrays
iqp = [siqp.rp;siqp.rn;siqp.ip;siqp.in];
Lqp = [Lrp;Lrn;Lip;Lin];
// sort qp indices and labels by order of appearance
[iqps,iiqps] = sort(iqp);
Lqps = Lqp(iiqps);
```

There are three outputs for findQP: "siqp", "iqps", and "Lqps". Output "siqp" is a structure of arrays containing quarter-phase point indices, members arranged by label (i.e., A, B, C, D), each member an array of indices down a column of "X" at which occur qp points of the type corresponding to that label. Output "iqps" is an array of quarter-phase transition indices, for all label types, sorted in order of increasing value (i.e., order of appearance), and output "Lqps" is an array of labels for quarter-phases being entered at corresponding quarter-phase transition points indicated by array "iqps".

The above described functions (i.e., System_Driver, GetState, GetObject) use structs and arrays of structs whose fields contain a plurality of arrays to store and manipulate data such as, for example, components, states and the like. As has been described elsewhere these structs, common to many structured programming regimes such as Matlab™ or the C programming language, can be replaced with objects common to an object oriented programming paradigm such as C++, C#™, Java™ or Delphi™. Additionally, as is discussed above, these structs and/or objects can be organized into not only arrays, but list, stack, queue, tree, heap, hash table or some other structure known in the art. (See *Algorithms in C++* $3^{rd}$ *Edition*, by Robert Sedgewick, Addison-Wesley, 1998.) Additionally, any portion of these functions that utilize iterative methods to traverse a data structure, could, in the alternative, use a recursive method. Again, a determination of exact manner in which these structs and/or objects would be organized would be implementation specific, and hence left up to the particular software developer's efficiency, and speed requirements.

FIGS. 10A, FIG. 10B, FIG. 10C, and 10D depict various ways of reflecting the plotting of various component representations of an input ECG signal read in from a file using the above-described calling tree and functions represented in the above pseudo-code.

Figure 10A:
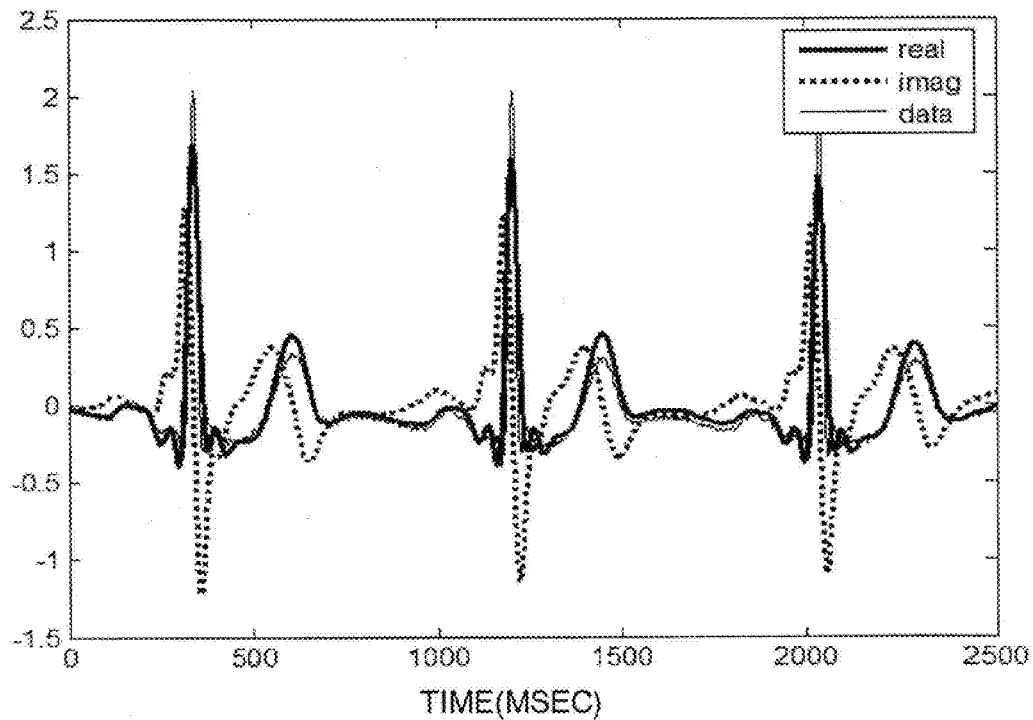
FIG. 10A is a graph 1000 depicting a plot of the input ECG signal and the reconstruction sums of the real parts and the imaginary parts of the components resulting from a parallel-form analytic filter-bank decomposition of the input ECG signal.

FIG. 10A is a graph 1000 depicting a plot of the input ECG signal and the reconstruction sums of the real parts and the imaginary parts of the components resulting from the parallel-form analytic filter-bank decomposition of the input ECG signal.

Figure 10B:
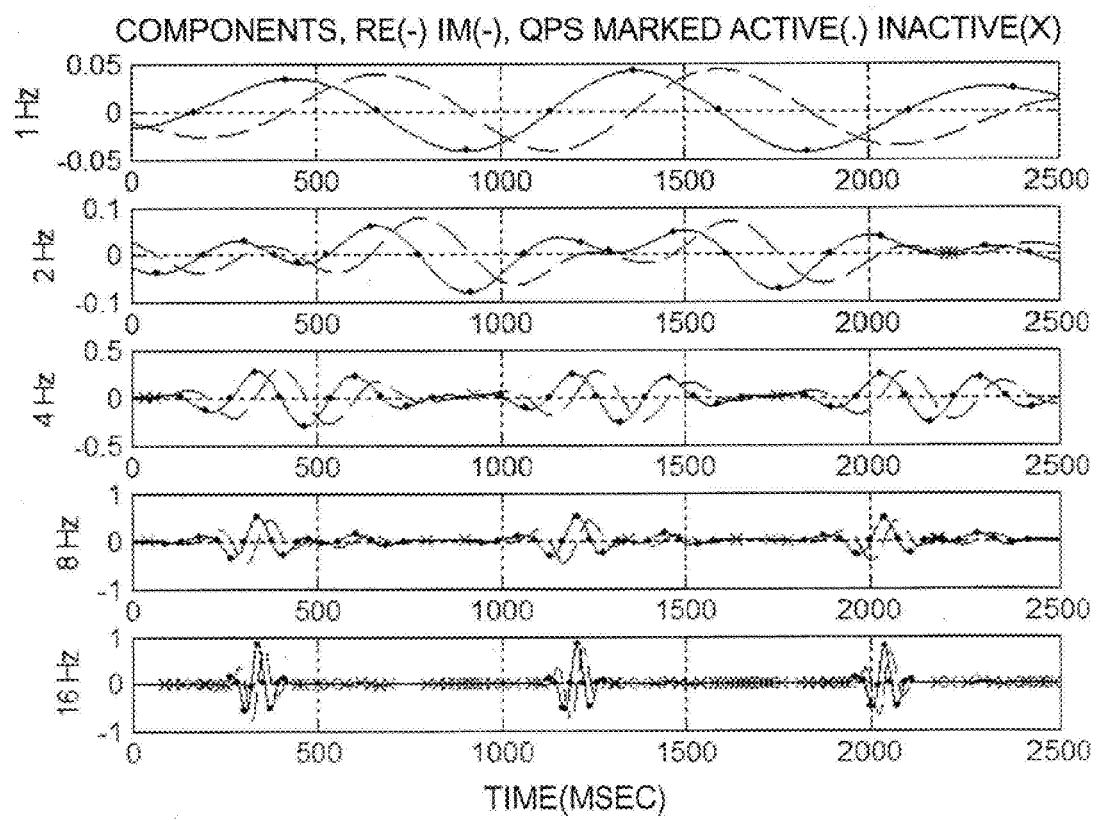
FIG. 10B is a graph 1001 of the analytic components, one for each band used in the example, with quarter-phase transition points marked.

FIG. 10B is a graph 1001 of the five analytic components resulting from the decomposition, one for each band used in the example, with the center frequency of each respective band marked on the left of each subplot. On each plot, the real part of the analytic component signal appears in the solid traces, and the imaginary part of the analytic component signal appears in the dashed traces. The quarter-phase transition points for each component are marked on the real-part traces, using a "dot" (".") where the component is active, and an "x" where the component is considered inactive (not active).

Figure 10C:
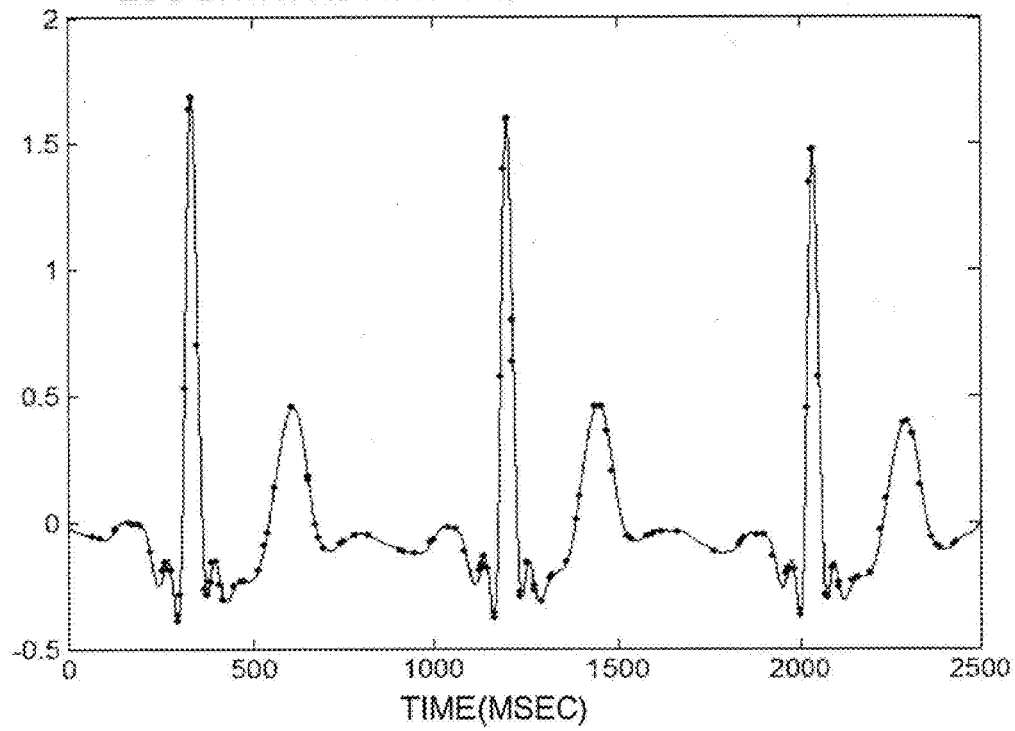
FIG. 10C is graph 1002 of the real-part component sum reconstruction of the input ECG signal, with all quarter-phase transition points marked.

FIG. 10C is graph 1002 of the real-part component sum reconstruction of the input ECG signal, with all corresponding quarter-phase transition points marked where the associated component is active.

Figure 10D:
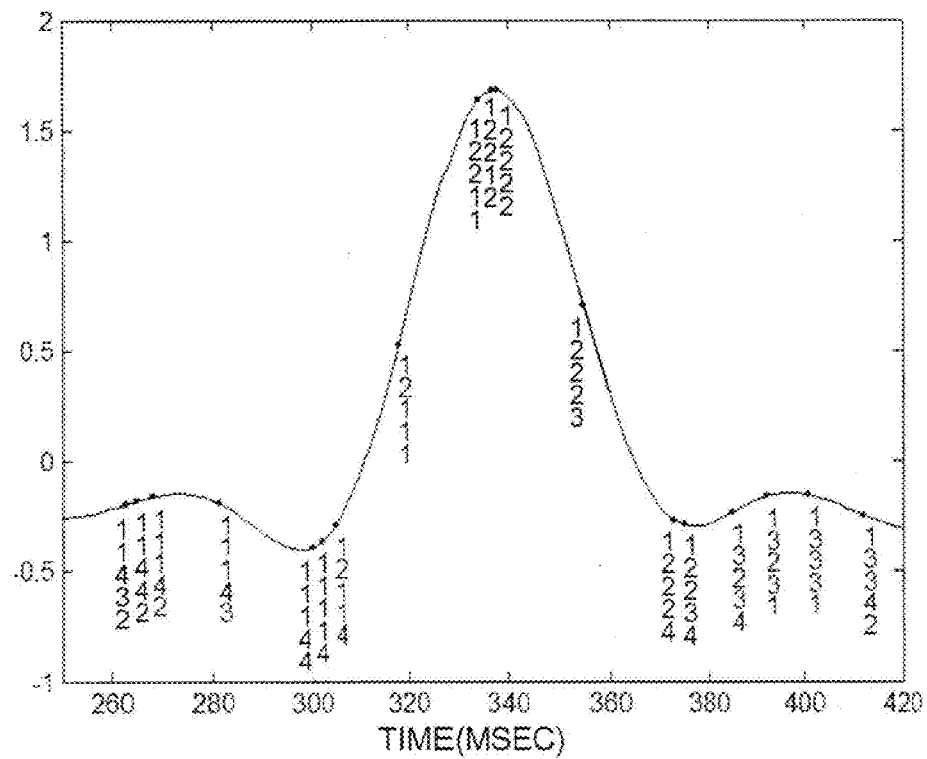
FIG. 10D is a graph 1003 of a specific segment taken from FIG. 10C in the range of 260 msec to 420 msec, with quarter-phase transition points marked and corresponding state labels denoted.

Finally, FIG. 10D is a graph 1003 of a specific segment taken from FIG. 10C in the range of 260 msec to 420 msec, with quarter-phase transition points marked and corresponding state labels denoted. The state labels are arranged each in a vertical stack of quarter-phase labels, with the quarter-phase label from lowest-frequency component on top and increasing in frequency toward the bottom.

Any of the above-described methods, filter banks, or data structures maybe described and implemented using a computer programming language. In some embodiments, the Parallel-Form Kovtun-Ricci Wavelet Transform, and/or Cascade-Form Kovtun-Ricci Wavelet Transform described above can be implemented using the C++ programming language in conjunction with certain programming language libraries such as Microsoft Foundation Class ("MFC"). C++ and MFC are well known in the art of computer science and software engineering. (See *Introduction to MFC Programming with Visual C++*, by Richard M. Jones, Prentice Hall PTR, 1999.)

In some embodiments, as described below, ECG data from a file serves as input for a program written in C++ and MFC ("the Program"). This Program (a copy of which is filed with U.S. Provisional Patent Application No. 60/656,630 referenced above) utilizes a cascade-form filter bank to divide up the base wave signal or original signal into its component parts. Once divided, each component wave is broken up into quarter-phases, and the data reflecting each quarter-phase is stored into an object, with each object horizontally and vertically linked to other objects. These objects are organized in a linked list structure, a structure well known in the art. Once linked, the data from these objects is retrieved, outputted into a wave representation.

The below matrix depicts the formation of a set of seven composite bands formed from certain sums of band outputs $y_p$ taken over contiguous ranges of p. In the Program, a bank of N=250 filter sections is implemented. Within each filter section, the component filter $H_p$ is comprised of only the scaled derivative kernel $Hd_p$ (i.e., the scaled integrator kernel $Hi_p$ is not used, or equivalently, it is set so that $w_p=1$). The $Hd_p$ are tuned so that $N_d=16$ and $k_p=p$ for $p=1 \ldots N$.

| Band Designation | Range of p |
|---|---|
| "Noise" | 1-5 |
| "40 Hz" | 6-8 |
| "20 Hz" | 9-14 |
| "10 Hz" | 16-28 |
| "5 Hz" | 36-49 |
| "2.5 Hz" | 82-99 |
| "1.25 Hz" | 191-249 |

The component bands for this example implementation are thus the seven composite bands formed from the respective sums of filter sections. The band designations for these component bands are based upon the approximate center frequency of the composite bands resulting from the corresponding ranges of p and assuming a sample rate of 500 Hz. One may note that this Program example does not use all filter section outputs $y_p$, and, in theory, leaves small holes in the continuous spectrum. This is not problematic provided the component band outputs or filter section outputs, or composite band outputs substantially cover the support of the power spectrum of the original signal. An alternate embodiment would be that the sum of the component outputs represents an acceptable approximation of the original signal.

Figure 11:
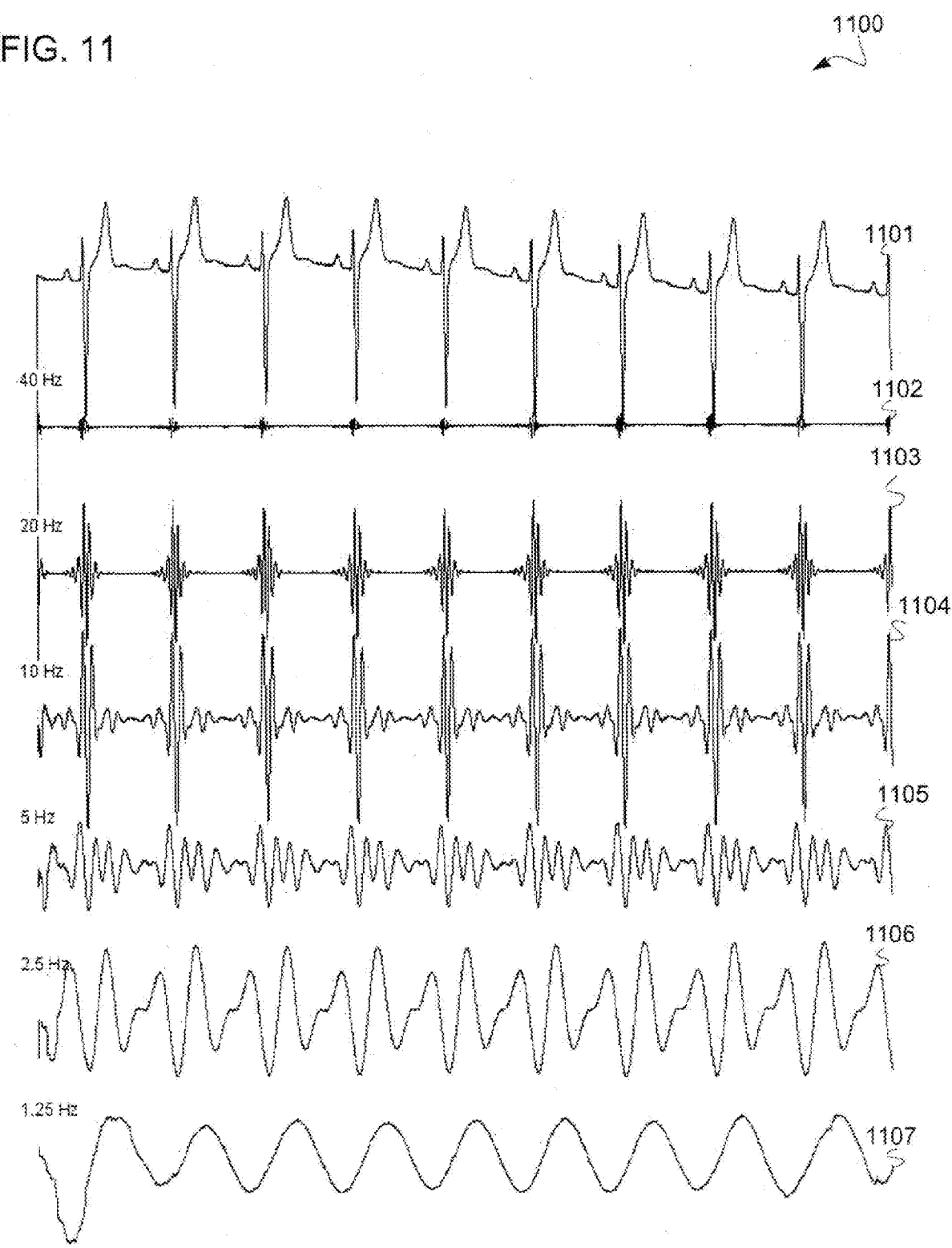
FIG. 11 shows a graphical illustration 1100 of the deconstruction of a normal sinus rhythm (NSR) 1101 into its component waveforms (i.e., Nos. 1102, 1103, 1104, 1105, 1106, 1107).

FIG. 11 shows a graphical illustration of the output data for the Program. In this Figure, a normal sinus rhythm (NSR) 1101 (i.e., the top trace) taken from ECG vector V2 is depicted. The traces below the top trace (i.e., Nos. 1102, 1103, 1104, 1105, 1106, 1107) show the component signals resulting from this original signal corresponding to the outputs of the component bands designated 40 Hz, 20 Hz, 10 Hz, 5 Hz, 2.5 Hz, and 1.25 Hz, respectively.

Figure 12:
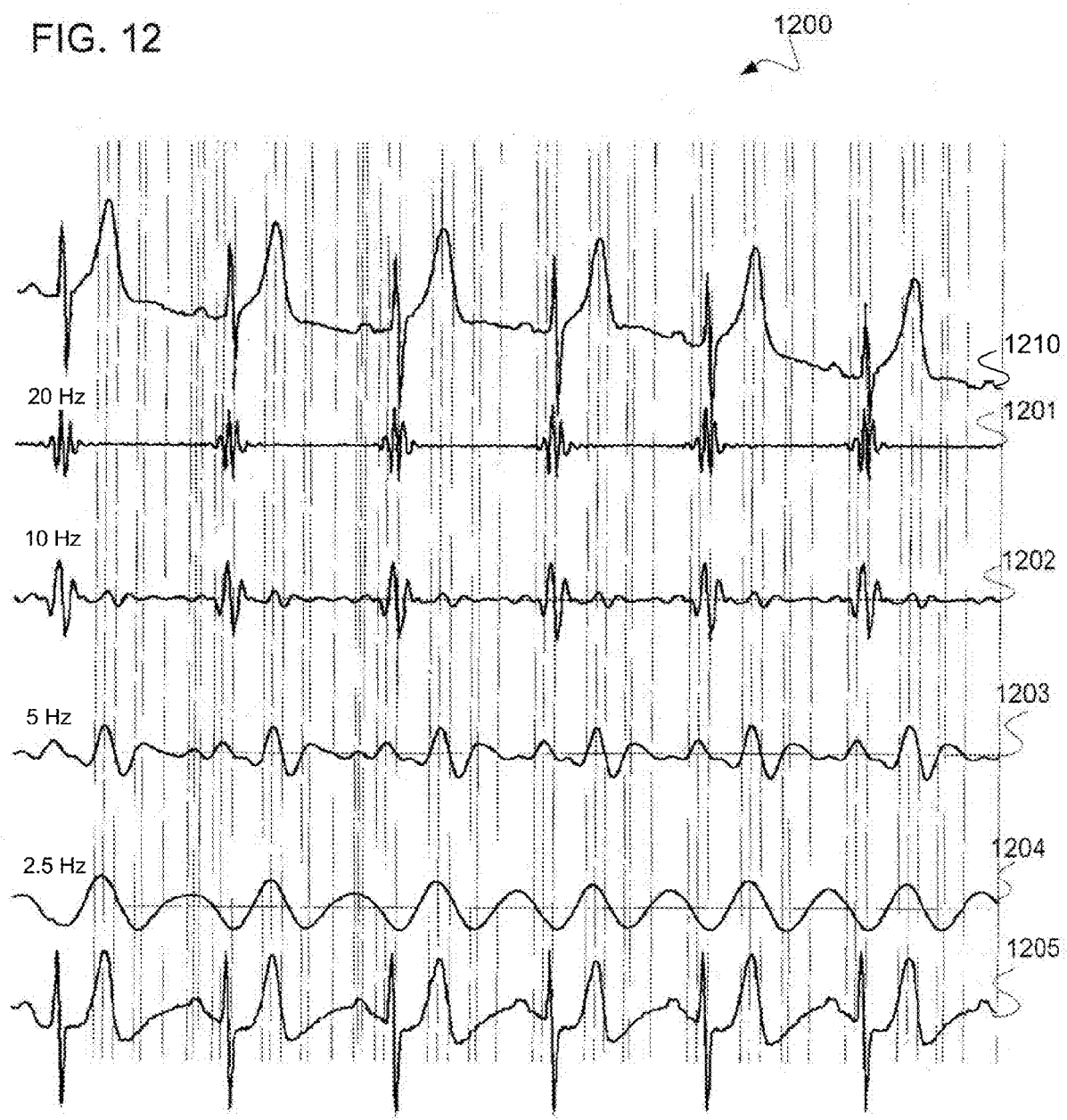
FIG. 12 is a graphical illustration 1200 of the decomposition of another NSR electrocardiogram (ECG), along with a set of resulting component signals, in this case, those from component filters with center frequencies of 20, 10, 5, and 2.5 Hz respectively, from the topmost component trace (i.e., Nos. 1201, 1202, 1203, 1204, and 1205).

FIG. 12 describes the decomposition of another NSR ECG 1210, along with a set of resulting component signals, in this case, those from component bands designated 20, 10, 5, and 2.5 Hz respectively, from the topmost component trace (i.e., Nos. 1201, 1202, 1203, and 1204). In this figure, thin-broken vertical lines are drawn at the beginning of each first, second and third quarter-phase transition of each cycle for the 5 Hz component 1203 (for clarity of viewing, the vertical line is omitted at the beginning of each fourth quarter-phase transition), from which may be observed features on the original signal corresponding to the quarter-phases for this component. A bottom trace 1205 shows the reconstruction resulting from these four components. The thin-broken vertical lines are drawn extending upward through the original signal 1210 and downward through the reconstructed signal 1205, in order to show the corresponding times of the beginning of each first, second and third quarter-phase transition of each cycle of the 5 Hz component signal 1203.

Figure 13:
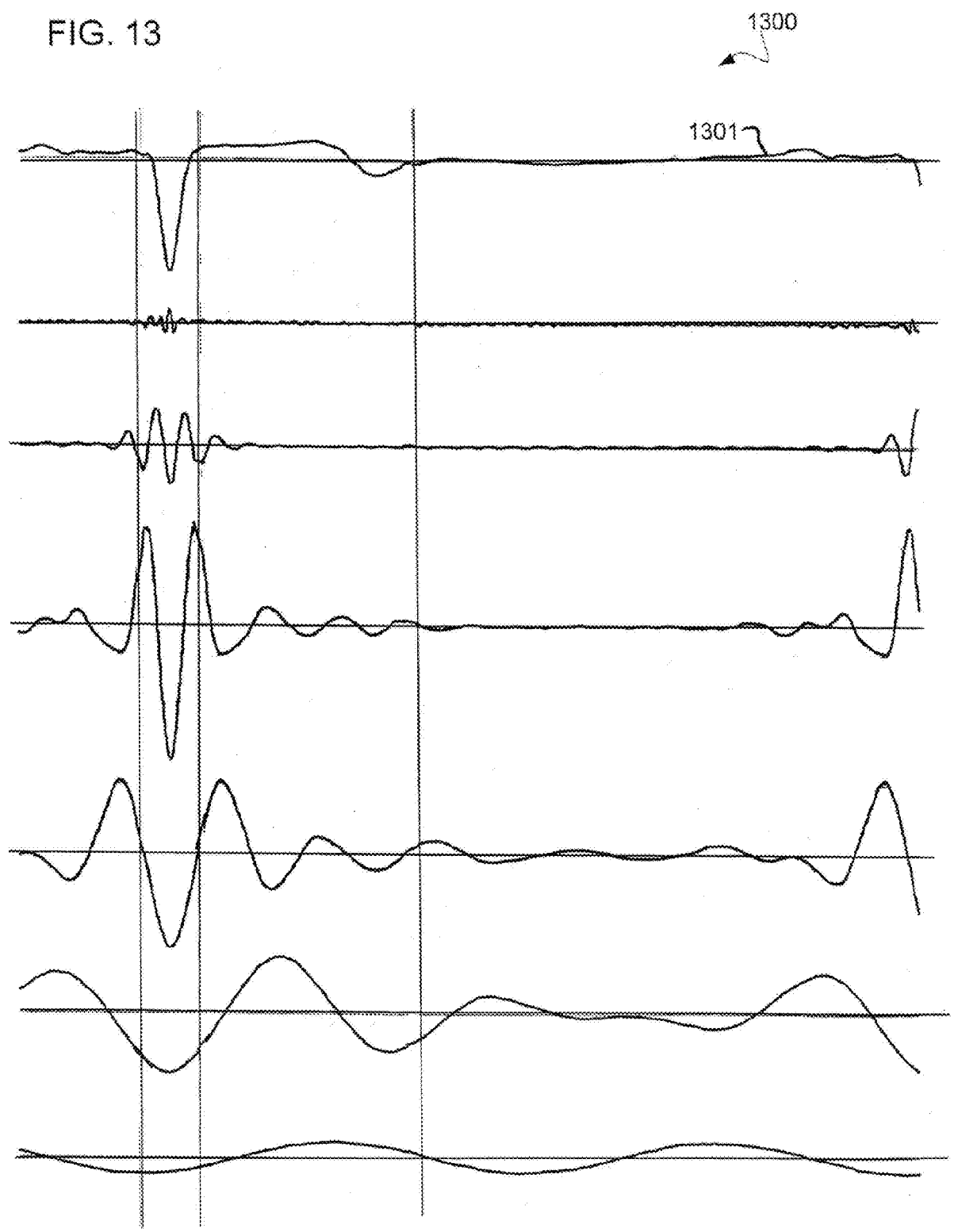
FIG. 13 is an illustration 1300 of an example base quasi-periodic wave and corresponding components, and certain resulting quarter-phases and states of interest that reveal subtle morphological changes from normal ECG morphology due to an abnormal condition, in this case acute myocardial infarction (MI) in a human patient.
Figure 14:
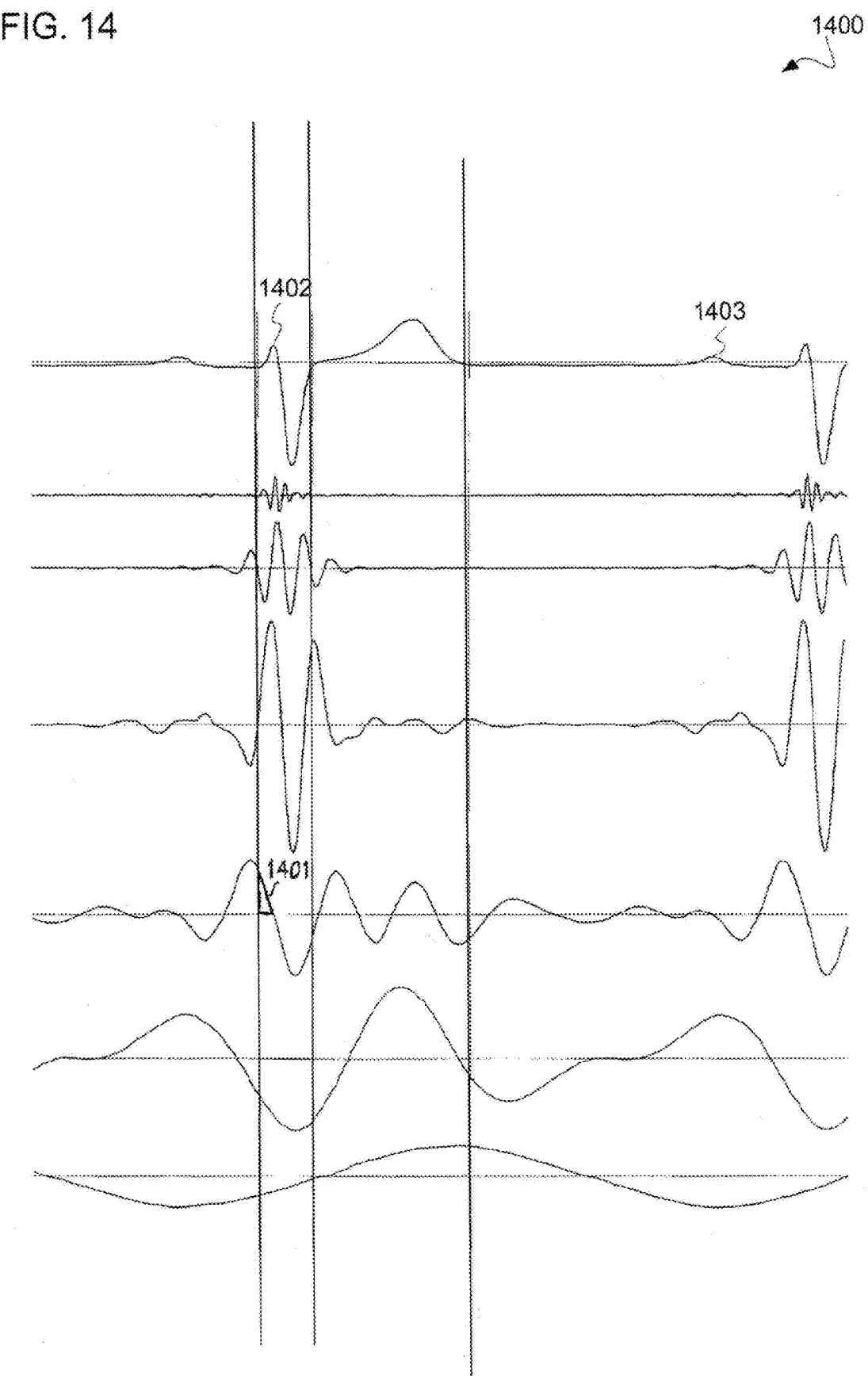
FIG. 14 is an illustration 1400 of an example base quasi-periodic wave and corresponding components, and certain resulting quarter-phases and states of interest, for a normal ECG morphology in a human patient.

FIGS. 13 and 14 illustrate example base quasi-periodic waveforms and corresponding components, and certain resulting quarter-phases and states of interest, that reveal subtle morphological changes from normal ECG morphology due to an abnormal condition, in this case acute myocardial infarction (MI) in a human patient. As before, the traces are arranged such that the ECG is the top trace, and each successive trace below is the component signal arising from a component band designated 40 Hz, 20 Hz, 10 Hz, 5 Hz, 2.5 Hz, or 1.25 Hz, respectively. FIG. 13 corresponds to the MI case and FIG. 14 corresponds to the normal case. Note, particularly in FIG. 14, the region 1401 in the 5 Hz component, which corresponds to the small upward deflection 1402 in the normal ECG trace 1403, and the substantial absence in the MI ECG 1301 of both a region corresponding to this region 1401 and the deflection 1402.

Figure 15A:
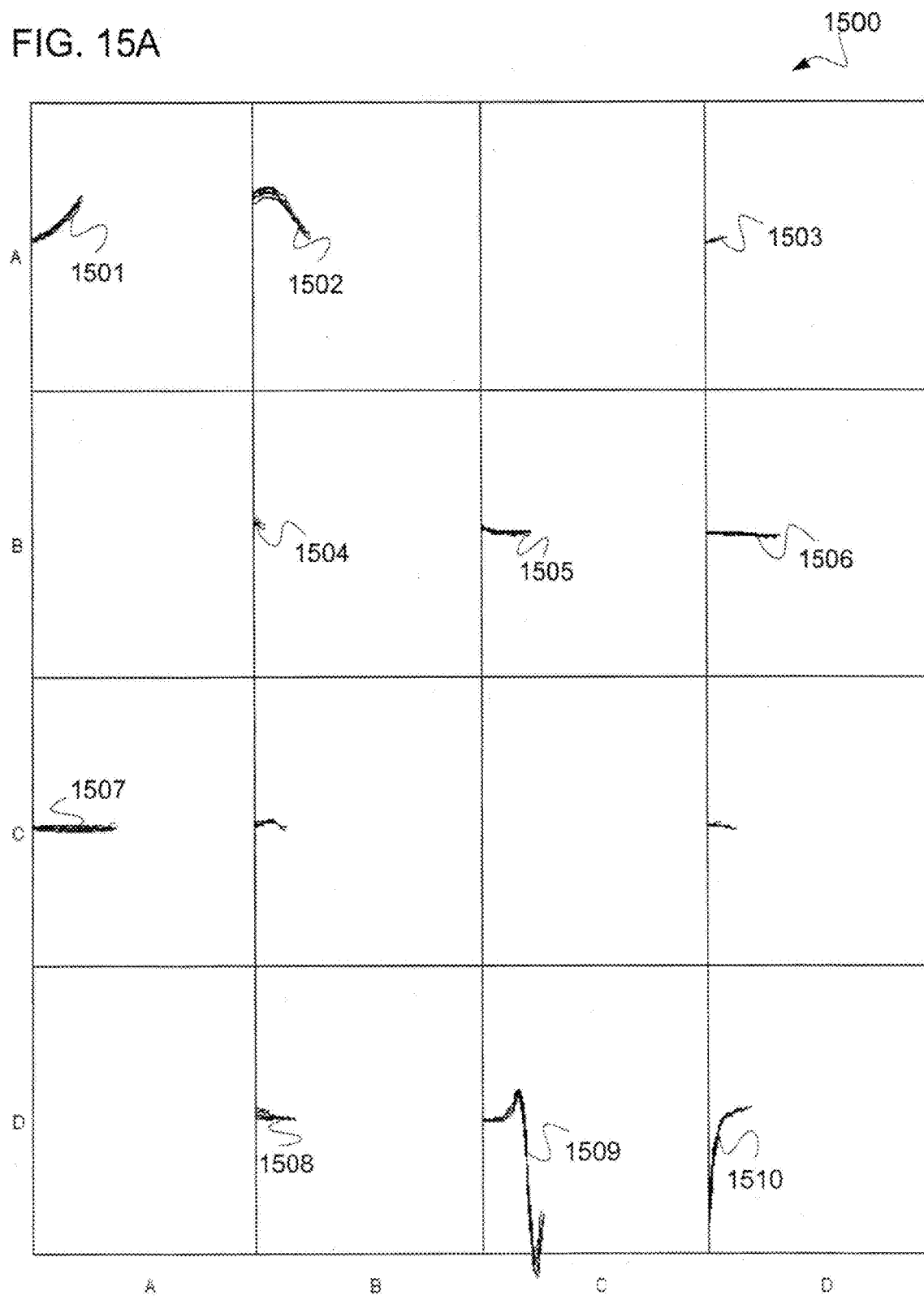
FIG. 15A illustrates a segment 1500 of an original signal ECG and deconstructs this segment by state.

FIG. 15A shows segmentation of the original signal ECG by state. Each box represents one member of the set of 16 possible states corresponding to the quarter-phase objects from the 1.25 and 2.5 Hz components (i.e., component waves). Many of the boxes shown here such as reference numbers 1501, 1502, 1503, 1504, 1505, 1506, 1507, 1508, 1509, and 1510, each contain a plurality of trace segments. Each trace segment represents a piece of the original quasi-periodic waveform associated with a respective one of the states. Within each box, corresponding trace segments arising from each of a plurality of depolarizations of the heart are overlaid one on top of another, resulting in a composite trace. Inside some of the boxes (i.e., reference numbers 1501-1510), vertical ECG deflection is depicted and indexed bottom to top, and forward time is indexed left to right (i.e., each box represents a piece, or slice, of the original signal). While a particular state is active, the original signal is traced in value and time within the corresponding box. The trace starts at the left of the corresponding box (e.g., 1501), at the time that the corresponding state becomes active and ends when the state transitions to another state. When that particular state is entered again (e.g., during the following cardiac cycle), the trace is overlaid on top of the previous trace. Thus, good segmentation is indicated by consistent traces over many similar cardiac cycles, indicating that the states truly capture a unique local morphological characteristic in the original signal.

Figure 15B:
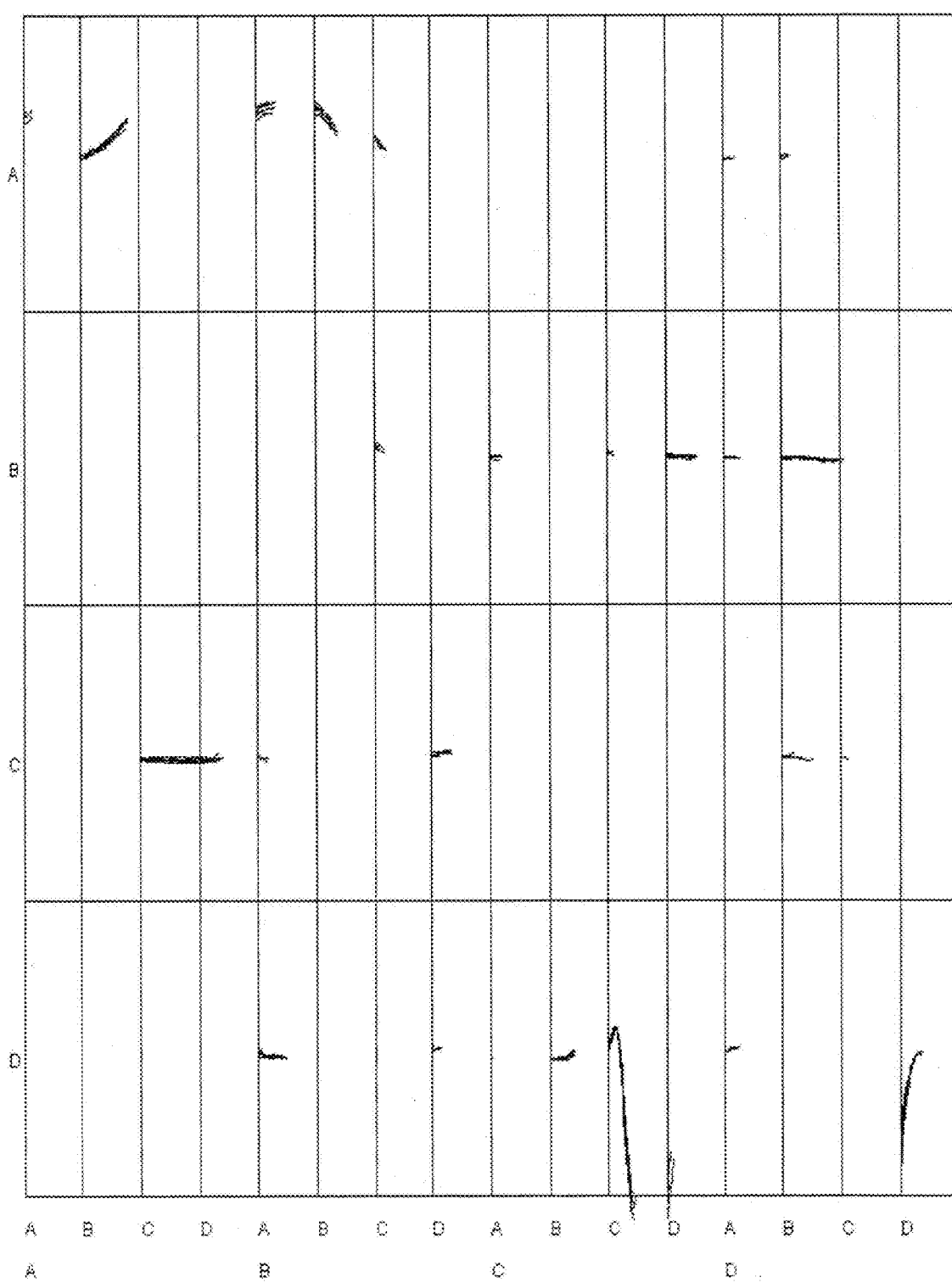
FIG. 15B illustrate a segment 1500 at progressively higher state resolution of 64, by adding states available due to quarter-phase objects from the 5 Hz component.
Figure 15C:
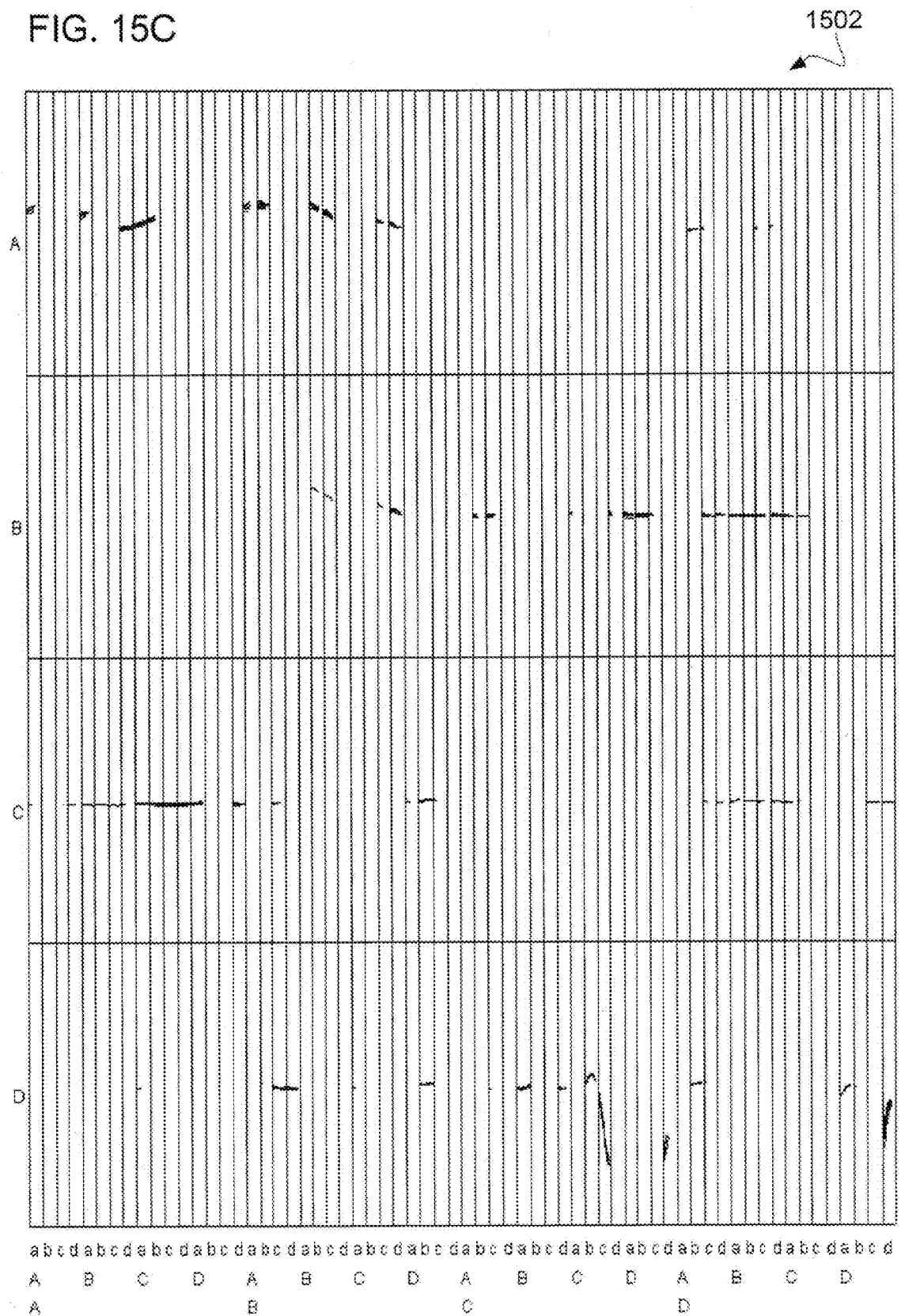
FIG. 15C illustrates a segment 1500 at progressively higher resolution of 256, by adding states available due to quarter-phase objects from the 10 Hz component.

FIGS. 15B and 15C illustrate a consistent segmentation at progressively higher state resolutions of 64 and 256 respectively. This higher resolution is achieved by including higher-frequency component objects and their corresponding states.

Figure 16:
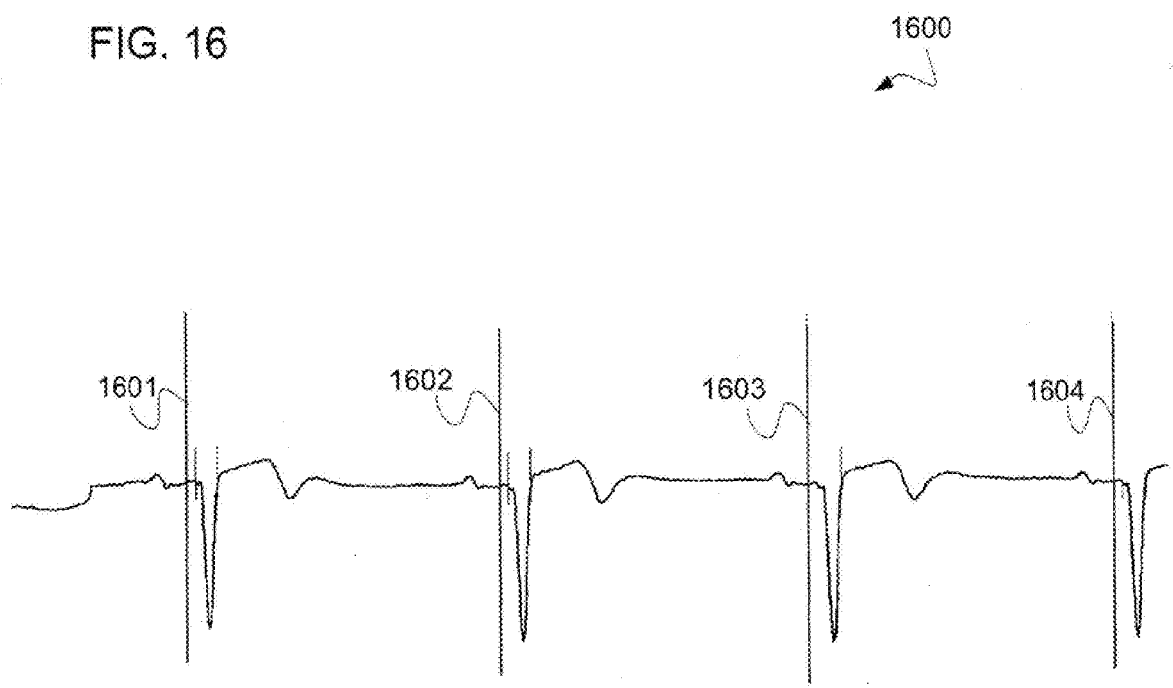
FIG. 16 illustrates an ad-hoc pattern detection method 1600 for detection of the fundamental cardiac cycle and the onset and offset of the QRS complex.

FIG. 16 shows an example of applying ad-hoc pattern detection methods for detection of the fundamental cardiac cycle and the onset and offset of the QRS complex. Here, markers (i.e., Nos. 1601, 1062, 1603, 1604) were placed on the transition to particular states corresponding to the fundamental cardiac cycle, with the added qualification of an object amplitude criterion (i.e., a component active criterion) to reduce spurious generation of markers.

With regard to the structure of the Program itself, the Program contains the following modules and classes in addition to those supplied with MFC. A Readcse.cpp is implemented that reads in ECG from a file. A Leadband class is utilized that performs ECG signal band decomposition for each of the six (6) frequency bands (i.e., designated 1.25, 2.5, 5, 10, 20 and 40 Hz; see FIG. 10A.). Next, a Qatband class is employed to perform ECG band analysis of each of these six (6) frequency bands. Finally a Readband.cpp and Readqat.cpp files are utilized to display the decomposition and analysis results. (E.g., see Attachment C of Provisional Patent Application 60/656,630 referenced above.)

As to the specifics of each of these modules and classes, Readcse.cpp typically reads in binary data from a file. The Leadband class then decomposes this binary data (i.e., a base waveform) into various component waveforms using the cascade-form filter described in FIG. 5. Then, the data relating to these component waves (e.g., a 805, T4 802, 1 803) is used to fill the various data structures described in FIGS. 8A, FIG. 8B and 8C. These data structures are implemented in the qatband class. Lastly, these data structures are displayed graphically via either the Readband.cpp or Readqat.cpp files.

In the present example of the Program, the input file of the ECG data ("D_00004.DCD") contains 10 seconds of the ECG records for a 12 leads standard ECG. Only one lead V2 has been used in the example. Two output files are generated by the program: d0004_7.wbd and d0004_7.qat. D0004_7.wbd displays the results of the ECG decomposition into 6 frequency bands from 1.25 to 40 Hz, while d0004_7.qat displays the results of the ECG quarter-phase analysis (i.e., states).

Figure 17:
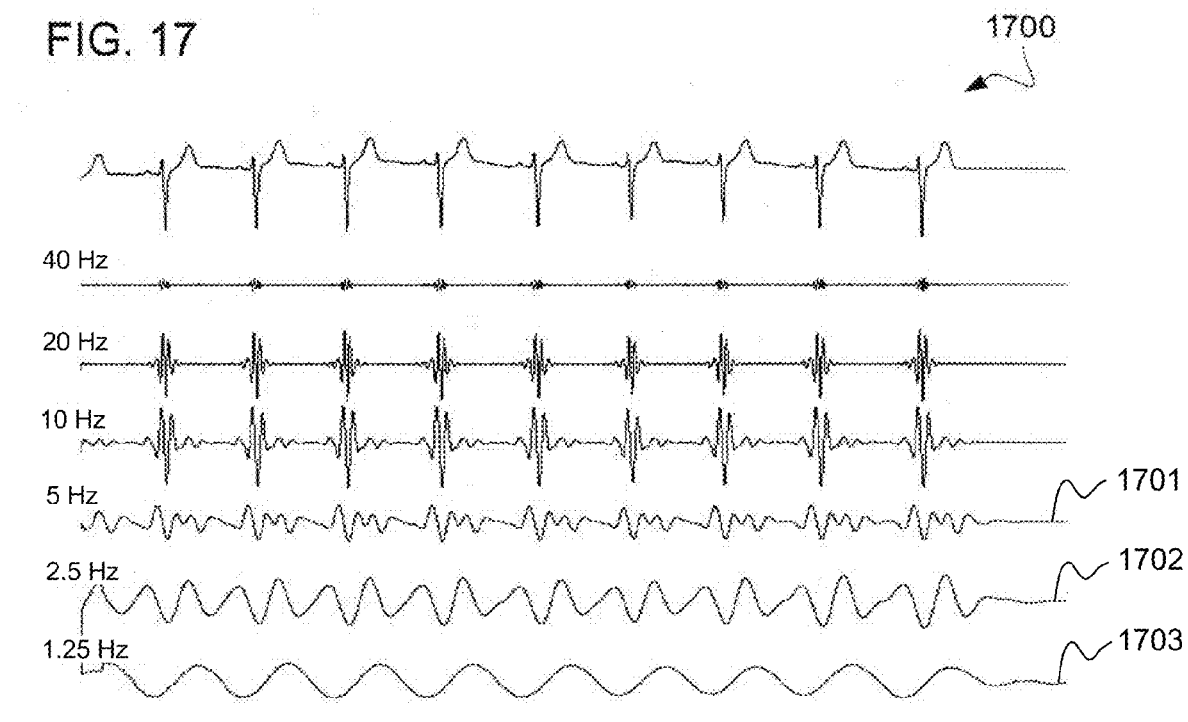
FIG. 17 depicts a method 1700 of displaying the decomposition of an ECG lead V2 into 6 frequency bands.

FIG. 17 displays the decomposition of ECG lead V2 into 6 frequency bands (See FIG. 10A.).

Figure 18:
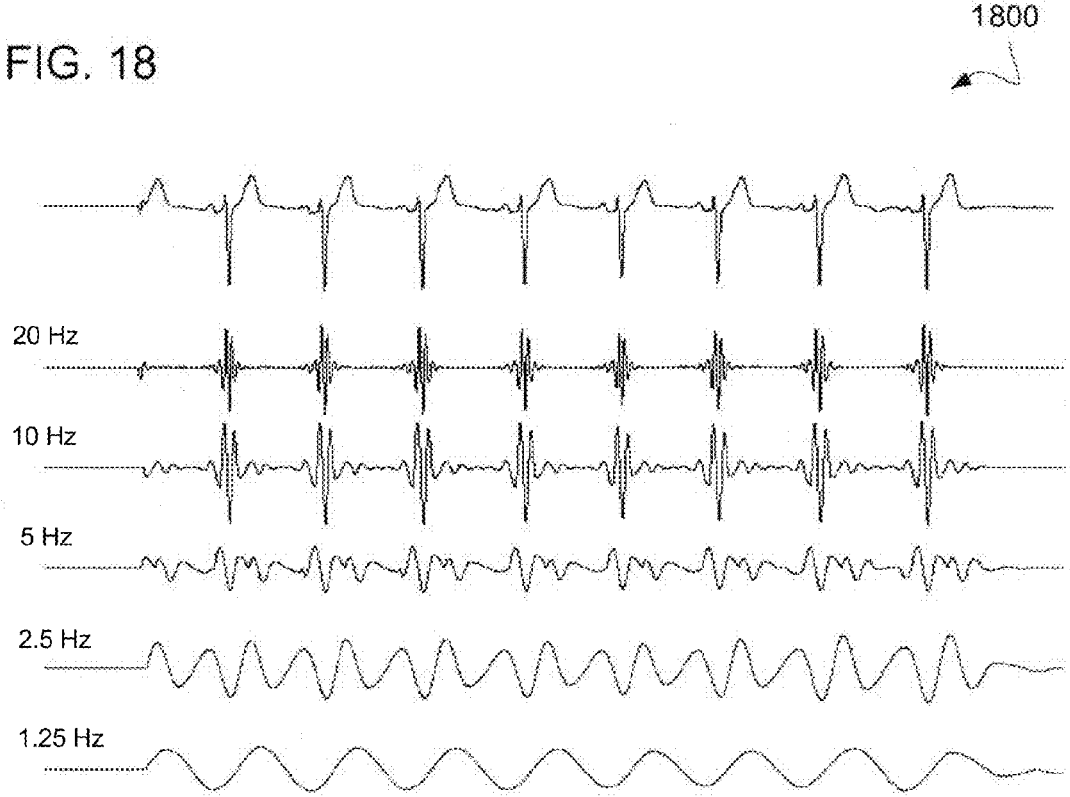
FIG. 18 is an illustration of method 1800 of displaying the reconstruction of an ECG base wave from the state objects data.

FIG. 18 illustrates the reconstruction of the various components and the ECG data from the states and objects.

Figure 19:
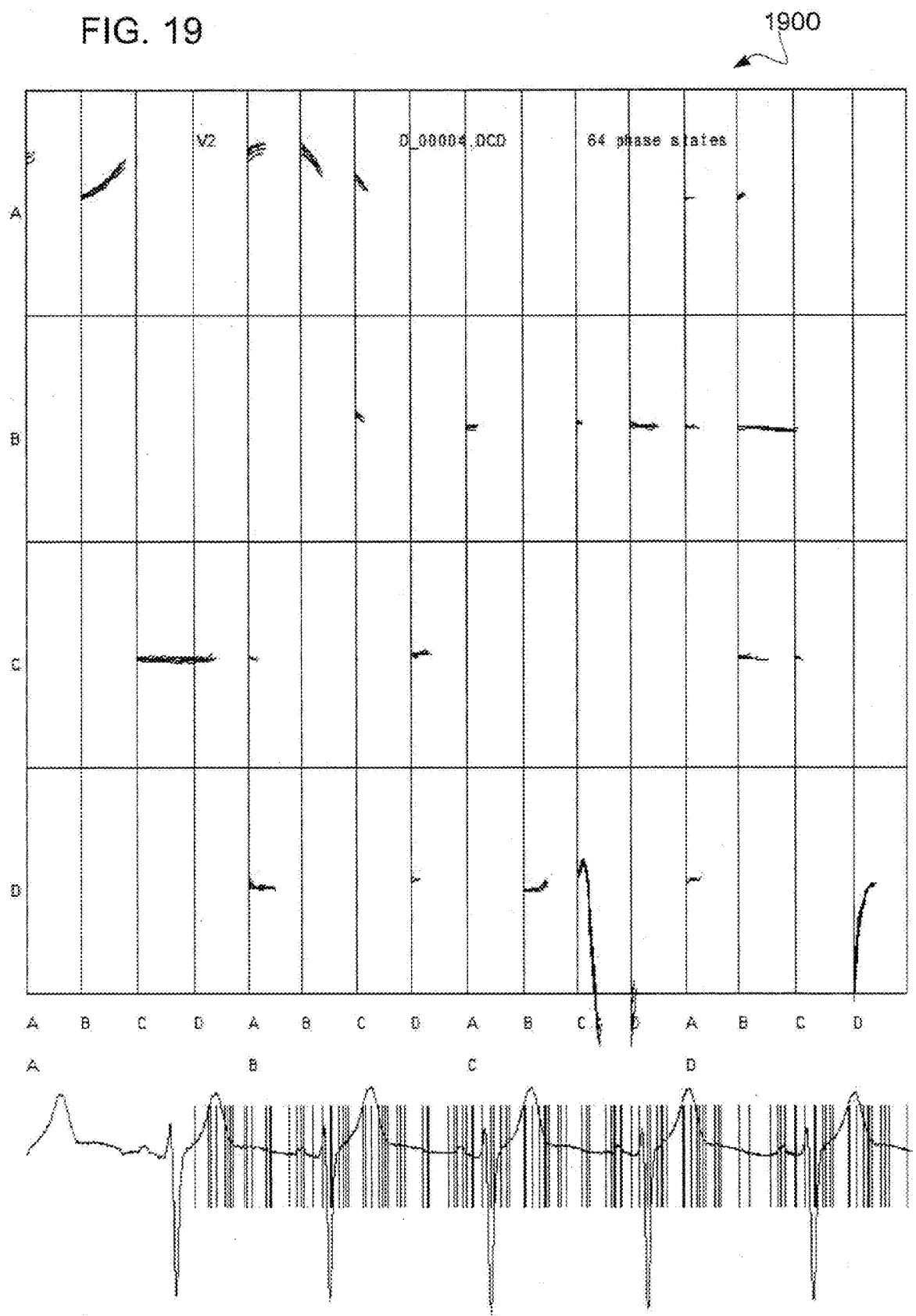
FIG. 19 depicts a matrix representation of output for the original signal ECG and deconstructs this segment by state. Each box represents one member of the set of 64 possible states corresponding to the quarter-phase objects from the three lowest frequency components (i.e., Nos. 1701, 1702, 1703). Many of the boxes each contain sets of line segments overlaid, arising from multiple depolarizations of the heart.

FIG. 19 depicts the output of the program for the three lowest frequency components (i.e., 1701, 1702, 1703 of FIG. 17) in the form of a transition matrix of 64 states.

A Hardware Implementation of the Above Method Using A Multiplierless Architecture In some embodiments, the above described filter banks (i.e., parallel and cascading filter banks) can be implemented using a multiplierless architecture. A multiplerless architecture is well known in the art and typically uses a series of adders, such as ripple-carry adders (RCA) or carry-save adders (CSA), to perform multiplication operations. (See *Design of Multiplerless, High-Performance, Wavelet Filter Banks with Image Compression Applications*, by K. Kotteri, A. Bell, and J. E. Carletta, IEEE Transactions on Circuits and Systems, Vol. 51 No. 3, March 2004; *Multiplierless Approximation of Transform with Adder Constraints*, by Ying-Jui Chen, IEEE Signal Processing Letters, Vol. 9 No. 11, November 2002.) The advantage of such an architecture is that it is relatively small and as such can be implemented in small devices needing relatively smaller power supplies. In some embodiments, such an architecture would use embedded circuits to implement the functionality of the filter banks, whereas in other embodiments some type of firmware implementation would be utilized to represent the functionality of the filter banks.

Such a multiplierless architecture could be designed using VHSIC Hardware Description Language (VHDL). By using VHDL the logic of both the filter and the multiplierless architecture used to create a hardware implementation of a filter could be determined. This logic could then be used to implement an embedded hardware example of the VHDL code. The use of VHDL to design and implement an embedded hardware configuration including filter banks is well known in the art. (See *VHDL: Programming By Example* 4th *Edition*, by Douglas L. Perry, McGraw-Hill Professional, 2002.)

System Description Utilizing the Above Method, Data Structure, or Program

As a threshold matter, the above-described method, data structure or program can be used in conjunction with any qp waveform. In some embodiments, this is a qp wave in the form of ECG data, while in other embodiments it might be another type of qp waveform. With regard to qp waveforms derived from ECG data, any system that obtains ECG data from, for example, a set of electrodes could employ the above outlined method, data structure or program.

Figure 20:
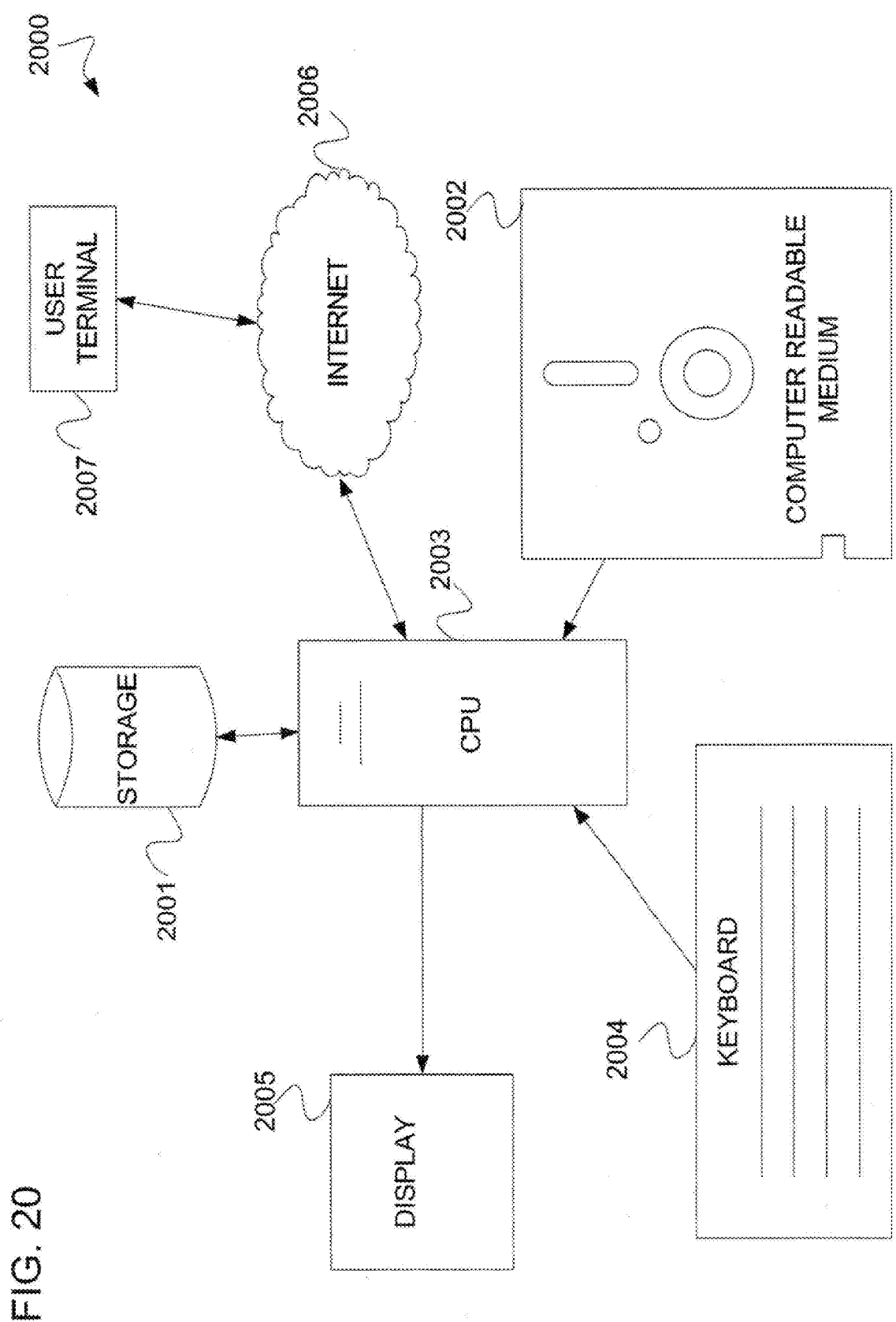
FIG. 20 is a block diagram of a system 2000 wherein data related to a qp waveform is stored in a database 2001.

FIG. 20 is a block diagram of a system 2000 wherein data related to qp waveforms ("Data") is stored in a data base 2001. This Data serves as input for a computer program utilizing the above-described method, data structure and/or program contained on a computer readable medium 2002, and executed by a central processing unit (CPU) 2003. In some embodiments, this CPU is an x86 series CPU, while in other embodiments it is a CPU known in the art. Input to execute the program can, in some embodiments, come by way of a keyboard 2004. In still other embodiments, input to execute the program can come by way of a peripheral device such as a mouse, light pen, touch screen, touch pad or any other input device known in the art. In some embodiments, the described method can be called by another program to execute and process wave data. Once processed, data processed using the above-described method, data structure and/or program can be outputted to a display 2005, or sent via an internet 2006 to another user terminal 2007. In some embodiments, the output can be placed into a database 2001 or another database located off-site.

Figure 21:
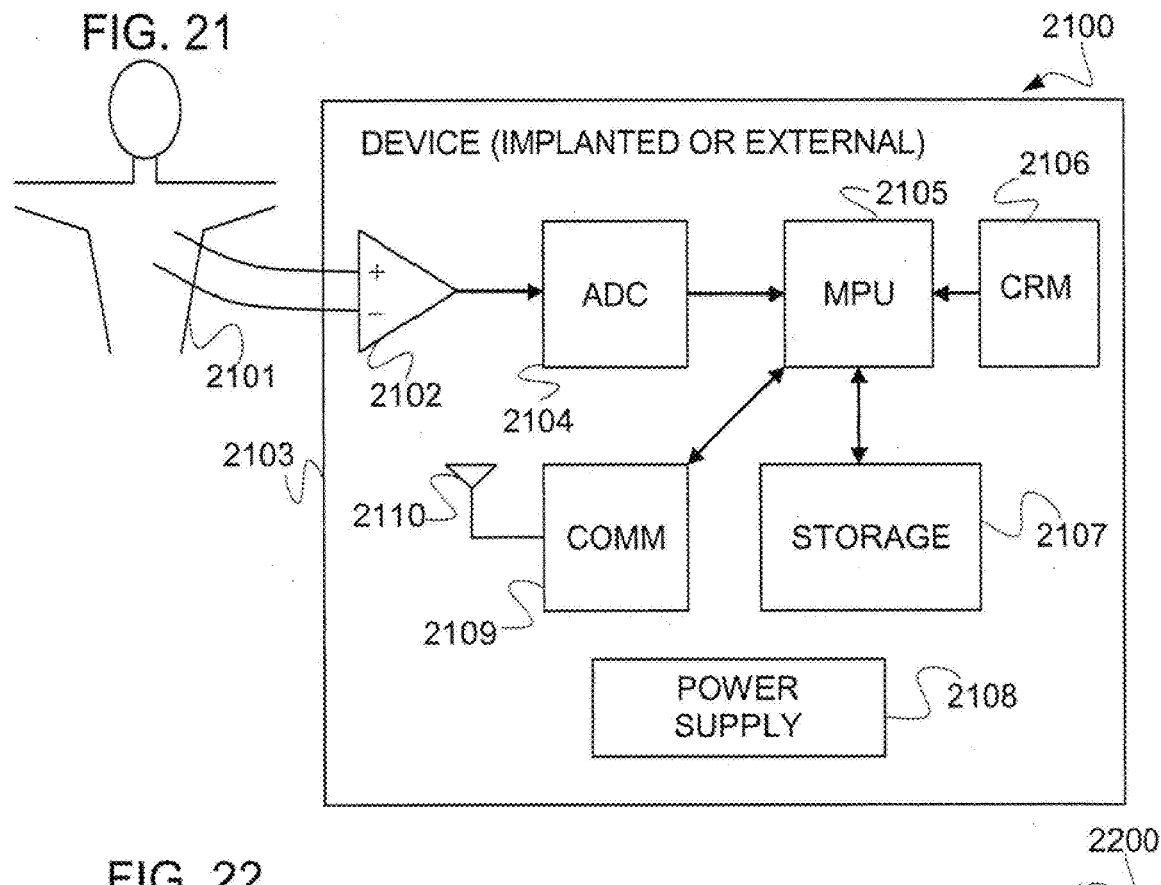
FIG. 21 is a block diagram of a system 2100 wherein the original wave signal is an ECG from a patient 2101 and including an ECG signal collection and processing device 2103.

FIG. 21 is a block diagram of a system 2100 wherein the original wave signal is an ECG. In this system, a set of electrodes 2101 ("leads") is disposed around, on, or within a human body in a manner to produce a desired differential voltage across them representing the voltage gradient generated by the electrical properties of the cardiac tissue. One or more electrodes 2101 may be disposed on the skin surface of the body, underneath the skin surface (i.e., a subcutaneous application), and/or additionally, within the heart (i.e., an intracardiac application). Two electrical poles 2102 ("poles") are formed by tying together two disjoint sets each of one or more such disposed electrodes 2101. The term "vector" is used in this context interchangeably for the directed voltage gradient and/or the simple voltage difference across the poles. The term "leads" is used interchangeably with the poles and/or the leads from which they are constructed, but generally imply a construction of one or more poles from the set of individual leads.

The leads 2101 are connected to a sensing device 2103 ("Device") which is either implanted into the human body or resides external to the human body. The Device 2103 in this example contains a set of units or modules, including a difference amplifier module, an analog to digital converter 2104 ("ADC"), a microprocessor unit 2105 ("MPU"), associated computer readable medium ("CRM") 2106 containing program instructions, memory storage 2107 ("Storage"), and a power source for supplying power 2108 ("Power Supply") to the contained modules. The Device may also contain a communications module 2109 ("Comm") and an associated communications link 2110. This communication module and link, in some embodiments, may have a wireless means of providing ECG data.

The differential voltage existing across the leads is measured and/or sensed by presenting the leads to a difference amplifier 2102. In some embodiments, the difference amplifier is presumed to contain analog filtering sufficient to substantially meet predetermined requirements for signal-to-noise ratio ("SNR") optimization and/or anti-aliasing. In this example, the output of the difference amplifier is digitized using an ADC 2104. The output samples from the ADC 2104 may then be used as the original signal for this invention example. This original signal is passed to the MPU 2105 for processing.

Multiple sensing vectors may be accommodated with multiple lead arrangements, as is well understood and established in the art. (See *An Introduction to Electrocardiography 7$^{th}$ Edition*, by Leo Schamroth, Blackwell Scientific, 1990.) In this case, each differential lead pair could connect to its own processing chain can be defined here to include a difference amplifier followed by an ADC 2104, producing a corresponding original signal for each sensing vector so processed. Each resulting original signal would then be passed to the MPU 2105 for processing.

The MPU 2105 executes software and/or firmware stored on computer readable medium 2106 to perform the various tasks necessary for basic function of the Device, and/or to generally fulfill feature, functionality requirements of the Device. The storage of data values representing the original signal and/or the associated objects can, in some embodiments, be in the storage 2107 or the computer readable medium 2106.

In some embodiments, the communications module 2109 is used to send outgoing transmissions from the Device 2103 to a Host 2201 for further processing, evaluation, storage and/or transmission to other similar or different Hosts on a network. The communications module 2109 is also used to receive incoming transmissions from a Host 2201, which may be the same as or distinct from the Host 2201 used for outgoing transmissions. In some embodiments, incoming transmissions may include commands, data, and/or firmware/software updates as necessary to perform the basic function of the Device 2103, and/or to generally fulfill feature requirements of the Device 2103. For an implanted Device 2103, the connection between the communications module 2109 and a Host 2201 would be typically implemented in wireless fashion, using methods including but not limited to magnetic, capacitive, and/or RF, all well understood and established in the art. (See *Principles of Wireless Networks: A Unified Approach 1$^{st}$ Edition*, by Kaveh Pahlavan, Prashant Krishnamurthy, Prentice Hall, 2001.) For an external Device, the connection may be wireless or wired using methods also well understood and established in the art.

Figure 22:
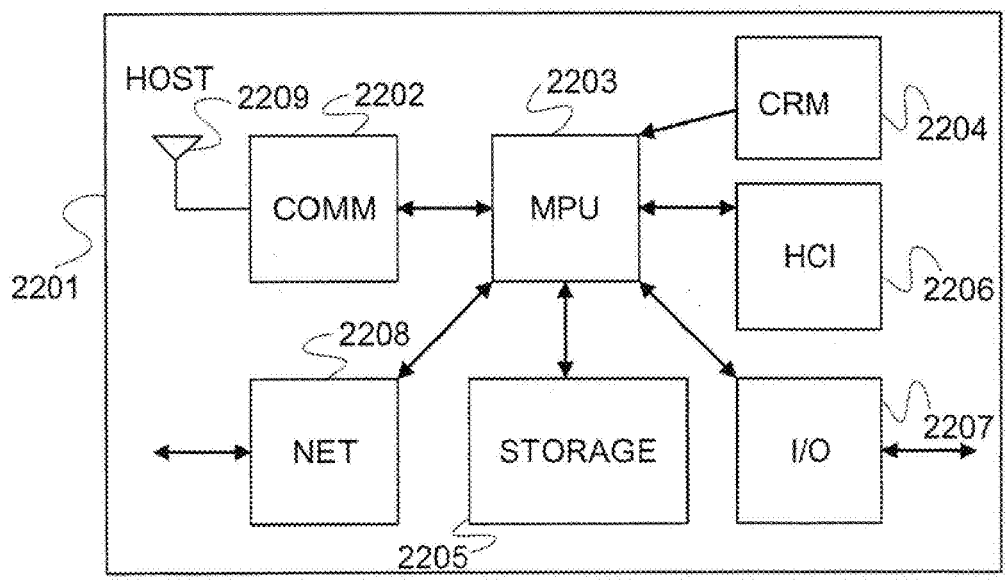
FIG. 22 is a block diagram of a system 2200 that depicts a host 2201.

FIG. 22 is a block diagram of a system 2200 that depicts a Host 2201 which may, in some embodiments, include a set of units or modules such as a communications module 2202 ("Comm") and associated communications link 2209 for communicating with the Device 2103, a microprocessor unit 2203 (MPU) including a computer readable medium 2204 containing a set of application instructions, an associated storage module 2205 ("Storage) containing data values representing the original signal, a Human-Computer Interface 2206 ("HCI") by which an operator (e.g., a physician, technician, or patient) may interact with the MPU 2203 and which may include a visual display, auditory display, keyboard, mouse, touch screen, haptic device, or other means of interaction. Also described is an Input/Output module 2207 ("I/O") for generally connecting to, and communicating with, computer peripherals such as for example printers, scanners, and/or data acquisition or imaging equipment, and a network communications module 2208 ("Net") for communicating with other Hosts on a computer network such as Ethenet and/or a wireless network, or WiFi. A Power Supply unit is not drawn for the Host as such a unit may exist entirely within any or all of the individual modules, and so is assumed to exist in the Host system as needed.

FIG. 23 is a block diagram of a system 2300. In some embodiments, the Input/Analysis Process block 2301 takes the original signal and produces a corresponding stream of objects. The original signal is applied to the Signal Decomposition block 2302, the output of which is the set of corresponding component signals. These signals are then processed in the Fractional Phase Representation block 2303 to identify the object boundaries and measure basic attributes, and the corresponding object-related information is passed to the Object Construction and Linking block 2304 to construct the object streams, filling out whatever additional object-related, data structure related information (i.e., attributes, links, etc.) is needed in a particular application. In cases of multiple original signals, the Input/Analysis Process block would be repeated and/or duplicated for each original signal. The resulting object streams from each Process may then be merged into a single composite stream of objects.

The Interpretive Process block 2305 takes the object stream and produces an interpretation of the original signal (s). In some embodiments, the State Construction block 2306 takes the object stream and constructs states from them. The resulting series of states, along with the underlying objects by which they are defined, then form the input to the Organized Mapping block 2307, where the information is mapped in state space and/or a vector space along one or more object attributes. As stated in the context of this invention, the information may be mapped directly in some ad-hoc manner, for example using a sequence detector on the states and/or some nonlinear, neural and/or fuzzy map formed on the object attributes. In some embodiments, the information may also be used for training a model such as an HMM and/or NN. Once trained, the information may be applied to the model to produce a mapped output. In some embodiments, the mapped information is then passed to a Pattern Recognition, Discrimination and/or Display block 2308 to transform the mapped information into a human-interpretable form, such as for example an automated identification and/or diagnosis of a certain condition, and/or visualization of relevant mapped information. Automated identification could involve simple thresholding on the mapped information, or could use more sophisticated detection and discrimination techniques such as Novelty Detection and Support Vector Machines. (See *The Nature of Statistical Learning Theory $2^{nd}$ Edition*, by V. Vapnik, Springer 1995; *Support-Vector Learning*, by C. Cortes and V. Vapnik, 20 Machine Learning 1995.)

The Storage/Transmission block 2309 takes the object stream and/or the original signal samples and/or samples of the component signals (or a predetermined select subset of the component signals) and stores some or all of them in memory and/or transmits some or all of them over a communications link. The Resynthesis/Output Process block 2310 takes the object stream from a communications link and/or storage and reconstructs an estimate of the original signal(s). The object stream corresponding to a desired original signal is recovered from storage and/or received from a communications link via the Retrieval/Reception block 2311. Estimates of the component signals for the desired original signal are then produced by the Component Reconstruction block 2312, and the component signal estimates are then combined in the Signal Reconstruction block 2313 to produce an estimate of the desired original signal. If desired, the individual component signals may be output from the Resynthesis/Output Process block 2310 as well. Multiple original signals may be reconstructed using multiple instances of this Process, once for each desired original signal. The reconstructed signal(s) may then be displayed, for example, on a plot trace (or series of plot traces) for human interpretation, if desired, along with the output of the Interpretive Process block 2305.

In some embodiments, device 2103 performs no signal analysis processes except for the process of Storage/Transmission. The original signal samples are merely passed to the communications module 2109 of the Device, either directly or perhaps via the MPU 2105, perhaps with some formatting of the data for optimal transmission. The Host 2201 then performs some or all of the remainder of the signal analysis processes.

In some embodiments, device 2103 performs the Input analysis and the Storage/Transmission Processes, and the Host 2201 performs some or all of the remainder of the processes. In the case that the component signals and/or the original signal are not transmitted to the Host 2201, they may be estimated on the Host end from the transmitted objects via the Resynthesis/Output Process block 2310.

In some embodiments, the signal analysis processes are performed, in whole or in part, by execution of software or firmware on the MPU 2105 and/or on the MPU 2203, using a program stored in the appropriate respective computer readable medium 2204 and/or storage unit 2205. Such processing may also be performed, in whole or in part, in dedicated hardware which in this example resides entirely within the MPU 2105 and/or on the MPU 2203, for example in the form of microcode, in the form of a coprocessor, and/or in the form of peripheral hardware.

In some embodiments, the invention provides a method that includes: receiving a series of digital values representing a quasi-periodic waveform, decomposing the series of digital values into a plurality of component signals, wherein each component signal includes a series of digital values that are obtained using a cascade of additive linear combinations of substantially equal-magnitude versions of at least two of the digital values of the quasi-periodic waveform, and storing the component signals.

In some embodiments, the linear combinations use coefficients with equal magnitudes but opposite sign, applied to each of two of the digital values.

In some embodiments, the linear combinations use coefficients with equal magnitudes and signs applied to each of the two or more of the digital values of the quasi-periodic waveform.

In some embodiments, the coefficients are applied to sequential digital values separated from one another by a scaling factor.

In some embodiments, the sequential digital values enter into the linear combination, the number of values determined by a scaling factor.

In some embodiments, the series of values for each component signal represents a digitally filtered frequency-limited band of the quasi-periodic waveform.

In some embodiments, the digitally filtered frequency-limited band is selected based on frequency content of the quasi-periodic waveform.

In some embodiments, the series of values for each component signal include complex numbers and represent an analytic signal.

In some embodiments, the quasi-periodic waveform includes a time-varying physiological signal obtained from a mammal, and the series of digital values for each component signal represents a digitally filtered frequency-limited band of the quasi-periodic waveform.

In some embodiments, the quasi-periodic waveform includes an electrocardiogram (ECG) signal from a human, and the series of digital values for each component signal represents a digitally filtered frequency-limited band of the ECG signal.

Some embodiments further include transforming each of the component signals to obtain: a plurality of independent ordinate values, and a plurality of abscissa values each associated with a corresponding ordinate value. Each ordinate value is based on an amplitude metric. Each abscissa value is based on a time metric.

In some embodiments, transforming of each component signal further includes: a phase adjustment value such that a linear combination of the component signals substantially reconstructs the quasi-periodic waveform.

Some embodiments further include transforming of each component signal further includes: an amplitude adjustment value such that a linear combination of the component signals substantially reconstructs the quasi-periodic waveform.

Some embodiments further include transforming of each component signal uses a multiplierless architecture.

In some embodiments, the component signals are obtained by applying a Parallel-Form Kovtun-Ricci Wavelet Transform to the series of digital values.

In some embodiments, the component signals are obtained by applying a Cascade-Form Kovtun-Ricci Wavelet Transform to the series of digital values.

In some embodiments of the invention, a computer-readable medium is employed having executable instructions stored thereon for causing a suitable programmed central processing unit to perform a method that includes: obtaining a series of digital values representing a quasi-periodic waveform, decomposing the series of digital values into a plurality of component signals, wherein each component signal includes a series of digital values that are obtained using a cascade of additive linear combinations of substantially equal-magnitude versions of at least two of the digital values, and storing the component signals.

In some embodiments, the computer-readable medium includes further instructions configured for the linear combination to use coefficients with equal magnitudes but opposite sign, applied to each of two of the digital values.

In some embodiments, the computer-readable medium includes further instructions configured for the linear combination to use coefficients with equal magnitude and sign applied to each of the two or more of the digital values.

In some embodiments, the computer-readable medium includes further instructions configured for the coefficients to be applied to sequential digital values separated from one another by a scaling factor.

In some embodiments, the computer-readable medium includes further instructions configured for the sequential digital values to be entered into the linear combination, with the number of values determined by a scaling factor.

In some embodiments, the computer-readable medium includes further instructions configured for the series of values for each component signal to represent a digitally filtered frequency-limited band of the quasi-periodic waveform.

In some embodiments, the computer-readable medium includes further instructions configured for the digitally filtered frequency-limited band to be chosen corresponding to a frequency content of the quasi-periodic waveform.

In some embodiments, the computer-readable medium includes further instructions configured for the series of values for each component signal to represent an analytic signal.

In some embodiments, the computer-readable medium includes further instructions configured for the quasi-periodic waveform to be a time-varying physiological signal obtained from a mammal, and the series of digital values for each component signal represent a digitally filtered frequency-limited band of the quasi-periodic waveform.

In some embodiments, the computer-readable medium includes further instructions configured for the quasi-periodic waveform to be an electrocardiogram (ECG) signal from a human, and the series of digital values for each component signal represent a digitally filtered frequency-limited band of the ECG signal.

In some embodiments, the computer-readable medium includes further instructions for transforming each of the component signals to obtain: a plurality of independent ordinate values, and a plurality of abscissa values each associated with a corresponding ordinate value.

In some embodiments, the computer-readable medium includes further instructions configured for each ordinate value to be based on an amplitude metric.

In some embodiments, the computer-readable medium includes further instructions configured for each abscissa value to be based on a time metric.

In some embodiments, the computer-readable medium includes further instructions configured for the transforming of each component signal including: a phase adjustment value such that a linear combination of the component signals substantially reconstructs the quasi-periodic waveform.

In some embodiments, the computer-readable medium includes further instructions configured for the transforming of each component signal including: an amplitude adjustment value such that a linear combination of the component signals substantially reconstructs the quasi-periodic waveform.

In some embodiments, the computer-readable medium includes further instructions for transforming of each component signals using a multiplierless architecture.

In some embodiments, the computer-readable medium includes further instructions configured for the component signals to be obtained by applying a Parallel-Form Kovtun-Ricci Wavelet Transform to the series of digital values.

In some embodiments, the computer-readable medium includes further instructions configured for the component signals to be obtained by applying a Cascade-Form Kovtun-Ricci Wavelet Transform to the series of digital values.

In some embodiments, the invention provides a method that includes obtaining a plurality of component signals representative of a quasi-periodic waveform, wherein each component signal includes a plurality of component values that represent a digitally filtered frequency-limited band of the quasi-periodic waveform, and transforming each of the plurality of component values into a fractional-phase representation including values representing at least one of an abscissa and an ordinate for each of a plurality of fractional phases per local cycle of the component signal, and storing the fractional-phase representation. In some embodiments, each ordinate value is based on an amplitude metric. In some embodiments, each abscissa value is based on a time metric.

In some embodiments, each fractional-phase representation includes a phase adjustment value such that a linear combination of the plurality of component values substantially reconstructs the quasi-periodic waveform.

In some embodiments, each fractional-phase representation includes an amplitude normalization value such that a linear combination of the plurality of component values substantially reconstructs the quasi-periodic waveform.

In some embodiments, the component signal includes a first fractional phase, a second fractional phase, a third fractional phase, and a fourth fractional phase, wherein: the fractional-phase representation for the first fractional phase includes a value representing an abscissa associated with a zero crossing of the associated component signal, the fractional-phase representation for the second fractional phase includes a value representing an ordinate and a value representing an abscissa both values representing an abscissa and values representing an ordinate associated with a maximum of the associated component signal, the fractional-phase representation for the third fractional phase includes a value representing an abscissa associated with another zero crossing of the associated component signal, and the fractional-phase representation for the fourth fractional phase includes a value representing an ordinate and a value representing an abscissa both associated with a minimum of the associated component signal. Each ordinate value is based on an amplitude metric. Each abscissa value is based on a time metric. Each fractional-phase representation includes a phase adjustment value such that a linear combination of the plurality of component values substantially reconstructs the quasi-periodic waveform. Each fractional-phase representation includes an amplitude normalization value such that a linear combination of the plurality of component values substantially reconstructs the quasi-periodic waveform.

In some embodiments, the plurality of component values for each component signal are complex-valued, wherein the fractional-phase representation for each fractional phase includes a value representing an ordinate, a value representing an abscissa, or both values representing an abscissa and values representing an ordinate associated with an angular range of a complex argument of an associated analytic component signal.

In some embodiments, each ordinate value includes an amplitude metric selected from a group consisting of: a complex magnitude, a real part, and an imaginary part of the analytic component signal.

In some embodiments, each ordinate value includes an amplitude metric based upon: the complex magnitude of the analytic component signal, the real part of the analytic component signal, and the imaginary part of the analytic component signal.

In some embodiments, each abscissa value is based on a time metric.

In some embodiments, each fractional phase representation includes a phase adjustment value such that a linear combination of the plurality of component values substantially reconstructs the quasi-periodic waveform.

In some embodiments, each fractional-phase representation includes an amplitude normalization value such that a linear combination of the plurality of component values substantially reconstructs the quasi-periodic waveform.

In some embodiments, the number of fractional phases available per local cycle of each component signal is a predetermined number for that component, and wherein the angular ranges for the phases correspond to subdivisions of the angular range of the complex argument.

In some embodiments, each ordinate value is based upon an amplitude metric selected from a group consisting of: a complex magnitude of the analytic component signal, a real part of the analytic component signal, and an imaginary part of the analytic component signal, In some embodiments, each ordinate value is based upon an amplitude metric including: a complex magnitude of the analytic component signal, a real part of the analytic component signal, and an imaginary part of the analytic component signal In some embodiments, each abscissa value is based upon a time metric.

In some embodiments, each fractional-phase representation includes a phase adjustment value such that a linear combination of the plurality of component values substantially reconstructs the quasi-periodic waveform.

In some embodiments, each fractional-phase representation includes an amplitude normalization value such that a linear combination of the plurality of component values substantially reconstructs the quasi-periodic waveform.

In some embodiments, the number of fractional phases available per local cycle of the component signal is four including: a first fractional phase, a second fractional phase, a third fractional phase, and a fourth fractional phase, and wherein: the fractional-phase representation for the first fractional phase includes a value representing an ordinate, a value representing an abscissa, or both values representing an abscissa and values representing an ordinate associated with a zero crossing of a real part of the associated analytic component signal, the fractional-phase representation for the second fractional phase includes a value representing an ordinate, a value representing an abscissa, or both values representing an abscissa and values representing an ordinate associated with a zero crossing of an imaginary part of the associated analytic component signal, the fractional-phase representation for the third fractional phase includes a value representing an ordinate, a value representing an abscissa, or both values representing an abscissa and values representing an ordinate associated with another zero crossing of the real part of the associated analytic component signal, and the fractional-phase representation for the fourth fractional phase includes a value representing an ordinate, a value representing an abscissa, or both values representing an abscissa and values representing an ordinate associated with another zero crossing of the imaginary part of the associated analytic component signal.

In some embodiments, each ordinate value includes an amplitude metric selected from a group consisting of: a complex magnitude of the analytic component signal, a real part of the analytic component signal, and an imaginary part of the analytic component signal, In some embodiments, each ordinate value includes an amplitude metric consisting of: the complex magnitude of the analytic component signal, the real part of the analytic component signal, and the imaginary part of the analytic component signal.

In some embodiments, each abscissa value is based upon a time metric.

In some embodiments, each fractional-phase representation includes a phase adjustment value such that a linear combination of the plurality of component values substantially reconstructs the quasi-periodic waveform.

In some embodiments, each fractional-phase representation includes an amplitude normalization value such that a linear combination of the plurality of component values substantially reconstructs the quasi-periodic waveform.

In some embodiments, the component signal is an electrocardiogram (ECG) signal from a human.

In some embodiments, the zero crossing is evaluated by finding a change in sign.

In some embodiments, the abscissa for each zero crossing is evaluated by performing an interpolation in a neighborhood of the sign change.

In some embodiments, the interpolation is a curve fit and the zero crossing is evaluated by solving for a root.

In some embodiments, the amplitude metric is obtained from a quarter-phase.

In some embodiments, the invention provides a computer-readable medium having executable instructions stored thereon for causing a suitable programmed central processing unit to perform a method that includes: obtaining a plurality of component signals representative of a quasi-periodic waveform, wherein each component signal includes a plurality of component values that represent a digitally filtered frequency-limited band of the quasi-periodic waveform, and transforming each of the plurality of component values into a fractional-phase representation including values representing an abscissa, an ordinate, or both values representing an abscissa and values representing an ordinate for each of a plurality of fractional phases per local cycle of the component signal, and storing the fractional-phase representation in a storage device. In some embodiments, the computer-readable medium includes further instructions configured for each ordinate value to be based on an amplitude metric. In some embodiments, the computer-readable media allowing each abscissa value to be based on a time metric.

In some embodiments, the computer-readable medium includes further instructions configured for each fractional-phase representation to include a phase adjustment value such that a linear combination of the plurality of component values substantially reconstructs the quasi-periodic waveform.

In some embodiments, the computer-readable medium includes further instructions configured for a fractional-phase representation to include an amplitude normalization value such that a linear combination of the plurality of component values substantially reconstructs the quasi-periodic waveform.

In some embodiments of the invention, the computer-readable medium includes further instructions configured for the component signal to include a first fractional phase, a second fractional phase, a third fractional phase, and a fourth fractional phase, and includes further instructions configured such that: the fractional-phase representation for the first fractional phase includes a value representing an abscissa associated with a zero crossing of the associated component signal, the fractional-phase representation for the second fractional phase includes a value representing an ordinate and a value representing an abscissa both values representing an abscissa and values representing an ordinate associated with a maximum of the associated component signal, the fractional-phase representation for the third fractional phase includes a value representing an abscissa associated with another zero crossing of the associated component signal, and the fractional-phase representation for the fourth fractional phase includes a value representing an ordinate and a value representing an abscissa both associated with a minimum of the associated component signal.

In some embodiments, the computer-readable medium includes further instructions configured for each ordinate value to be based on an amplitude metric.

In some embodiments, the computer-readable medium includes further instructions configured for each abscissa value to be based on a time metric.

In some embodiments, the computer-readable medium includes further instructions configured for each fractional-phase representation to include a phase adjustment value such that a linear combination of the plurality of component values substantially reconstructs the quasi-periodic waveform.

In some embodiments, the computer-readable medium includes further instructions configured for each fractional-phase representation to include an amplitude normalization value such that a linear combination of the plurality of component values substantially reconstructs the quasi-periodic waveform.

In some embodiments, the computer-readable medium includes further instructions configured for component signals that are analytic such that the plurality of component values for each component signal are complex-valued, and wherein the fractional-phase representation for each fractional phase includes a value representing an ordinate, a value representing an abscissa, or both values representing an abscissa and values representing an ordinate associated with an angular range of a complex argument of an associated analytic component signal.

In some embodiments, the computer-readable medium includes further instructions configured for each ordinate value to comprise an amplitude metric selected from a group consisting of: a complex magnitude of the analytic component signal, a real part of the analytic component signal, and an imaginary part of the analytic component signal.

In some embodiments, the computer-readable medium includes further instructions configured for each ordinate value to comprise an amplitude metric based upon: the complex magnitude of the analytic component signal, the real part of the analytic component signal, and the imaginary part of the analytic component signal.

In some embodiments, the computer-readable medium includes further instructions configured for each abscissa value to be based on a time metric.

In some embodiments, the computer-readable medium includes further instructions configured for each fractional-phase representation to include a phase adjustment value such that a linear combination of the plurality of component values substantially reconstructs the quasi-periodic waveform.

In some embodiments, the computer-readable medium includes further instructions configured for each fractional-phase representation to include an amplitude normalization value such that a linear combination of the plurality of component values substantially reconstructs the quasi-periodic waveform.

In some embodiments, the computer-readable medium includes further instructions configured for the number of fractional phases available per local cycle of each component signal to be a predetermined number for that component, and wherein the angular ranges for the fractional phases correspond to subdivisions of the angular range of the complex argument.

In some embodiments, the computer-readable medium includes further instructions configured for each ordinate value to be based upon an amplitude metric selected from a group consisting of: a complex magnitude of the analytic component signal, a real part of the analytic component signal, and an imaginary part of the analytic component signal.

In some embodiments, the computer-readable medium includes further instructions configured for ordinate value to be based upon an amplitude metric including: a complex magnitude of the analytic component signal, a real part of the analytic component signal, and an imaginary part of the analytic component signal.

In some embodiments, the computer-readable medium includes further instructions configured for each abscissa value to be based upon a time metric.

In some embodiments, the computer-readable medium includes further instructions configured for each fractional-phase representation to include a phase adjustment value such that a linear combination of the plurality of component values substantially reconstructs the quasi-periodic waveform.

In some embodiments, the computer-readable medium includes further instructions configured for each fractional-phase representation to include an amplitude normalization value such that a linear combination of the plurality of component values substantially reconstructs the quasi-periodic waveform.

In some embodiments, the computer-readable medium includes further instructions configured for the component signal to include a first fractional phase, a second fractional phase, a third fractional phase, and a fourth fractional phase, and also includes further instructions configured for: the fractional-phase representation for the first fractional phase includes a value representing an ordinate, a value representing an abscissa, or both values representing an abscissa and values representing an ordinate associated with a zero crossing of a real part of the associated analytic component signal, the fractional-phase representation for the second fractional phase includes a value representing an ordinate, a value representing an abscissa, or both values representing an abscissa and values representing an ordinate associated with a zero crossing of an imaginary part of the associated analytic component signal, the fractional-phase representation for the third fractional phase includes a value representing an ordinate, a value representing an abscissa, or both values representing an abscissa and values representing an ordinate associated with another zero crossing of the real part of the associated analytic component signal, and the fractional-phase representation for the fourth fractional phase includes a value representing an ordinate, a value representing an abscissa, or both values representing an abscissa and values representing an ordinate associated with another zero crossing of the imaginary part of the associated analytic component signal.

In some embodiments, the computer-readable medium includes further instructions configured for each ordinate value to include an amplitude metric selected from a group consisting of: a complex magnitude of the analytic component signal, a real part of the analytic component signal, and an imaginary part of the analytic component signal.

In some embodiments, the computer-readable medium includes further instructions configured for each ordinate value to include an amplitude metric consisting of: the complex magnitude of the analytic component signal, the real part of the analytic component signal, and the imaginary part of the analytic component signal, In some embodiments, the computer-readable medium includes further instructions configured for each abscissa value to be based upon a time metric.

In some embodiments, the computer-readable medium includes further instructions configured for each fractional-phase representation to include a phase adjustment value such that a linear combination of the plurality of component values substantially reconstructs the quasi-periodic waveform.

In some embodiments, the computer-readable medium includes further instructions configured for each fractional-phase representation to include an amplitude normalization value such that a linear combination of the plurality of component values substantially reconstructs the quasi-periodic waveform.

In some embodiments, the computer-readable medium includes further instructions configured for the quasi-periodic waveform to be an electrocardiogram (ECG) signal from a human.

In some embodiments, the computer-readable media is configured for the zero crossing to be evaluated by finding a change in sign.

In some embodiments, the computer-readable medium includes further instructions configured for the zero crossing to be evaluated by finding a change in sign.

In some embodiments, the computer-readable medium includes further instructions configured for the zero crossing to be evaluated by performing interpolation in the neighborhood of the sign change.

In some embodiments, the computer-readable medium includes further instructions configured for the interpolation to be a curve fit and the zero crossing is evaluated by solving for a root.

In some embodiments, the computer-readable medium includes further instructions configured for the amplitude metric to be obtained from a quarter-phase.

In some embodiments, the invention provides a computer-readable medium having executable instructions stored thereon for causing a suitable programmed information processor to perform a method that includes: obtaining a plurality of fractional-phase representations of a signal, wherein each fractional-phase representation includes values representing an abscissa, an ordinate, or both values representing an abscissa and values representing an ordinate for each of a plurality of fractional phases of a component of a plurality of components that each represent a digitally filtered frequency-limited band of a quasi-periodic waveform, and assigning to each fractional-phase representation a phase label associated with an active fractional phase of the fractional-phase representation, generating a plurality of data structures, each data structure arising from each component associated with a different abscissa value and including a phase label, and storing the plurality of data structures in a storage device.

In some embodiments, the computer-readable medium includes further instructions configured for each ordinate value is based upon an amplitude metric.

In some embodiments, the computer-readable medium includes further instructions configured for the associated component to be an analytic signal and each ordinate value is derived from an amplitude metric selected from a group consisting of: a complex magnitude of the analytic component signal, a real part of the analytic component signal, and an imaginary part of the analytic component signal.

In some embodiments, the computer-readable medium includes further instructions configured for the associated component to be an analytic signal and each ordinate value is derived from an amplitude metric based upon: a complex magnitude of the analytic component signal, a real part of the analytic component signal, and an imaginary part of the analytic component signal.

In some embodiments, the computer-readable media allows the ordinate to be based upon a statistical measure.

In some embodiments, the computer-readable medium includes further instructions configured for each of the abscissa values to be based upon a time metric.

Some embodiments of the invention include a computer-readable media having stored thereon a first data structure that includes: a descriptor that includes an abscissa value from an associated fractional-phase representation, a optional descriptor that includes an ordinate value from the associated fractional-phase representation, an optional descriptor that includes an abscissa interval value representing an interval of the abscissa over which an associated fractional phase is active, an optional descriptor that includes a label identifying a particular data structure from the plurality of data structures, an optional descriptor that includes a label identifying an associated component from the plurality of components, an optional descriptor that includes a label identifying the quasi-periodic waveform, an optional descriptor that includes a value representing a local period of the associated component, an optional descriptor that includes a value representing an interval from a reference abscissa value to an associated abscissa value, an optional descriptor that includes a value representing a relative measure between the ordinate value associated with the fractional phase, and an ordinate value associated with the component, the quasi-periodic waveform, or both the component and the quasi-periodic waveform, and an optional descriptor that includes a label indicating that the component is active for the active fractional phase associated with the particular data structure, based upon comparing the ordinate value to a predetermined threshold.

In some embodiments of the computer-readable medium having the data structure stored thereon, each ordinate value is based upon an amplitude metric.

In some embodiments of the computer-readable medium having the data structure stored thereon, the associated component is an analytic signal and each ordinate value is derived from an amplitude metric selected from a group consisting of: a complex magnitude of the analytic component signal, a real part of the analytic component signal, and an imaginary part of the analytic component signal.

In some embodiments of the computer-readable medium having the data structure stored thereon, the associated component is an analytic signal and each ordinate value is derived from an amplitude metric based upon: a complex magnitude of the analytic component signal, a real part of the analytic component signal, and an imaginary part of the analytic component signal.

In some embodiments of the computer-readable medium having the data structure stored thereon, the abscissa values are based upon a time metric.

Some embodiments of the computer-readable medium having the data structure stored thereon include an atomic period value, wherein the atomic period value is the abscissa interval value multiplied by a number of fractional phases available in the fractional-phase representation.

In some embodiments of the computer-readable medium having the data structure stored thereon, the data structure further includes links to other data structures, including: a descriptor that includes a link to another particular data structure associated with the component, wherein the associated abscissa value of the other data structure is less than the abscissa value associated in the particular data structure, an optional descriptor that includes a link to another particular data structure associated with the component, wherein the abscissa value of the other data structure is greater than the abscissa value in the particular data structure, an optional descriptor that includes a link to another particular data structure associated with the component, wherein the abscissa value of the other data structure is less than the abscissa value in the particular data structure, and wherein the phase label of the other data structure is of the same value as the phase label of the particular data structure, and an optional descriptor that includes a link to another particular data structure associated with the component, wherein the abscissa value of the other data structure is greater than the abscissa value in the particular data structure, and wherein the phase label of the other data structure is of the same value as the phase label of the particular data structure.

In some embodiments of the computer-readable medium having the data structure stored thereon, the data structure further includes: a descriptor that includes a difference of abscissa values between the abscissa value included in the particular data structure and the abscissa value included in a first linked data structure relative to this particular data structure, an optional descriptor that includes a difference of abscissa values between the abscissa value included in the particular data structure and the abscissa value included in a second linked data structure relative to this particular data structure, an optional descriptor that includes an indication of deviation from an expected sequence of phase labels, and an optional descriptor that includes a moving average of abscissa values for a group of data structures surrounding the particular data structure.

In some embodiments of the computer-readable medium having the data structure stored thereon, the data structure is organized within a plurality of other data structures into an array based upon a common associated component.

In some embodiments of the computer-readable medium having the data structure stored thereon, the data structure further includes a label to the data structure, wherein a label describes a transition of the component to and from an active condition.

In some embodiments of the computer-readable medium having the data structure stored thereon, the data structure further includes a first phase label associated with a first fractional phase of a given component, a second phase label associated with a second fractional phase of the given component, a third phase label associated with a third fractional phase of the given component, and a fourth phase label associated with a fourth fractional phase of the given component.

Some embodiments of the invention include a computer-readable medium having the data structure stored thereon, wherein the data structure further includes: a descriptor including an abscissa interval value representing the interval of the abscissa over which the associated fractional phase is active to the first data structure, and a plurality of optional descriptors including at least three selected from the set comprising: an optional descriptor that identifies the first data structure from the plurality of data structures, an optional descriptor identifying the associated component from the plurality of components, an optional descriptor assigning a label identifying the quasi-periodic waveform, an optional descriptor assigning a value to representing the local period of the associated component, an optional descriptor assigning a referenced abscissa value representing the interval from a reference abscissa value to the associated abscissa value, an optional descriptor assigning a link to another data structure associated with the component, wherein the included abscissa value of the other data structure is less than the abscissa value, an optional descriptor assigning a link to another data structure associated with the component, wherein the included abscissa value of the other data structure is greater than the abscissa value included in the first data structure, an optional descriptor assigning to the first data structure a link to a second data structure associated with the component, wherein the second data structure is an upper neighbor, an optional descriptor assigning to the first data structure a link to a third data structure associated with the component, wherein the third data structure is a lower neighbor, an optional descriptor assigning to the first data structure a relative T value, an optional descriptor assigning to the first data structure a left harmonic value, an optional descriptor assigning to the first data structure a right harmonic value, an optional descriptor assigning to the first data structure an amplitude measurement, an optional descriptor assigning to the first data structure a phase label, an optional descriptor assigning to the first data structure a left object, an optional descriptor assigning to the first data structure a right object, and an optional descriptor assigning to the first data structure a relative amplitude value.

Some embodiments of the computer-readable medium further include a plurality of data structures organized as a list based upon a common associated component.

Some embodiments of the computer-readable medium further include a plurality of data structures organized as a tree based upon a common associated component.

Some embodiments of the computer-readable medium further include a plurality of data structures organized as a hash table based upon a common associated component.

Some embodiments of the computer-readable medium further include a plurality of data structures organized as a heap based upon a common associated component.

Some embodiments of the computer-readable medium further include a plurality of data structures organized as an array based upon a common associated component.

Some embodiments of the invention provide a method that includes: obtaining one or more data structures, organizing the one or more data structures into an arranged data structure, wherein the one or more arranged data structures are arranged according to their associated component, and the fractional phases associated with the one or more data structures within each arranged data structure are co-active over a range of abscissa values for an associated quasi-periodic waveform, generating a plurality of states, each state including a group of one or more arranged data structures, and storing the states in a storage device.

In some embodiments, the plurality of states include a state with a reference abscissa value associated with the abscissa values of the arranged data structure, and assigned to the state, and the plurality of states are arranged into a state sequence, according to the associated abscissa values.

In some embodiments, the reference abscissa value is the greatest of the abscissa values of the arranged data structure assigned to the corresponding state.

In some embodiments of the method, a new state is formed upon a change of an active fractional phase of one or more of the arranged data structures in the state, and forming a sequence of states.

In some embodiments, the method further includes: analyzing a state trajectory in state space, and identifying a set of features within a quasi-periodic waveform, a component signal, or both the quasi-periodic waveform and the component signals based upon the state space.

In some embodiments of the method, the quasi-periodic waveform signal is an electrocardiogram (ECG) signal from a mammal, with features including: a P wave, a Q wave, an R wave, an S wave, a T wave, a U wave, and any ECG segment delineated by any pair of these waves.

In some embodiments of the method, the quasi-periodic waveform signal is an electrocardiogram (ECG) signal from a mammal, with features selected from a group consisting of: a P wave, a Q wave, an R wave, an S wave, a T wave, a U wave, and any ECG segment delineated by any pair of these waves.

In some embodiments of the method, the quasi-periodic waveform signal is a heart-sound signal from a mammal, and the features include: an S1, an S2, and an S3 sound.

In some embodiments of the method, the quasi-periodic waveform signal is a heart-sound signal from a mammal and includes features selected from a group consisting of: an S1, an S2, and an S3 sound.

In some embodiments, the quasi-periodic waveform signal is a blood-pressure signal from a mammal, and the features include a dicrotic notch.

In some embodiments, the quasi-periodic waveform signal is a blood-flow signal from a mammal. In some embodiments, the quasi-periodic waveform signal is an electroencephalogram (EEG) signal from a mammal. In some embodiments, the quasi-periodic waveform signal is an electromyogram (EMG) signal from a mammal. In some embodiments, the quasi-periodic waveform signal is an electrooculogram (EOG) signal from a mammal. In some embodiments, the quasi-periodic waveform signal is a respiratory signal from a mammal, wherein the respiratory signal an optional descriptor includes: pressure, flow, and volume information.

Some embodiments of the method further include: analyzing a state trajectory in state space, and identifying a condition subset from a predetermined set of conditions associated with a quasi-periodic waveform, a component signal, or both the quasi-periodic waveform and the component signals based upon the state space analysis.

In some embodiments, the quasi-periodic waveform signal is an electrocardiogram (ECG) signal from a mammal. In some embodiments, the quasi-periodic waveform signal is a heart-sound signal from a mammal. In some embodiments, the quasi-periodic waveform signal is a blood-pressure signal from a mammal. In some embodiments, the quasi-periodic waveform signal is a blood-flow signal from a mammal. In some embodiments, the quasi-periodic waveform signal is an EEG, EMG, or EOG signal from a mammal. In some embodiments, the quasi-periodic waveform signal is a respiratory signal from a mammal, wherein the respiratory signal an optional descriptor includes pressure, flow, and volume information. In some embodiments, the quasi-periodic waveform signal is derived from a mammal and a condition set include an optional descriptor the condition normal, and an optional descriptor the condition abnormal.

In some embodiments of the method, the condition set includes cardiac conditions, the normal condition is normal sinus rhythm, and the abnormal condition is a set of rhythm abnormalities including: an optional descriptor bradycardia and tachycardia abnormality, and an optional descriptor conduction abnormality, wherein bradycardia is an optional descriptor set including sick sinus syndrome, and tachycardia is an optional descriptor set including atrial flutter, atrial fibrillation, ventricular tachycardia, and ventricular fibrillation, and conduction abnormality is an optional descriptor set to include bundle branch block, AV and node block.

In some embodiments, the method wherein: the condition set includes cardiac conditions, the normal condition is normal sinus rhythm, and the abnormal condition is a set of structural abnormalities including: optional ischemia, optional myocardial infarction, optional left ventricular hypertrophy, optional right ventricular hypertrophy, optional bi-ventricular hypertrophy, optional long QT syndrome, and optional tall T syndrome.

In some embodiments, the set conditions are normal blood pressure and abnormal blood pressure. In some embodiments, the method wherein the set conditions include hypotension and hypertension.

Some embodiments of the invention provide a method that includes: obtaining a state sequence resulting from each of one or more quasi-periodic waveforms comprising a training set, wherein each quasi-periodic waveform corresponds to a predetermined set of feature types and assigned by feature type in a known manner to a set of states forming a state subsequence of the associated state sequence, constructing a sequence detector for each state subsequence resulting from a training set, such that detection of the state subsequence is an indication of the assigned feature type, and identifying the feature type associated with each feature of an arbitrary test quasi-periodic waveform, based upon a pattern-matching operation.

In some embodiments, the pattern-matching operation includes: establishing a degree of match measure between the sequences associated with each detector and the state sequence resulting from the test waveform, and forming a fuzzy inference upon these measures through a fuzzy logic mapping.

In some embodiments, the pattern-matching operation includes: establishing a degree of match measure between the state sequence associated with each detector and the state sequence resulting from the test waveform, and applying a neural network mapping to these measures, wherein the neural network is trained on the training set.

In some embodiments, the method further includes: obtaining the state sequence resulting from each of one or more quasi-periodic waveforms comprising a training set, each waveform assigned in a known manner to a subset of a set of one or more predetermined conditions, constructing a sequence detector for each state sequence resulting from the training set, such that detection of the state sequence is an indication of the assigned condition subset, and identifying the condition subset associated with an arbitrary test quasi-periodic waveform, based upon a pattern-matching operation.

In some embodiments, the pattern-matching operation includes: establishing a degree of match measure between the sequences associated with each detector and the state sequence resulting from the test waveform, and forming a fuzzy inference upon these measures through a fuzzy logic mapping.

In some embodiments, the pattern-matching operation includes: establishing a degree of match measure between the sequence associated with each detector and the state sequence resulting from the test waveform, and applying a neural network mapping to these measures, wherein the neural network is trained on the training set.

In some embodiments, the method further comprising: obtaining a state sequence resulting from each of one or more quasi-periodic waveforms comprising a training set, each feature of a set of features in each waveform corresponding to a predetermined set of feature types and assigned by feature type in a known manner to a set of states forming a subsequence of the associated state sequence, constructing a model according to a span of a state vector or a subspace of that span in state space, training the model based upon the state subsequences resulting from a training data set, including associated feature sets as labels for supervised learning, and identifying a feature type associated with each feature of an arbitrary test quasi-periodic waveform, based upon statistics in the trained model in relation to the state subsequences resulting from test waveform features.

In some embodiments, the model has multiple modalities. In some embodiments, the model includes a plurality of submodels. In some embodiments, the submodel is a Hidden Markov Model, a Neural Network, or a Fuzzy Logic Mapping. In some embodiments, the model is a Hidden Markov Model, a Neural Network, or a Fuzzy Logic Mapping.

Some embodiments further include obtaining a state sequence resulting from each of one or more quasi-periodic waveforms comprising a training set, each waveform assigned in a known manner to a subset of a set of one or more predetermined conditions, constructing a model according to a span of a state vector or a subspace of that span in state space, training the model based upon the state sequences resulting from a training data set, including associated condition sets as labels for supervised learning, and identifying the condition subset associated with an arbitrary test quasi-periodic waveform, based upon statistics in the trained model in relation to the state sequence resulting from a test waveform.

In some embodiments, the model has multiple modalities. In some embodiments, the model includes a plurality of submodels. In some embodiments, the submodel is a Hidden Markov Model, a Neural-Network, or a Fuzzy Logic Mapping. In some embodiments, the model is a Hidden Markov Model, a Neural Network, or a Fuzzy Logic Mapping.

In some embodiments, the invention includes obtaining a state sequence resulting from each of one or more quasi-periodic waveforms comprising a training set, waveforms in aggregation containing an unknown set of features generally falling into groups, these features each having an associated set of states forming a subsequence of the associated state sequence, constructing a model according to a span of a state vector or a subspace of that span in state space, training the model based upon the state subsequences resulting from the training data set, allowing for self-organization of the clusters in state-space, assigning labels to the emergent clusters and associating them with corresponding feature types on the quasi-periodic waveform, and identifying the feature type associated with each feature of an arbitrary test quasi-periodic waveform, based upon statistics in the trained model in relation to the state subsequences resulting from test waveform features.

In some embodiments, the model has multiple modalities. In some embodiments, the model includes a plurality of submodels. In some embodiments, the submodel is a Hidden Markov Model, a Neural Network, or a Fuzzy Logic Mapping. In some embodiments, the model is a Hidden Markov Model, a Neural Network, or a Fuzzy Logic Mapping.

In some embodiments, the invention includes obtaining the state sequence resulting from each of one or more quasi-periodic waveforms comprising a training set, the waveforms in aggregation pertaining to one or more unknown conditions of a set of conditions of unknown size, these waveforms each having an associated state sequence, constructing a model according to the span of the state vector or a subspace of that span in state space, training the model based upon the state sequences resulting from the training data set, allowing for self-organization of the clusters in state-space, and assigning labels to the emergent clusters and associating them with condition types, and identifying the set of condition types associated with an arbitrary test quasi-periodic waveform, based upon the statistics in the trained model in relation to the state sequence resulting from the test waveform. In some embodiments, the model has multiple modalities. In some embodiments, the model includes a plurality of submodels. In some embodiments, the submodel is a Hidden Markov Model, a Neural Network, or a Fuzzy Logic Mapping. In some embodiments, the model is a Hidden Markov Model, a Neural Network, or a Fuzzy Logic Mapping. In some embodiments, the states are pruned from the state trajectory based upon the relative time of habitation within the states. In some embodiments, the states are pruned from the state trajectory based upon the relative time of habitation within the states.

Some embodiments of the invention provide a computer-readable medium having executable instructions stored thereon for causing a suitable programmed central processing unit to perform a method that includes: obtaining one or more data structures, organizing the one or more data structures into an arranged data structure, wherein the one or more arranged data structures are arranged according to their associated component, and the fractional phases associated with the one or more data structures within each arranged data structure are co-active over a range of abscissa values for an associated quasi-periodic waveform, generating a plurality of states, each state including a group of one or more arranged data structures, and storing the states in a storage device.

In some embodiments, the computer-readable medium includes further instructions configured for the plurality of states to contain a state with a reference abscissa value associated with the abscissa values of the arranged data structure, and assigned to the state, and the plurality of states are arranged into a state sequence, according to the associated abscissa values.

In some embodiments, the computer-readable medium includes further instructions configured for the reference abscissa value to be the greatest of the abscissa values of the arranged data structure assigned to the corresponding state.

In some embodiments, the computer-readable medium includes further instructions configured for a new state to be formed upon a change of an active fractional phase of one or more of the arranged data structures in the state, and forming a sequence of states.

In some embodiments, the computer-readable medium includes further instructions configured for analyzing a state trajectory in state space, and identifying a set of features within a quasi-periodic waveform, a component signals, or both the quasi-periodic waveform and the component signals based upon the state space.

In some embodiments, the computer-readable medium includes further instructions configured for the quasi-periodic waveform signal to be an electrocardiogram (ECG) signal from a mammal, with features including: a P wave, a Q wave, an R wave, an S wave, a T wave, a U wave, and any ECG segment delineated by any pair of these waves.

In some embodiments, the computer-readable medium includes further instructions configured for the quasi-periodic waveform signal to be an electrocardiogram (ECG) signal from a mammal, with features selected from a group consisting of: a P wave, a Q wave, an R wave, an S wave, a T wave, a U wave, and any ECG segment delineated by any pair of these waves.

In some embodiments, the computer-readable medium includes further instructions configured for the quasi-periodic waveform signal to be a heart sound signal from a mammal, and the features include: an S1, an S2, and an S3 sound.

In some embodiments, the computer-readable medium includes further instructions configured for the quasi-periodic waveform signal to be a heart sound signal from a mammal and includes features selected from a group consisting of: an S1, an S2, and an S3 sound.

In some embodiments, the computer-readable medium includes further instructions configured for the quasi-periodic waveform signal to be a blood pressure signal from a mammal, and the features include a dicrotic notch.

In some embodiments, the computer-readable medium includes further instructions configured for the quasi-periodic waveform signal to be a blood flow signal from a mammal.

In some embodiments, the computer-readable medium includes further instructions configured for the quasi-periodic waveform signal to be an EEG, an EMG, or a EOG signal from a mammal.

In some embodiments, the computer-readable medium includes further instructions configured for the quasi-periodic waveform signal to be a respiratory signal from a mammal, further comprising allowing the respiratory signal an optional descriptor includes: pressure, flow, and volume information.

In some embodiments, the computer-readable medium includes further instructions configured for analyzing a state trajectory in state space, and identifying a condition subset from a predetermined set of conditions associated with a quasi-periodic waveform, a component signal, or both the quasi-periodic waveform and the component signals based upon the state space analysis.

In some embodiments, the computer-readable medium includes further instructions configured for the quasi-periodic waveform signal to be an electrocardiogram (ECG) signal from a mammal.

In some embodiments, the computer-readable medium includes further instructions configured for the quasi-periodic waveform signal to be a heart sound signal from a mammal.

In some embodiments, the computer-readable medium includes further instructions configured for the quasi-periodic waveform signal to be a blood pressure signal from a mammal.

In some embodiments, the computer-readable medium includes further instructions configured for the quasi-periodic waveform signal to be a blood flow signal from a mammal.

In some embodiments, the computer-readable medium includes further instructions configured for the quasi-periodic waveform signal to be an EEG, EMG or an EOG signal from a mammal.

In some embodiments, the computer-readable medium includes further instructions configured for the quasi-periodic waveform signal to be a respiratory signal from a mammal, further comprising allowing the respiratory signal an optional descriptor includes: pressure, flow, and volume information.

In some embodiments, the computer-readable medium includes further instructions configured for the quasi-periodic waveform signal to be derived from a mammal and a condition set including: an optional descriptor the condition normal, and an optional descriptor the condition abnormal.

In some embodiments, the computer-readable medium includes further instructions configured such that the condition set includes cardiac conditions, the normal condition is normal sinus rhythm, and the abnormal condition is a set of rhythm abnormalities including an optional descriptor bradycardia and tachycardia abnormality, and an optional descriptor conduction abnormality, further comprising allowing bradycardia is an optional descriptor set including sick sinus syndrome, and tachycardia is an optional descriptor set including atrial flutter, atrial fibrillation, ventricular tachycardia, and ventricular fibrillation, and conduction abnormality is an optional descriptor set to include bundle branch block, AV and node block.

In some embodiments, the computer-readable medium includes further instructions configured such that the condition set includes cardiac conditions, the normal condition is normal sinus rhythm, and the abnormal condition is a set of structural abnormalities including: optional ischemia, optional myocardial infarction, optional left ventricular hypertrophy, optional right ventricular hypertrophy, optional bi-ventricular hypertrophy, optional long QT syndrome, and optional tall T syndrome.

In some embodiments, the computer-readable medium includes further instructions configured for the set conditions to be normal blood pressure and abnormal blood pressure.

In some embodiments, the computer-readable medium includes further instructions configured for the set conditions to include hypotension and hypertension.

In some embodiments, the computer-readable medium includes further instructions configured for obtaining a state sequence resulting from each of one or more quasi-periodic waveforms comprising a training set, further comprising allowing each quasi-periodic waveform corresponds to a predetermined set of feature types and assigned by feature type in a known manner to a set of states forming a state subsequence of the associated state sequence, constructing a sequence detector for each state subsequence resulting from a training set, such that detection of the state subsequence is an indication of the assigned feature type, and identifying the feature type associated with each feature of an arbitrary test quasi-periodic waveform, based upon a pattern-matching operation.

In some embodiments, the computer-readable medium includes further instructions configured for the pattern-matching operation includes: establishing a degree of match measure between the sequences associated with each detector and the state sequence resulting from the test waveform, and forming a fuzzy inference upon these measures through a fuzzy logic mapping.

In some embodiments, the computer-readable medium includes further instructions configured for the pattern-matching operation includes: establishing a degree of match measure between the state sequences associated with each detector and the state sequence resulting from the test waveform, and applying a neural network mapping to these measures, further comprising allowing the neural network is trained on the training set.

In some embodiments, the computer-readable medium includes further instructions configured for obtaining the state sequence resulting from each of one or more quasi-periodic waveforms comprising a training set, each waveform assigned in a known manner to a subset of a set of one or more predetermined conditions, constructing a sequence detector for each state sequence resulting from the training set, such that detection of the state sequence is an indication of the assigned condition subset, and identifying the condition subset associated with an arbitrary test quasi-periodic waveform, based upon a pattern-matching operation.

In some embodiments, the computer-readable medium includes further instructions configured for the pattern-matching operation includes: establishing a degree of match measure between the sequences associated with each detector and the state sequence resulting from the test waveform, and forming a fuzzy inference upon these measures through a fuzzy logic mapping.

In some embodiments, the computer-readable medium includes further instructions configured for the pattern-matching operation includes: establishing a degree of match measure between the sequences associated with each detector and the state sequence resulting from the test waveform, and applying a neural network mapping to these measures, further comprising allowing the neural network is trained on the training set.

In some embodiments, the computer-readable medium includes further instructions configured for obtaining a state sequence resulting from each of one or more quasi-periodic waveforms comprising a training set, each feature of a set of features in each waveform corresponding to a predetermined set of feature types and assigned by feature type in a known manner to a set of states forming a subsequence of the associated state sequence, constructing a model according to a span of a state vector or a subspace of that span in state space, training the model based upon the state subsequences resulting from a training data set, including associated feature sets as labels for supervised learning, and identifying a feature type associated with each feature of an arbitrary test quasi-periodic waveform, based upon statistics in the trained model in relation to the state subsequences resulting from test waveform features.

In some embodiments, the computer-readable medium includes further instructions configured for the model to have multiple modalities.

In some embodiments, the computer-readable medium includes further instructions configured for producing the model to include a plurality of submodels.

In some embodiments, the computer-readable medium includes further instructions configured for producing the submodel as a Hidden Markov Model, Neural Network, or a Fuzzy Logic Mapping.

In some embodiments, the computer-readable medium includes further instructions configured for the model to be a Hidden Markov Model, Neural Network, or a Fuzzy Logic Mapping.

In some embodiments, the computer-readable medium includes further instructions configured for obtaining a state sequence resulting from each of one or more quasi-periodic waveforms comprising a training set, each waveform assigned in a known manner to a subset of a set of one or more predetermined conditions, constructing a model according to a span of a state vector or a subspace of that span in state space, training the model based upon the state sequences resulting from a training data set, including associated condition sets as labels for supervised learning, and identifying the condition subset associated with an arbitrary test quasi-periodic waveform, based upon statistics in the trained model in relation to the state sequence resulting from a test waveform.

In some embodiments, the computer-readable medium includes further instructions configured for the model to have multiple modalities.

In some embodiments, the computer-readable medium includes further instructions configured for the model to have a plurality of submodels.

In some embodiments, the computer-readable medium includes further instructions configured for the submodel to be a Hidden Markov Model, Neural Network, or a Fuzzy Logic Mapping.

In some embodiments, the computer-readable medium includes further instructions configured for the model to be a Hidden Markov Model, Neural Network, or Fuzzy Logic Mapping.

Some embodiments of the invention provide a computer-readable medium that includes instructions configured to perform a method that includes: obtaining a state sequence resulting from each of one or more quasi-periodic waveforms comprising a training set, waveforms in aggregation containing an unknown set of features generally falling into groups, these features each having an associated set of states forming a subsequence of the associated state sequence, constructing a model according to a span of a state vector or a subspace of that span in state space, training the model based upon the state subsequences resulting from the training data set, allowing for self-organization of the clusters in state-space, assigning labels to the emergent clusters and associating them with corresponding feature types on the quasi-periodic waveform, and identifying the feature type associated with each feature of an arbitrary test quasi-periodic waveform, based upon statistics in the trained model in relation to the state subsequences resulting from test waveform features.

In some embodiments, the computer-readable medium includes further instructions configured for the model to have multiple modalities.

In some embodiments, the computer-readable medium includes further instructions configured for the model to include a plurality of submodels.

In some embodiments, the computer-readable medium includes further instructions configured for the submodel to be a Hidden Markov Model, Neural Network, or Fuzzy Logic Mapping.

In some embodiments, the computer-readable medium includes further instructions configured for the model to be a Hidden Markov Model, Neural Network, or a Fuzzy Logic Mapping.

In some embodiments, the computer-readable medium includes further instructions configured for obtaining the state sequence resulting from each of one or more quasi-periodic waveforms comprising a training set, the waveforms in aggregation pertaining to one or more unknown conditions of a set of conditions of unknown size, these waveforms each having an associated state sequence, constructing a model according to the span of the state vector or a subspace of that span in state space, training the model based upon the state sequences resulting from the training data set, allowing for self-organization of the clusters in state-space, and assigning labels to the emergent clusters and associating them with condition types, and identifying the set of condition types associated with an arbitrary test quasi-periodic waveform, based upon the statistics in the trained model in relation to the state sequence resulting from the test waveform.

In some embodiments, the computer-readable medium includes further instructions configured for the model to have multiple modalities.

In some embodiments, the computer-readable medium includes further instructions configured for the model to include a plurality of submodels.

In some embodiments, the computer-readable medium includes further instructions configured for the submodel to be a Hidden Markov Model, a Neural Network, or a Fuzzy Logic Mapping.

In some embodiments, the computer-readable medium includes further instructions configured for the model to be a Hidden Markov Model, Neural Network, or a Fuzzy Logic Mapping.

In some embodiments, the computer-readable medium includes further instructions configured for allowing the states to be pruned from the state trajectory based upon the relative time of habitation within the states.

In some embodiments, the computer-readable medium includes further instructions configured for allowing the states to be pruned from the state trajectory based upon the relative time of habitation within the states.

Some embodiments of the invention provide a method that includes: obtaining a plurality of data structures, assigning the data structure attributes to a reconstruction formula to substantially reconstruct the associated component signal over the associated abscissa interval where the associated fractional phase is active, and generating a plurality of one or more reconstructed component signals.

In some embodiments, the method allows the plurality of reconstructed component signals to be linearly combined to substantially reconstruct the quasi-periodic waveform.

In some embodiments, the method allows the subset of the one or more reconstructed component signals to be linearly combined to substantially reconstruct a desired portion of the quasi-periodic waveform.

In some embodiments, the method further includes: obtaining a plurality of data structures, performing data compression on the data structures, and storing the compressed data structures in a storage device.

In some embodiments, the method provides for compression to be performed through selective removal of data structures containing redundant/unremarkable information.

In some embodiments, the method provides for compression to be performed through selective removal of redundant/unremarkable information in the data structures.

In some embodiments, the method provides for compression to be performed through data compression operations performed upon the attribute information in the data structures.

Some embodiments of the invention provide a computer-readable medium having executable instructions stored thereon for causing a suitable programmed processing unit to perform a method that includes: obtaining a plurality of data structures, assigning the data structure attributes to a reconstruction formula to substantially reconstruct the associated component signal over the associated abscissa interval where the associated fractional phase is active, and generating a plurality of one or more reconstructed component signals.

In some embodiments, the computer-readable medium includes further instructions configured for the plurality of reconstructed component signals to be linearly combined to substantially reconstruct the quasi-periodic waveform.

In some embodiments, the computer-readable medium includes further instructions configured for a subset of one or more reconstructed component signals to be linearly combined to substantially reconstruct a desired portion of the quasi-periodic waveform.

Some embodiments of the invention provide a computer-readable medium that includes instructions for causing a suitable programmed central processing unit to perform a method that includes: obtaining a plurality of data structures, performing data compression on the data structures, and storing the compressed data structures in a storage device.

In some embodiments, the computer-readable media is described wherein the compression is performed through selective removal of data structures containing redundant/unremarkable information.

In some embodiments, the computer-readable medium includes further instructions configured for the compression to be performed through selective removal of redundant/unremarkable information in the data structures.

In some embodiments, the computer-readable medium includes further instructions configured for the compression to be performed through data compression operations performed upon the attribute information in the data structures.

As used herein, a fractional phase is one of a plurality of fractional phases in a fractional phase representation (i.e., an interval within one or more cycles of a component signal representative of a digitally filtered frequency-limited band obtained from a quasi-periodic waveform).

As used herein, a quarter-phase is one of four fractional phases in a fractional phase representation (i.e., one of four intervals within one cycle of a component signal representative of a digitally filtered frequency-limited band obtained from a quasi-periodic waveform).

As used herein, a quasi-periodic waveform is a signal that may be considered as the linear combination of a series of locally periodic component signals, each having different periods and/or shapes, with locality exhibited on the order of a cycle to a few cycles. Examples of quasi-periodic waveforms that can be processed and analyzed by the present invention include but are not limited to:

general biological signals from humans or animals such as ECG waveforms, intracardiac electrogram (EGM) waveforms, EEG waveforms, EMG waveforms, EOG waveforms, blood pressure waveforms, plethysmography waveforms, heart sounds, ultrasound signals, MRI signals, bio-impedance waveforms, electro-dermal testing and polygraph signals;

natural phenomena such as solar sunspot cycles, climate patterns, patterns of El Niñ, drought cycles, seismic activity (i.e., earthquakes in certain areas occur approximately every N years, and major earthquakes can be preceded by relatively minor seismic activity that exhibit quasi-periodic characteristics), ocean currents and tides, and occurrence of tsunamis;

manufacturing process signals for feedback and control;

demographics and societal patterns such as population cycles, product market preferences, crowd noise, traffic patterns, traffic noise, and industrial noise;

vehicular signals pertaining to feedback, control, and detection and diagnosis of issues associated with operation and/or service of a vehicle, such as engine and transmission noise, temperature, information from any number of different types of sensors such as oxygen sensors, temperature sensors, pressure sensors, and flow sensors;

aircraft performance-related signals, such as from laminar-flow sensors, pressure sensors, windshear sensors and downdraft sensors;

financial time series, representing for example prices of stocks, equities, securities, commodities, bonds, mutual funds, and futures, and economic cycles including micro and macro-economic phenomena;

content-carrying signals, such as music, speech or video signals (including analysis and compression of such signals);

telemetry signals for applications such as radar (including, for example, Synthetic Aperture Radar (SAR), Terrain Following Radar (TFR), and Forward-Looking Infrared (FLIR) radar) and sonar;

communications signals such as transmitted over an optical fiber, cable or remote radio link (including spread-spectrum transmissions), such as weak signals from satellites and spacecraft or animal-tracking devices, cordless and cellular telephones, and wireless computer networks such as those using the IEEE802.11g standard;

analysis of data storage medium signals such as from a magnetic disk head or a laser optical receiver for optical storage media; and other signals exhibiting quasi-periodic behavior, including seismic signals obtained for oil exploration.

Other embodiments involving various permutations and distributions of processes or blocks within the Device and Host are specifically contemplated to fall within the scope of this current invention. Some embodiments include combinations or subcombinations of a plurality of items listed individually or within one or more groups of other items.

Some embodiments of the invention provide a method that includes: obtaining a component signal representative of a digitally filtered frequency-limited band from a quasi-periodic waveform, wherein the component signal includes a plurality of component values, reducing the plurality of component values into a fractional-phase representation of N fractional phases where N is greater than one, and wherein each fractional phase is associated with a phase label and includes one or more values representing an abscissa, an ordinate, or both an abscissa and an associated ordinate for each of one or more local cycles of the component signal, and storing the fractional-phase representation in a data structure on a storage device.

In some embodiments of the method, the fractional-phase representation for one local cycle of the component signal includes a first fractional phase, a second fractional phase, a third fractional phase, and a fourth fractional phase, and wherein the reducing of the plurality of component values into the fractional-phase representation further includes: obtaining, for the first fractional phase, a value representing an abscissa of a zero crossing of the component signal, obtaining, for the second fractional phase, a value representing an ordinate and a value representing an abscissa of a maximum of the component signal, obtaining, for the third fractional phase, a value representing an abscissa of another zero crossing of the component signal, and obtaining, for the fourth fractional phase, a value representing an ordinate and a value representing an abscissa of a minimum of the component signal.

In some embodiments, each ordinate value is obtained based on an amplitude metric and each abscissa value is based on a time metric, and wherein the component signal is an electrocardiogram (ECG) signal from a human.

In some embodiments, each zero crossing is determined by finding a change in sign and interpolating in the neighborhood of the sign change using a curve fit.

In some embodiments, the maximum and the minimum of the component signal are each obtained by finding a change in sign in an estimate of the local derivative and interpolating in the neighborhood of the sign change using a curve fit.

In some embodiments, the method further includes: calculating a fractional phase adjustment value for the fractional-phase representation such that a linear combination of values derived from the fractional-phase representation with values derived from one or more other fractional-phase representations obtained from other digitally filtered frequency-limited bands substantially reconstructs the quasi-periodic waveform.

In some embodiments, the component signal is analytic such that the plurality of component values for the component signal are complex numbers, and wherein the fractional-phase representation for each fractional phase is associated with an angular range of a complex argument of the analytic component signal.

In some embodiments, the fractional-phase representation for one local cycle of the component signal includes a first fractional phase, a second fractional phase, a third fractional phase, and a fourth fractional phase, and wherein the reducing of the plurality of component values into the fractional-phase representation further includes: obtaining, for the first fractional phase, a complex value representing an ordinate and a real value representing an abscissa of a zero crossing of a real part of the component signal, obtaining, for the second fractional phase, a complex value representing an ordinate and a real value representing an abscissa of a zero crossing of an imaginary part of the component signal, obtaining, for the third fractional phase, a complex value representing an ordinate and a real value representing an abscissa of another zero crossing of the real part of the component signal, and obtaining, for the fourth fractional phase, a complex value representing an ordinate and a real value representing an abscissa of another zero crossing of an imaginary part of the component signal.

In some embodiments, each zero crossing is determined by finding a change in sign and interpolating in the neighborhood of the sign change using a curve fit.

In some embodiments, each complex ordinate value is based on an amplitude metric and each real abscissa value is based on a time metric, and wherein the component signal is an electrocardiogram (ECG) signal from a human.

In some embodiments, the invention provides a computer-readable medium having instructions thereon for causing a suitably programmed information processor to execute a method comprising: obtaining a component signal representative a digitally filtered frequency-limited band from a quasi-periodic waveform, wherein the component signal includes a plurality of component values, reducing the plurality of component values into a fractional-phase representation of N fractional phases where N is greater than one, and wherein each fractional phase is associated with a phase label and includes one or more values representing an abscissa, an ordinate, or both an. abscissa and an associated ordinate for each of one or more local cycles of the component signal, and storing the fractional-phase representation in a data structure on a storage device.

In some embodiments of the medium, the fractional-phase representation for one cycle of the component signal includes a first fractional phase, a second fractional phase, a third fractional phase, and a fourth fractional phase, and wherein: the fractional-phase representation for the first fractional phase includes a value representing an abscissa of a zero crossing of the component signal, the fractional-phase representation for the second fractional phase includes a value representing an ordinate and a value representing an abscissa of a maximum of the component signal, the fractional-phase representation for the third fractional phase includes a value representing an abscissa of another zero crossing of the component signal, and the fractional-phase representation for the fourth fractional phase includes a value representing an ordinate and a value representing an abscissa of a minimum of the component signal.

In some embodiments, each ordinate value is based on an amplitude metric and each abscissa value is based on a time metric, and wherein the component signal is an electrocardiogram (ECG) signal from a human.

In some embodiments, each zero crossing is evaluated by finding a change in sign and interpolating in the neighborhood of the sign change using a curve fit.

In some embodiments, the maximum and the minimum of the component signal are each evaluated by finding a change in sign in an estimate of the local derivative and interpolating in the neighborhood of the sign change using a curve fit.

In some embodiments, the fractional-phase representation includes a fractional phase adjustment value such that a linear combination of values derived from the fractional-phase representation with values derived from one or more other fractional-phase representations obtained from other digitally filtered frequency-limited bands substantially reconstructs the quasi-periodic waveform.

In some embodiments, the component signal is analytic such that the plurality of component values for the component signal are complex numbers, and wherein the fractional-phase representation for each fractional phase is associated with an angular range of a complex argument of the analytic component signal.

Some embodiments of the invention provide an apparatus wherein the fractional-phase representation for one local cycle of the component signal includes a first fractional phase, a second fractional phase, a third fractional phase, and a fourth fractional phase, and wherein: the fractional-phase representation for the first fractional phase includes a complex value representing an ordinate and a real value representing an abscissa of a zero crossing of a real part of the component signal, the fractional-phase representation for the second fractional phase includes a complex value representing an ordinate and a real value representing an abscissa of a zero crossing of an imaginary part of the component signal, the fractional-phase representation for the third fractional phase includes a complex value representing an ordinate and a real value representing an abscissa of another zero crossing of the real part of the component signal, the fractional-phase representation for the fourth fractional phase includes a complex value representing an ordinate and a real value representing an abscissa of another zero crossing of an imaginary part of the component signal.

In some embodiments, each zero crossing is evaluated by finding a change in sign and interpolating in the neighborhood of the sign change using a curve fit.

In some embodiments, each complex ordinate value is based on an amplitude metric and each real abscissa value is based on a time metric, and wherein the component signal is an electrocardiogram (ECG) signal from a human.

Some embodiments of the invention provide an apparatus that includes a storage device, a source for a component signal representative of a digitally filtered frequency-limited band from a quasi-periodic waveform, wherein the component signal includes a plurality of component values, and means for reducing the plurality of component values into a fractional-phase representation of N fractional phases where N is greater than one, and wherein each fractional phase is associated with a phase label and includes one or more values representing an abscissa, an ordinate, or both an abscissa and an associated ordinate for each of one or more local cycles of the component signal, and for storing the fractional-phase representation on the storage device.

In some embodiments of the apparatus, the fractional-phase representation for one local cycle of the component signal includes a first fractional phase, a second fractional phase, a third fractional phase, and a fourth fractional phase, and wherein: the fractional-phase representation for the first fractional phase includes a value representing an abscissa of a zero crossing of the component signal, the fractional-phase representation for the second fractional phase includes a value representing an ordinate and a value representing an abscissa of a maximum of the component signal, the fractional-phase representation for the third fractional phase includes a value representing an abscissa of another zero crossing of the component signal, and the fractional-phase representation for the fourth fractional phase includes a value representing an ordinate and a value representing an abscissa of a minimum of the component signal.

In some embodiments, each ordinate value is based on an amplitude metric and each abscissa value is based on a time metric, and wherein the component signal is an electrocardiogram (ECG) signal from a human.

In some embodiments, each zero crossing is evaluated by finding a change in sign and interpolating in the neighborhood of the sign change, e.g., in some embodiments, interpolating using a curve fit.

In some embodiments, the maximum and the minimum of the component signal are each evaluated by finding a change in sign in an estimate of the local derivative and interpolating in the neighborhood of the sign change using a curve fit.

In some embodiments, the fractional-phase representation includes a fractional phase adjustment value such that a linear combination of values derived from the fractional-phase representation with values derived from one or more other fractional-phase representations obtained from other digitally filtered frequency-limited bands substantially reconstructs the quasi-periodic waveform.

In some embodiments, the component signal is analytic such that the plurality of component values for the component signal are complex numbers, and wherein the fractional-phase representation for each fractional phase is associated with an angular range of a complex argument of the analytic component signal.

In some embodiments, the fractional-phase representation for one local cycle of the component signal includes a first fractional phase, a second fractional phase, a third fractional phase, and a fourth fractional phase, and wherein: the fractional-phase representation for the first fractional phase includes a complex value representing an ordinate and a real value representing an abscissa of a zero crossing of a real part of the component signal, the fractional-phase representation for the second fractional phase includes a complex value representing an ordinate and a real value representing an abscissa of a zero crossing of an imaginary part of the component signal, the fractional-phase representation for the third fractional phase includes a complex value representing an ordinate and a real value representing an abscissa of another zero crossing of the real part of the component signal, the fractional-phase representation for the fourth fractional phase includes a complex value representing an ordinate and a real value representing an abscissa of another zero crossing of an imaginary part of the component signal.

In some embodiments, each zero crossing is evaluated by finding a change in sign and interpolating in the neighborhood of the sign change using a curve fit.

In some embodiments, each complex ordinate value is based on an amplitude metric and each real abscissa value is based on a time metric, and wherein the component signal is an electrocardiogram (ECG) signal from a human.

Some embodiments of the invention provide an apparatus that includes: a storage device, a source for a component signal representative, a digitally filtered frequency-limited band from a quasi-periodic waveform, wherein the component signal includes a plurality of component values, and a fractional-phase reducer that operates on the plurality of component values and generates a fractional-phase representation of N fractional phases where N is greater than one, and wherein each fractional phase is associated with a phase label and includes one or more values representing an abscissa, an ordinate, or both an abscissa and an associated ordinate for each of one or more local cycles of the component signal, and wherein the reducer is operatively coupled to store the fractional-phase representation on the storage device.

In some embodiments of the apparatus, the fractional-phase representation for one local cycle of the component signal includes a first fractional phase, a second fractional phase, a third fractional phase, and a fourth fractional phase, and wherein: the fractional-phase representation for the first fractional phase includes a value representing an abscissa of a zero crossing of the component signal, the fractional-phase representation for the second fractional phase includes a value representing an ordinate and a value representing an abscissa of a maximum of the component signal, the fractional-phase representation for the third fractional phase includes a value representing an abscissa of another zero crossing of the component signal, and the fractional-phase representation for the fourth fractional phase includes a value representing an ordinate and a value representing an abscissa of a minimum of the component signal.

In some embodiments, each ordinate value is based on an amplitude metric and each abscissa value is based on a time metric, and wherein the component signal is an electrocardiogram (ECG) signal from a human.

In some embodiments, each zero crossing is evaluated by finding a change in sign and interpolating in the neighborhood of the sign change using a curve fit.

In some embodiments, the maximum and the minimum of the component signal are each evaluated by finding a change in sign in an estimate of the local derivative and interpolating in the neighborhood of the sign change using a curve fit.

In some embodiments, the fractional-phase representation includes a fractional phase adjustment value such that a linear combination of values derived from the fractional-phase representation with values derived from one or more other fractional-phase representations obtained from other digitally filtered frequency-limited bands substantially reconstructs the quasi-periodic waveform.

In some embodiments, the component signal is analytic such that the plurality of component values for the component signal are complex numbers, and wherein the fractional-phase representation for each fractional phase is associated with an angular range of a complex argument of the analytic component signal.

In some embodiments, the number of fractional phases is four and the fractional-phase representation for one local cycle of the component signal includes a first fractional phase, a second fractional phase, a third fractional phase, and a fourth fractional phase, and wherein: the fractional-phase representation for the first fractional phase includes a complex value representing an ordinate and a real value representing an abscissa of a zero crossing of a real part of the component signal, the fractional-phase representation for the second fractional phase includes a complex value representing an ordinate and a real value representing an abscissa of a zero crossing of an imaginary part of the component signal, the fractional-phase representation for the third fractional phase includes a complex value representing an ordinate and a real value representing an abscissa of another zero crossing of the real part of the component signal, the fractional-phase representation for the fourth fractional phase includes a complex value representing an ordinate and a real value representing an abscissa of another zero crossing of an imaginary part of the component signal.

In some embodiments, each zero crossing is evaluated by finding a change in sign and interpolating in the neighborhood of the sign change using a curve fit.

In some embodiments, each complex ordinate value is based on an amplitude metric and each real abscissa value is based on a time metric, and wherein the component signal is an electrocardiogram (ECG) signal from a human.

Some embodiments of the invention provide a computer-readable medium having stored thereon a first data structure for a fractional-phase representation, the data structure including: a descriptor that includes an abscissa value from the fractional-phase representation, a descriptor that includes an ordinate value from the associated fractional-phase representation, and a descriptor that includes an abscissa interval value representing an interval over which an associated fractional phase is active.

In some embodiments of the computer-readable medium, the first data structure further includes three or more descriptors selected from a group consisting of: a descriptor that includes a label identifying a particular data structure from within a plurality of data structures, a descriptor that includes a label identifying the component from a plurality of components, a descriptor that includes a label identifying the quasi-periodic waveform, a descriptor that includes a value representing a local period of the associated component, a descriptor that includes a value representing an interval from a reference abscissa value to an associated abscissa value, a descriptor that includes a value representing a relative measure between the ordinate value associated with the fractional phase, and an ordinate value associated with the component, the quasi-periodic waveform, or both the component and the quasi-periodic waveform, and a descriptor that includes a label indicating that the component is active for the active fractional phase associated with the particular data structure, based upon comparing the ordinate value to a predetermined threshold.

In some embodiments, the first data structure further includes links to other data structures, including: a link to another particular data structure associated with the component, wherein the associated abscissa value of the other data structure is less than the abscissa value associated in the particular data structure, a link to another particular data structure associated with the component, wherein the abscissa value of the other data structure is greater than the abscissa value in the particular data structure, a link to another particular data structure associated with the component, wherein the abscissa value of the other data structure is less than the abscissa value in the particular data structure, and wherein the phase label of the other data structure is of the same value as the phase label of the particular data structure, and a link to another particular data structure associated with the component, wherein the abscissa value of the other data structure is greater than the abscissa value in the particular data structure, and wherein the phase label of the other data structure is of the same value as the phase label of the particular data structure.

In some embodiments, the first data structure further includes linked attributes, including: a descriptor that includes a difference of abscissa values between the abscissa value included in the particular data structure and the abscissa value included in a first linked data structure relative to this particular data structure, a descriptor that includes a difference of abscissa values between the abscissa value included in the particular data structure and the abscissa value included in a second linked data structure relative to this particular data structure, a descriptor that includes an indication of deviation from an expected sequence of phase labels, and a descriptor that includes a moving average of abscissa values for a group of data structures surrounding the particular data structure.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. An apparatus comprising:
   a storage device;
   a receiver configured to receive a component signal representative of a digitally filtered frequency-limited band obtained from a quasi-periodic waveform, wherein the component signal includes a plurality of component values; and
   means for reducing the plurality of component values into a fractional-phase representation of the component signal having a plurality of fractional phases, and wherein each fractional phase is associated with a phase label and includes one or more values representing at least one of an abscissa and an ordinate for each of one or more local cycles of the component signal, and for storing the fractional-phase representation on the storage device.

2. The apparatus of claim 1, wherein the fractional-phase representation for one cycle of the component signal includes a first fractional phase, a second fractional phase, a third fractional phase, and a fourth fractional phase, and wherein the means for reducing further includes:
   means for obtaining a value representing an abscissa of a zero crossing of the component signal for the first fractional phase;
   means for obtaining a value representing an ordinate and a value representing an abscissa of a maximum of the component signal for the second fractional phase;
   means for obtaining a value representing an abscissa of another zero crossing of the component signal for the third fractional phase; and
   means for obtaining a value representing an ordinate and a value representing an abscissa of a minimum of the component signal for the fourth fractional phase.

3. The apparatus of claim 2, wherein the means for obtaining each ordinate value uses an amplitude metric and the means for obtaining each abscissa value uses a time metric, and wherein the quasi-periodic waveform is an electrocardiogram (ECG) signal from a human.

4. The apparatus of claim 2, wherein the means for obtaining of the value representing the abscissa for each zero crossing includes means for finding a change in sign and interpolating in the neighborhood of the sign change.

5. The apparatus of claim 2, wherein the means for obtaining of the values representing the ordinates for the maximum and the minimum of the component signal includes means for finding a change in sign in an estimate of a local derivative and means for interpolating in the neighborhood of the derivative's sign change.

6. The apparatus of claim 1, further comprising means for obtaining a phase-adjustment value for the fractional-phase representation such that a linear combination of values derived from the fractional-phase representation with values derived from one or more other fractional-phase representations obtained from other digitally filtered frequency-limited bands substantially reconstructs the quasi-periodic waveform.

7. The apparatus of claim 1, wherein the plurality of component values are complex numbers, and wherein the fractional-phase representation for each fractional phase is associated with an angular range of a complex argument of the component signal.

8. The apparatus of claim 7, wherein the fractional-phase representation for one cycle of the component signal includes a first fractional phase, a second fractional phase, a third fractional phase, and a fourth fractional phase, and wherein the means for reducing the plurality of component values into the fractional-phase representation further comprises:
   means for obtaining, for the first fractional phase, a complex value representing an ordinate and a real value representing an abscissa of a zero crossing of a real part of the component signal;
   means for obtaining, for the second fractional phase, a complex value representing an ordinate and a real value representing an abscissa of a zero crossing of an imaginary part of the component signal;
   means for obtaining, for the third fractional phase, a complex value representing an ordinate and a real value representing an abscissa of another zero crossing of the real part of the component signal; and
   means for obtaining, for the fourth fractional phase, a complex value representing an ordinate and a real value representing an abscissa of another zero crossing of an imaginary part of the component signal.

9. An apparatus comprising:
   a storage device;
   a receiver configured to receive a component signal representative of a digitally filtered frequency-limited band obtained from a quasi-periodic waveform, wherein the component signal includes a plurality of component values; and
   a processor configured to operate on the plurality of component values and to generate a fractional-phase representation of a plurality of fractional phases, and wherein each fractional phase is associated with a phase label and includes at least one of an abscissa and an ordinate for each of one or more local cycles of the component signal, and wherein the processor is operatively coupled to store the fractional-phase representation on the storage device.

10. The apparatus of claim 9, wherein the fractional-phase representation for one cycle of the component signal includes a first fractional phase, a second fractional phase, a third fractional phase, and a fourth fractional phase, and wherein the processor is further configured such that:
   the fractional-phase representation for the first fractional phase includes a value representing an abscissa of a zero crossing of the component signal;
   the fractional-phase representation for the second fractional phase includes a value representing an ordinate and a value representing an abscissa of a maximum of the component signal;

the fractional-phase representation for the third fractional phase includes a value representing an abscissa of another zero crossing of the component signal; and the fractional-phase representation for the fourth fractional phase includes a value representing an ordinate and a value representing an abscissa of a minimum of the component signal.

11. The apparatus of claim 10, wherein the processor is further configured such that each ordinate value is based on an amplitude metric and each abscissa value is based on a time metric, and wherein the quasi-periodic waveform is an electrocardiogram (ECG) signal from a human.

12. The apparatus of claim 10, wherein the processor is further configured such that each zero crossing is determined by finding a change in sign and interpolating in the neighborhood of the sign change using a curve fit.

13. The apparatus of claim 10, wherein the processor is further configured such that the maximum and the minimum of the component signal are each evaluated by finding a change in sign in an estimate of the local derivative and interpolating in the neighborhood of the derivative's sign change using a curve fit.

14. The apparatus of claim 9, wherein the processor is further configured such that the fractional-phase representation the processor generates includes a fractional phase adjustment value such that a linear combination of values derived from the fractional-phase representation with values derived from one or more other fractional-phase representations obtained from other digitally filtered frequency-limited bands substantially reconstructs the quasi-periodic waveform.

15. The apparatus of claim 9, wherein the processor is further configured such that the plurality of component values are complex numbers, and wherein the fractional-phase representation for each fractional phase is associated with an angular range of a complex argument of the component signal.

16. The apparatus of claim 15, wherein the fractional-phase representation for one cycle of the component signal includes a first fractional phase, a second fractional phase, a third fractional phase, and a fourth fractional phase, and wherein the processor is further configured such that:

the fractional-phase representation for the first fractional phase includes a complex value representing an ordinate and a real value representing an abscissa of a zero crossing of a real part of the component signal;

the fractional-phase representation for the second fractional phase includes a complex value representing an ordinate and a real value representing an abscissa of a zero crossing of an imaginary part of the component signal;

the fractional-phase representation for the third fractional phase includes a complex value representing an ordinate and a real value representing an abscissa of another zero crossing of the real part of the component signal; and the fractional-phase representation for the fourth fractional phase includes a complex value representing an ordinate and a real value representing an abscissa of another zero crossing of an imaginary part of the component signal.

17. The apparatus of claim 16, wherein the processor is further configured such that each zero crossing is determined by finding a change in sign and interpolating in a neighborhood of the sign change.

18. The apparatus of claim 16, wherein each complex ordinate value is based on an amplitude metric and each real abscissa value is based on a time metric, and wherein the quasi-periodic waveform is an electrocardiogram (ECG) signal from a human.

19. An apparatus comprising:

a storage device;

a receiver configured to receive a component signal representative of a digitally filtered frequency-limited band obtained from a quasi-periodic waveform, wherein the component signal includes a plurality of component values; and a reducer configured to operate on the plurality of component values and to generate a fractional-phase representation of a plurality of fractional phases, and wherein each fractional phase is associated with a phase label and includes at least one of an abscissa and an ordinate for each of one or more local cycles of the component signal, and wherein the reducer is operatively coupled to store the fractional-phase representation;

a phase-label generator operatively coupled to store at least one label for the fractional-phase representation; and an abscissa-interval-indication generator operatively coupled to store an interval indicator of at least one interval over which a fractional phase is active.

20. The apparatus of claim 19, further comprising a processor configured to store at least three attributes selected from a group consisting of:

a data-structure-label attribute identifying a particular data structure from within a plurality of data structures;

a component-label attribute identifying a component from a plurality of components;

a waveform-label attribute identifying the quasi-periodic waveform;

a local-period attribute representing a local period of the component;

a relative-ordinate attribute representing a relative measure between a first ordinate value associated with the active fractional phase, and a second ordinate value associated with at least one of a component and the quasi-periodic waveform; and an active-component-label attribute descriptor that indicates whether the component is active for an active fractional phase, based upon comparing the ordinate value to a predetermined threshold.

21. The apparatus of claim 19, further comprising a processor configured to store a data structure comprising:

a phase-label attribute of a fractional-phase representation;

an abscissa attribute of the fractional-phase representation;

an ordinate attribute of the fractional-phase representation; and an abscissa-interval attribute of an interval over which a fractional phase is active.

22. A computer-readable media having stored thereon a first data structure comprising:

a phase-label attribute of a fractional-phase representation;

an abscissa attribute of the fractional-phase representation;

an ordinate attribute of the fractional-phase representation; and an abscissa-interval attribute of an interval over which a fractional phase is active.

23. The computer-readable media of claim 22, wherein the first data structure further comprises at least three attributes selected from a group consisting of:

a data-structure-label attribute identifying a particular data structure from within a plurality of data structures;

a component-label attribute identifying a component from a plurality of components;

a waveform-label attribute identifying the quasi-periodic waveform;

a local-period attribute representing a local period of the component;

a relative-ordinate attribute representing a relative measure between a first ordinate value associated with the active fractional phase, and a second ordinate value associated with at least one of a component and the quasi-periodic waveform; and an active-component-label attribute descriptor that indicates whether the component is active for an active fractional phase, based upon comparing the ordinate value to a predetermined threshold.

24. The computer-readable media of claim 22, wherein the first data structure further comprises:

a link to a second data structure associated with the component, wherein an abscissa attribute of the second data structure is less than the abscissa attribute of the first data structure;

a link to a third data structure associated with the component, wherein an abscissa attribute of the third data structure is greater than the abscissa attribute of the first data structure;

a link to a fourth data structure associated with the component, wherein an abscissa attribute of the fourth data structure is less than the abscissa attribute in the first data structure, and wherein a phase-label attribute of the fourth data structure is equal to the phase-label attribute of the first data structure; and a link to a fifth data structure associated with the component, wherein an abscissa attribute of the fifth data structure is greater than the abscissa value in the first data structure, and wherein a phase-label attribute of the fifth data structure is equal to the phase-label attribute of the first data structure.

25. The computer-readable media of claim 24, wherein the first data structure further comprises linked attributes, including:

a first abscissa-difference attribute that includes a difference of abscissa values between the abscissa attribute included in the first data structure and an abscissa attribute included in another data structure that is first-linked relative to the first data structure;

a second abscissa-difference attribute that includes a difference of abscissa values between the abscissa value included in the particular data structure and an abscissa value included in another data structure that is second-linked relative to the first data structure;

a phase-label deviation attribute that includes an indication of deviation from an expected sequence of phase labels; and a moving-statistic attribute that includes a moving statistic over a group of ordinate values for a group of data structures surrounding the first data structure.

\* \* \* \* \*